United States Patent [19]
Niwa et al.

[11] Patent Number: 5,804,429
[45] Date of Patent: Sep. 8, 1998

[54] CEPHALOSPORIN C ACYLASE

[75] Inventors: Mineo Niwa, Muko; Yoshimasa Saito, Kawanishi; Takao Fujimura, Ibaraki; Yoshinori Ishii, Kobe; Yuji Noguchi, Osakasayama, all of Japan

[73] Assignee: Fujisawa Pharmaceutical Co., Ltd., Osaka, Japan

[21] Appl. No.: 633,760

[22] PCT Filed: Oct. 26, 1994

[86] PCT No.: PCT/JP94/01799

§ 371 Date: May 1, 1996

§ 102(e) Date: May 1, 1996

[87] PCT Pub. No.: WO95/12680

PCT Pub. Date: May 11, 1995

[30] Foreign Application Priority Data

Nov. 1, 1993 [GB] United Kingdom .................... 9322508
Dec. 29, 1993 [GB] United Kingdom .................... 9326519

[51] Int. Cl.⁶ .............................. C12N 9/80; C12N 15/00; C12P 21/06; C07H 21/04
[52] U.S. Cl. .......................... 435/228; 435/69.1; 435/49; 435/51; 435/172.3; 435/252.3; 435/320.1; 536/23.2
[58] Field of Search ..................................... 435/228, 69.1, 435/252.3, 320.1, 49, 51, 47, 172.3; 536/23.2

[56] References Cited

U.S. PATENT DOCUMENTS 5,336,613  2/1993  Niwa et al. .............................. 435/228

FOREIGN PATENT DOCUMENTS 0 475 652  3/1992  European Pat. Off. .
0 482 844  4/1992  European Pat. Off. .
0 558 241  9/1993  European Pat. Off. .

OTHER PUBLICATIONS

Journal of Fermentation and Bioengineering, vol. 72, No. 4, pp. 232–242, 1991, I. Aramori, et al., "Cloning and Nucleotide Sequencing of New Glutaryl 7–ACA and Cephalosporin C Acylase Genes from Pseudomonas Strains".

Biochimica Et Biophysica Acta, vol. 1132, No. 3, pp. 233–239, 1992, M. Ishiye, et al., "Nucleotide Sequence and Expression in *Escherichia coli* of the Cephalosporin Acylase Gene of a Pseudomonas Strain".

*Primary Examiner*—Robert A. Wax
*Assistant Examiner*—Tekchand Saidha
*Attorney, Agent, or Firm*—Oblon, Spivak, McClelland, Maier & Neustadt, P.C.

[57] ABSTRACT

A mutant CC acylase wherein at least one amino acid at the $Ala^{49}$, $Met^{164}$, $Ser^{166}$, $Met^{174}$, $Glu^{358}$, $Met^{465}$, $Met^{506}$, or $Met^{750}$ position of the amino acid sequence of the native CC acylase is replaced by a different amino acid, a DNA coding therefor, an expression vector containing the said DNA, a microorganism transformed with the said expression vector, the production of the CC acylase by culturing the said transformant, and use thereof for the production of a compound. The mutant CC acylase of the invention has desirable properties in terms of enzymatic potency, alteration of pH profile, efficiency of processing, and the like.

8 Claims, 50 Drawing Sheets

1.   164
   GlyLeuLeuAlaGlySerValTrpPhe

SO-M164A   (29)   5'   GGGCCTGCTTGCGGGATCCGTGTGGTTCA (BamHI)

2.   174
   LeuTrpArgAlaLeuAlaLeuPro

SO-M174A   (26)   5'   GCTCTGGCGGGCGCTAGCGCTGCCGG (Eco47III)

3.   465
   HisGluAlaAlaProArgValIle

SO-M465A   (26)   5'   GCACGAGGCGGCGCCACGCGTGATCG (NarI)   (MluI)

4.   506
   GluArgIleAlaLysArgLeuValAla

SO-M506A   (28)   5'   GAGCGCATCGCGAAGCGCTTGGTCGCCA (Eco47III)

5.   750
   AspCysAlaAlaValProMetLeu

SO-M750A   (26)   5'   CGACTGTGCGGCGGTACCGATGCTCT (KpnI)

*FIG.1A*

6.                                49
                    AlaSerGlyGluLeuAspAlaTyrArg

SO-A49L      (27)   5'   GCCTCGGGCGAGCTCGATGCCTATCGG (SacI)

SO-S166A     (36)   5'   CATCCGCCAAAGCTTGAACCACACCGCACCCATAAG (HindIII)

(B) OLIGOMER FOR PCR MUTATION (I) FOR M164 MUTANT ACYLASES 1.                                70
                    MetGluLeuThrArgArgLysAlaLeuGlyArg

SO-MluFor    (33)   5'   ATGGAGCTGACGCGTCGCAAAGCGCTGGGACG (MluI)      (Eco47III)

2.                                164
                    ValMetArgArgLeuGlyleuLeuCysGlySerVal

SO-M164C     (38)        CGGTGATGCGTCGACTCGGCCTGCTTTGCGGATCCGTG

3'   GCCACTACGCAGCTGAGCCGGACGAAACGCCTAGGCAC (SalI)              (BamHI)

3.  SO-M164D   (38)  5'  CACGGATCCATCAAGCAGGCCGAGTCGACGCATCACCG

4.  SO-M164E   (38)  5'  CACGGATCCTTCAAGCAGGCCGAGTCGACGCATCACCG

5.  SO-M164F   (38)  5'  CACGGATCCGAAAAGCAGGCCGAGTCGACGCATCACCG

*FIG.1B*

6. SO-M164G  (38) 5'  CACGGATCCGCCAAGCAGGCCGAGTCGACGCATCACCG
7. SO-M164H  (38) 5'  CACGGATCCATGAAGCAGGCCGAGTCGACGCATCACCG
8. SO-M164I  (38) 5'  CACGGATCCGATAAGCAGGCCGAGTCGACGCATCACCG
9. SO-M164K  (38) 5'  CACGGATCCCTTAAGCAGGCCGAGTCGACGCATCACCG
10. SO-M164L (38) 5'  CACGGATCCCAGAAGCAGGCCGAGTCGACGCATCACCG
11. SO-M164N (38) 5'  CACGGATCCGTTAAGCAGGCCGAGTCGACGCATCACCG
12. SO-M164P (38) 5'  CACGGATCCCGGAAGCAGGCCGAGTCGACGCATCACCG
13. SO-M164Q (38) 5'  CACGGATCCCTGAAGCAGGCCGAGTCGACGCATCACCG
14. SO-M164R (38) 5'  CACGGATCCACGAAGCAGGCCGAGTCGACGCATCACCG
15. SO-M164S (38) 5'  CACGGATCCCGAAAGCAGGCCGAGTCGACGCATCACCG
16. SO-M164T (38) 5'  CACGGATCCCGTAAGCAGGCCGAGTCGACGCATCACCG
17. SO-M164V (38) 5'  CACGGATCCCACAAGCAGGCCGAGTCGACGCATCACCG
18. SO-M164W (38) 5'  CACGGATCCCCAAAGCAGGCCGAGTCGACGCATCACCG
19. SO-M164Y (38) 5'  CACGGATCCATAAAGCAGGCCGAGTCGACGCATCACCG (ii) for E358 MUTANT ACYLASES 1.                                    265
                          ArgValPheGluIleProGlyIle SO-BstFor   (26)   5'   ATCGCGTCTTCGAAATACCGGGCATC (BstBI)

```
                                  358
                       PheAspIleValLysThrArgHisGlyProVal

AGTTCGATATAGTCAAGACGCGCCATGGCCCGGTTA

SO-E358K   (36)  3' TCAAGCTATATCAGTTCTGCGCGGTACCGGGCCAAT
                                              (NcoI)

3. SO-E358L   (36)  5' TAACCGGGCCATGGCGCGTCAGGACTATATCGAACT

4. SO-E358R   (36)  5' TAACCGGGCCATGGCGCGTGCGGACTATATCGAACT

5. SO-E358S   (36)  5' TAACCGGGCCATGGCGCGTCGAGACTATATCGAACT

6. SO-E358T   (36)  5' TAACCGGGCCATGGCGCGTGGTGACTATATCGAACT
```

*FIG.1D*

Single-stranded U-DNA of mp19pfu62

|  | plasmid A | plasmid B | vector |
|---|---|---|---|
| (vi) | pCKM164A | pCKM269Y | p164A269Y |
| (vii) | p164L174A | pCKM269Y | p164L174A269Y |
|  | " | pCKM269F | p164L174A269F |
|  | " | p269Y305S | p164A174A269Y305S |

```
        10         20         30         40         50         60
ATGACTATGGCAGCTAATACGGATCGCGCGGTCTTGCAGGCGGCGCTGCCGCCGCTTTCC
 M  T  M  A  A  N  T  D  R  A  V  L  Q  A  A  L  P  P  L  S 70         80         90        100        110        120
GGCAGCCTCCCCATTCCCGGATTGAGCGCGTCGGTCCGCGTCCGGCGCGATGCCTGGGGC
 G  S  L  P  I  P  G  L  S  A  S  V  R  V  R  R  D  A  W  G 130        140        150        160        170        180
ATCCCGCATATCAAGGCCTCGGGCGAGGCCGATGCCTATCGGGCGCTGGGCTTCGTCCAT
 I  P  H  I  K  A  S  G  E  A  D  A  Y  R  A  L  G  F  V  H 190        200        210        220        230        240
TCGCAGGACCGTCTTTTCCAGATGGAGCTGACGCGTCGCAAGGCGCTGGGACGCGCGGCC
 S  Q  D  R  L  F  Q  M  E  L  T  R  R  K  A  L  G  R  A  A 250        260        270        280        290        300
GAATGGCTGGGCGCCGAGGCCGCCGAGGCCGATATCCTCGTGCGCCGGCTCGGAATGGAA
 E  W  L  G  A  E  A  A  E  A  D  I  L  V  R  R  L  G  M  E 310        320        330        340        350        360
AAAGTCTGCCGGCGCGACTTCGAGGCCTTGGGCGTCGAGGCGAAGGACATGCTGCGGGCT
 K  V  C  R  R  D  F  E  A  L  G  V  E  A  K  D  M  L  R  A 370        380        390        400        410        420
TATGTCGCCGGCGTGAACGCATTCCTGGCTTCCGGTGCTCCCCTGCCTGTCGAATACGGA
 Y  V  A  G  V  N  A  F  L  A  S  G  A  P  L  P  V  E  Y  G 430        440        450        460        470        480
TTGCTCGGAGCAGAGCCGGAGCCCTGGGAGCCTTGGCACAGCATCGCGGTGATGCGCCGG
 L  L  G  A  E  P  E  P  W  E  P  W  H  S  I  A  V  M  R  R
```

*FIG. 22A*

```
            490         500         510         520         530         540
      CTGGGCCTGCTTGCGGGATCCGTGTGGTTCAAGCTCTGGCGGATGCTGGCGCTGCCGGTG
       L  G  L  L  A  G  S  V  W  F  K  L  W  R  M  L  A  L  P  V 550         560         570         580         590         600
      GTCGGAGCCGCGAATGCGCTGAAGCTGCGCTATGACGATGGCGGCCGGGATTTGCTCTGC
       V  G  A  A  N  A  L  K  L  R  Y  D  D  G  G  R  D  L  L  C 610         620         630         640         650         660
      ATCCCGCCGGGCGCCGAAGCCGATCGGCTCGAGGCGGATCTCGCGACCCTGCGGCCCGCG
       I  P  P  G  A  E  A  D  R  L  E  A  D  L  A  T  L  R  P  A 670         680         690         700         710         720
      GTCGATGCGCTGCTGAAGGCGATGGGCGGCGATGCCTCCGATGCTGCCGGCGGCGGCAGC
       V  D  A  L  L  K  A  M  G  G  D  A  S  D  A  A  G  G  G  S 730         740         750         760         770         780
      AACAACTGGGCGGTCGCTCCGGGCCGCACGGCGACCGGCAGGCCGATCCTCGCGGGCGAT
       N  N  W  A  V  A  P  G  R  T  A  T  G  R  P  I  L  A  G  D 790         800         810         820         830         840
      CCGCATCGCGTCTTCGAAATCCCGGGCATGTATGCGCAGCATCATCTGGCCTGCGACCGG
       P  H  R  V  F  E  I  P  G  M  Y  A  Q  H  H  L  A  C  D  R 850         860         870         880         890         900
      TTCGACATGATCGGCCTGACCGTGCCGGGCGTGCCGGGCTTCCCGCACTTCGCGCATAAC
       F  D  M  I  G  L  T  V  P  G  V  P  G  F  P  H  F  A  H  N 910         920         930         940         950         960
      GGCAAGGTCGCCTATTGCGTCACCCATGCCTTCATGGACATCCACGATCTCTATCTCGAG
       G  K  V  A  Y  C  V  T  H  A  F  M  D  I  H  D  L  Y  L  E
```

*FIG. 22B*

```
       970       980       990      1000      1010      1020
CAGTTCGCGGGGGAGGGCCGCACTGCGCGGTTCGGCAACGATTTCGAGCCCGTCGCCTGG
 Q   F   A   G   E   G   R   T   A   R   F   G   N   D   F   E   P   V   A   W 1030      1040      1050      1060      1070      1080
AGCCGGGACCGTATCGCGGTCCGGGGTGGCGCCGATCGCGAGTTCGATATCGTCGAGACG
 S   R   D   R   I   A   V   R   G   G   A   D   R   E   F   D   I   V   E   T 1090      1100      1110      1120      1130      1140
CGCCATGGCCCCGGTTATCGCGGGCGATCCGCGCGATGGCGCAGCGCTCACGCTGCGTTCG
 R   H   G   P   V   I   A   G   D   P   R   D   G   A   A   L   T   L   R   S 1150      1160      1170      1180      1190      1200
GTCCAGTTCGCCGAGACCGATCTGTCCTTCGACTGCCTGACGCGGATGCCGGGCGCATCG
 V   Q   F   A   E   T   D   L   S   F   D   C   L   T   R   M   P   G   A   S 1210      1220      1230      1240      1250      1260
ACCGTGGCCCAGCTCTACGACGCGACGCGCGGCTGGGGCCTGATCGACCATAACCTCGTC
 T   V   A   Q   L   Y   D   A   T   R   G   W   G   L   I   D   H   N   L   V 1270      1280      1290      1300      1310      1320
GCCGGGGATGTCGCGGGCTCGATCGGCCATCTGGTCCGCGCCCGCGTTCCGTCCCGTCCG
 A   G   D   V   A   G   S   I   G   H   L   V   R   A   R   V   P   S   R   P 1330      1340      1350      1360      1370      1380
CGCGAAAACGGCTGGCTGCCGGTGCCGGGCTGGTCCGGCGAGCATGAATGGCGGGGCTGG
 R   E   N   G   W   L   P   V   P   G   W   S   G   E   H   E   W   R   G   W 1390      1400      1410      1420      1430      1440
ATTCCGCACGAGGCGATGCCGCGCGTGATCGATCCGCCGGGCGGCATCATCGTCACGGCG
 I   P   H   E   A   M   P   R   V   I   D   P   P   G   G   I   I   V   T   A
```

*FIG. 22C*

```
      1450      1460      1470      1480      1490      1500
AATAATCGCGTCGTGGCCGATGACCATCCCGATTATCTCTGCACCGATTGCCATCCGCCC
 N  N  R  V  V  A  D  D  H  P  D  Y  L  C  T  D  C  H  P  P 1510      1520      1530      1540      1550      1560
TACCGCGCCGAGCGCATCATGAAGCGCCTGGTCGCCAATCCGGCTTTCGCCGTCGACGAT
 Y  R  A  E  R  I  M  K  R  L  V  A  N  P  A  F  A  V  D  D 1570      1580      1590      1600      1610      1620
GCCGCCGCGATCCATGCCGATACGCTGTCGCCCCATGTCGGGTTGCTGCGCCGGAGGCTC
 A  A  A  I  H  A  D  T  L  S  P  H  V  G  L  L  R  R  R  L 1630      1640      1650      1660      1670      1680
GAGGCGCTTGGAGCCCGCGACGACTCCGCGGCCGAAGGGCTGAGGCAGATGCTCGTCGCC
 E  A  L  G  A  R  D  D  S  A  A  E  G  L  R  Q  M  L  V  A 1690      1700      1710      1720      1730      1740
TGGGACGGCCGCATGGATGCGGCTTCGGAGGTCGCGTCTGCCTACAATGCGTTCCGCAGG
 W  D  G  R  M  D  A  A  S  E  V  A  S  A  Y  N  A  F  R  R 1750      1760      1770      1780      1790      1800
GCGCTGACGCGGCTGGTGACGGACCGCAGCGGGCTGGAGCAGGCGATATCGCATCCCTTC
 A  L  T  R  L  V  T  D  R  S  G  L  E  Q  A  I  S  H  P  F 1810      1820      1830      1840      1850      1860
GCGGCTGTCGCGCCGGGCGTCTCACCGCAAGGCCAGGTCTGGTGGGCCGTGCCGACCCTG
 A  A  V  A  P  G  V  S  P  Q  G  Q  V  W  W  A  V  P  T  L 1870      1880      1890      1900      1910      1920
CTGCCGCGACGACGATGCCGGAATGCTGAAGGGCTGGAGCTGGGACCAGGCCTTGTCTGAG
 L  R  D  D  D  A  G  M  L  K  G  W  S  W  D  Q  A  L  S  E
```

*FIG. 22D*

```
              1930      1940      1950      1960      1970      1980
         GCCCTCTCGGTCGCGTCGCAGAACCTGACCGGGCGAAGCTGGGGCGAAGAGCATCGGCCG
          A  L  S  V  A  S  Q  N  L  T  G  R  S  W  G  E  E  H  R  P 1990      2000      2010      2020      2030      2040
         CGCTTCACGCATCCGCTTGCCACGCAATTCCCGGCCTGGGCGGGGCTGCTGAATCCGGCT
          R  F  T  H  P  L  A  T  Q  F  P  A  W  A  G  L  L  N  P  A 2050      2060      2070      2080      2090      2100
         TCCCGTCCGATCGGTGGCGATGGCGATACCGTGCTGGCGAACGGGCTCGTCCCGTCAGCC
          S  R  P  I  G  G  D  G  D  T  V  L  A  N  G  L  V  P  S  A 2110      2120      2130      2140      2150      2160
         GGGCCGCAGGCGACCTATGGTGCCCTGTCGCGCTACGTCTTCGATGTCGGCAATTGGGAC
          G  P  Q  A  T  Y  G  A  L  S  R  Y  V  F  D  V  G  N  W  D 2170      2180      2190      2200      2210      2220
         AATAGCCGCTGGGTCGTCTTCCACGGCGCCTCCGGGCATCCGGCCAGCGCCCATTATGCC
          N  S  R  W  V  V  F  H  G  A  S  G  H  P  A  S  A  H  Y  A 2230      2240      2250      2260      2270      2280
         GATCAGAATGCGCCCTGGAGCGACTGTGCGATGGTGCCGATGCTCTATAGCTGGGACAGG
          D  Q  N  A  P  W  S  D  C  A  M  V  P  M  L  Y  S  W  D  R 2290      2300      2310      2320
         ATCGCGGCAGAGGCCGTGACGTCGCAGGAACTCGTCCCGGCCTGA
          I  A  A  E  A  V  T  S  Q  E  L  V  P  A  *
```

*FIG. 22E*

```
         10        20        30        40        50        60
ATGACTATGGCAGCTAATACGGATCGCGCGGTCTTGCAGGCGGCGCTGCCGCCGCTTTCC
 M  T  M  A  A  N  T  D  R  A  V  L  Q  A  A  L  P  P  L  S 70        80        90       100       110       120
GGCAGCCTCCCCATTCCCGGATTGAGCGCGTCGGTCCGCGTCCGGCGCGATGCCTGGGGC
 G  S  L  P  I  P  G  L  S  A  S  V  R  V  R  R  D  A  W  G 130       140       150       160       170       180
ATCCCGCATATCAAGGCCTCGGGCGAGGCCGATGCCTATCGGGCGCTGGGCTTCGTCCAT
 I  P  H  I  K  A  S  G  E  A  D  A  Y  R  A  L  G  F  V  H 190       200       210       220       230       240
TCGCAGGACCGTCTTTTCCAGATGGAGCTGACGCGTCGCAAGGCGCTGGGACGCGCGGCC
 S  Q  D  R  L  F  Q  M  E  L  T  R  R  K  A  L  G  R  A  A 250       260       270       280       290       300
GAATGGCTGGGCGCCGAGGCCGCCGAGGCCGATATCCTCGTGCGCCGGCTCGGAATGGAA
 E  W  L  G  A  E  A  A  E  A  D  I  L  V  R  R  L  G  M  E 310       320       330       340       350       360
AAAGTCTGCCGGCGCGACTTCGAGGCCTTGGGCGTCGAGGCGAAGGACATGCTGCGGGCT
 K  V  C  R  R  D  F  E  A  L  G  V  E  A  K  D  M  L  R  A 370       380       390       400       410       420
TATGTCGCCGGCGTGAACGCATTCCTGGCTTCCGGTGCTCCCCTGCCTGTCGAATACGGA
 Y  V  A  G  V  N  A  F  L  A  S  G  A  P  L  P  V  E  Y  G 430       440       450       460       470       480
TTGCTCGGAGCAGAGCCGGAGCCCTGGGAGCCTTGGCACAGCATCGCGGTGATGCGCCGG
 L  L  G  A  E  P  E  P  W  E  P  W  H  S  I  A  V  M  R  R
```

*FIG. 23A*

```
         490       500       510       520       530       540
CTGGGCCTGCTTATGGGTGCGGTGTGGTTCAAGCTTTGGCGGATGCTGGCGCTGCCGGTG
 L  G  L  L  M  G  A  V  W  F  K  L  W  R  M  L  A  L  P  V 550       560       570       580       590       600
GTCGGAGCCGCGAATGCGCTGAAGCTGCGCTATGACGATGGCGGCCGGGATTTGCTCTGC
 V  G  A  A  N  A  L  K  L  R  Y  D  D  G  G  R  D  L  L  C 610       620       630       640       650       660
ATCCCGCCGGGCGCCGAAGCCGATCGGCTCGAGGCGGATCTCGCGACCCTGCGGCCCGCG
 I  P  P  G  A  E  A  D  R  L  E  A  D  L  A  T  L  R  P  A 670       680       690       700       710       720
GTCGATGCGCTGCTGAAGGCGATGGGCGGCGATGCCTCCGATGCTGCCGGCGGCGGCAGC
 V  D  A  L  L  K  A  M  G  G  D  A  S  D  A  A  G  G  G  S 730       740       750       760       770       780
AACAACTGGGCGGTCGCTCCGGGCCGCACGGCGACCGGCAGGCCGATCCTCGCGGGCGAT
 N  N  W  A  V  A  P  G  R  T  A  T  G  R  P  I  L  A  G  D 790       800       810       820       830       840
CCGCATCGCGTCTTCGAAATCCCGGGCATGTATGCGCAGCATCATCTGGCCTGCGACCGG
 P  H  R  V  F  E  I  P  G  M  Y  A  Q  H  H  L  A  C  D  R 850       860       870       880       890       900
TTCGACATGATCGGCCTGACCGTGCCGGGCGTGCCGGGCTTCCCGCACTTCGCGCATAAC
 F  D  M  I  G  L  T  V  P  G  V  P  G  F  P  H  F  A  H  N 910       920       930       940       950       960
GGCAAGGTCGCCTATTGCGTCACCCATGCCTTCATGGACATCCACGATCTCTATCTCGAG
 G  K  V  A  Y  C  V  T  H  A  F  M  D  I  H  D  L  Y  L  E
```

*FIG. 23B*

```
           970       980       990      1000      1010      1020
CAGTTCGCGGGGGAGGGCCGCACTGCGCGGTTCGGCAACGATTTCGAGCCCGTCGCCTGG
 Q   F   A   G   E   G   R   T   A   R   F   G   N   D   F   E   P   V   A   W 1030      1040      1050      1060      1070      1080
AGCCGGGACCGTATCGCGGTCCGGGGTGGCGCCGATCGCGAGTTCGATATCGTCGAGACG
 S   R   D   R   I   A   V   R   G   G   A   D   R   E   F   D   I   V   E   T 1090      1100      1110      1120      1130      1140
CGCCATGGCCCCGGTTATCGCGGGCGATCCGCGCGATGGCGCAGCGCTCACGCTGCGTTCG
 R   H   G   P   V   I   A   G   D   P   R   D   G   A   A   L   T   L   R   S 1150      1160      1170      1180      1190      1200
GTCCAGTTCGCCGAGACCGATCTGTCCTTCGACTGCCTGACGCGGATGCCGGGCGCATCG
 V   Q   F   A   E   T   D   L   S   F   D   C   L   T   R   M   P   G   A   S 1210      1220      1230      1240      1250      1260
ACCGTGGCCCAGCTCTACGACGCGACGCGCGGCTGGGGCCTGATCGACCATAACCTCGTC
 T   V   A   Q   L   Y   D   A   T   R   G   W   G   L   I   D   H   N   L   V 1270      1280      1290      1300      1310      1320
GCCGGGGATGTCGCGGGCTCGATCGGCCATCTGGTCCGCGCCCGCGTTCCGTCCCGTCCG
 A   G   D   V   A   G   S   I   G   H   L   V   R   A   R   V   P   S   R   P 1330      1340      1350      1360      1370      1380
CGCGAAAACGGCTGGCTGCCGGTGCCGGGCTGGTCCGGCGAGCATGAATGGCGGGGCTGG
 R   E   N   G   W   L   P   V   P   G   W   S   G   E   H   E   W   R   G   W 1390      1400      1410      1420      1430      1440
ATTCCGCACGAGGCGATGCCGCGCGTGATCGATCCGCCGGGCGGCATCATCGTCACGGCG
 I   P   H   E   A   M   P   R   V   I   D   P   P   G   G   I   I   V   T   A
```

*FIG. 23C*

```
      1450      1460      1470      1480      1490      1500
AATAATCGCGTCGTGGCCGATGACCATCCCGATTATCTCTGCACCGATTGCCATCCGCCC
 N  N  R  V  V  A  D  D  H  P  D  Y  L  C  T  D  C  H  P  P 1510      1520      1530      1540      1550      1560
TACCGCGCCGAGCGCATCATGAAGCGCCTGGTCGCCAATCCGGCTTTCGCCGTCGACGAT
 Y  R  A  E  R  I  M  K  R  L  V  A  N  P  A  F  A  V  D  D 1570      1580      1590      1600      1610      1620
GCCGCCGCGATCCATGCCGATACGCTGTCGCCCCATGTCGGGTTGCTGCGCCGGAGGCTC
 A  A  A  I  H  A  D  T  L  S  P  H  V  G  L  L  R  R  R  L 1630      1640      1650      1660      1670      1680
GAGGCGCTTGGAGCCCGCGACGACTCCGCGGCCGAAGGGCTGAGGCAGATGCTCGTCGCC
 E  A  L  G  A  R  D  D  S  A  A  E  G  L  R  Q  M  L  V  A 1690      1700      1710      1720      1730      1740
TGGGACGGCCGCATGGATGCGGCTTCGGAGGTCGCGTCTGCCTACAATGCGTTCCGCAGG
 W  D  G  R  M  D  A  A  S  E  V  A  S  A  Y  N  A  F  R  R 1750      1760      1770      1780      1790      1800
GCGCTGACGCGGCTGGTGACGGACCGCAGCGGGCTGGAGCAGGCGATATCGCATCCCTTC
 A  L  T  R  L  V  T  D  R  S  G  L  E  Q  A  I  S  H  P  F 1810      1820      1830      1840      1850      1860
GCGGCTGTCGCGCCGGGCGTCTCACCGCAAGGCCAGGTCTGGTGGGCCGTGCCGACCCTG
 A  A  V  A  P  G  V  S  P  Q  G  Q  V  W  W  A  V  P  T  L 1870      1880      1890      1900      1910      1920
CTGCGCGACGACGATGCCGGAATGCTGAAGGGCTGGAGCTGGGACCAGGCCTTGTCTGAG
 L  R  D  D  D  A  G  M  L  K  G  W  S  W  D  Q  A  L  S  E
```

*FIG. 23D*

```
      1930        1940       1950       1960       1970       1980
GCCCTCTCGGTCGCGTCGCAGAACCTGACCGGGCGAAGCTGGGGCGAAGAGCATCGGCCC
 A  L  S  V  A  S  Q  N  L  T  G  R  S  W  G  E  E  H  R  P 1990        2000       2010       2020       2030       2040
CGCTTCACGCATCCGCTTGCCACGCAATTCCCGGCCTGGGCGGGGCTGCTGAATCCGGCT
 R  F  T  H  P  L  A  T  Q  F  P  A  W  A  G  L  L  N  P  A 2050        2060       2070       2080       2090       2100
TCCCGTCCGATCGGTGGCGATGGCGATACCGTGCTGGCGAACGGGCTCGTCCCGTCAGCC
 S  R  P  I  G  G  D  G  D  T  V  L  A  N  G  L  V  P  S  A 2110        2120       2130       2140       2150       2160
GGGCCGCAGGCGACCTATGGTGCCCTGTCGCGCTACGTCTTCGATGTCGGCAATTGGGAC
 G  P  Q  A  T  Y  G  A  L  S  R  Y  V  F  D  V  G  N  W  D 2170        2180       2190       2200       2210       2220
AATAGCCGCTGGGTCGTCTTCCACGGCGCCTCCGGGCATCCGGCCAGCGCCCATTATGCC
 N  S  R  W  V  V  F  H  G  A  S  G  H  P  A  S  A  H  Y  A 2230        2240       2250       2260       2270       2280
GATCAGAATGCGCCCTGGAGCGACTGTGCGATGGTGCCGATGCTCTATAGCTGGGACAGG
 D  Q  N  A  P  W  S  D  C  A  M  V  P  M  L  Y  S  W  D  R 2290        2300       2310       2320
ATCGCGGCAGAGGCCGTGACGTCGCAGGAACTCGTCCCGGCCTGA
 I  A  A  E  A  V  T  S  Q  E  L  V  P  A  *
```

*FIG. 23E*

```
        10        20        30        40        50        60
ATGACTATGGCAGCTAATACGGATCGCGCGGTCTTGCAGGCGGCGCTGCCGCCGCTTTCC
 M  T  M  A  A  N  T  D  R  A  V  L  Q  A  A  L  P  P  L  S 70        80        90       100       110       120
GGCAGCCTCCCCATTCCCGGATTGAGCGCGTCGGTCCGCGTCCGGCGCGATGCCTGGGGC
 G  S  L  P  I  P  G  L  S  A  S  V  R  V  R  R  D  A  W  G 130       140       150       160       170       180
ATCCCGCATATCAAGGCCTCGGGCGAGGCCGATGCCTATCGGGCGCTGGGCTTCGTCCAT
 I  P  H  I  K  A  S  G  E  A  D  A  Y  R  A  L  G  F  V  H 190       200       210       220       230       240
TCGCAGGACCGTCTTTTCCAGATGGAGCTGACGCGTCGCAAGGCGCTGGGACGCGCGGCC
 S  Q  D  R  L  F  Q  M  E  L  T  R  R  K  A  L  G  R  A  A 250       260       270       280       290       300
GAATGGCTGGGCGCCGAGGCCGCCGAGGCCGATATCCTCGTGCGCCGGCTCGGAATGGAA
 E  W  L  G  A  E  A  A  E  A  D  I  L  V  R  R  L  G  M  E 310       320       330       340       350       360
AAAGTCTGCCGGCGCGACTTCGAGGCCTTGGGCGTCGAGGCGAAGGACATGCTGCGGGCT
 K  V  C  R  R  D  F  E  A  L  G  V  E  A  K  D  M  L  R  A 370       380       390       400       410       420
TATGTCGCCGGCGTGAACGCATTCCTGGCTTCCGGTGCTCCCCTGCCTGTCGAATACGGA
 Y  V  A  G  V  N  A  F  L  A  S  G  A  P  L  P  V  E  Y  G 430       440       450       460       470       480
TTGCTCGGAGCAGAGCCGGAGCCCTGGGAGCCTTGGCACAGCATCGCGGTGATGCGCCGG
 L  L  G  A  E  P  E  P  W  E  P  W  H  S  I  A  V  M  R  R
```

*FIG. 24A*

```
        490       500       510       520       530       540
CTGGGCCTGCTTATGGGTTCGGTGTGGTTCAAGCTCTGGCGGATGCTGGCGCTGCCGGTG
 L  G  L  L  M  G  S  V  W  F  K  L  W  R  M  L  A  L  P  V 550       560       570       580       590       600
GTCGGAGCCGCGAATGCGCTGAAGCTGCGCTATGACGATGGCGGCCGGGATTTGCTCTGC
 V  G  A  A  N  A  L  K  L  R  Y  D  D  G  G  R  D  L  L  C 610       620       630       640       650       660
ATCCCGCCGGGCGCCGAAGCCGATCGGCTCGAGGCGGATCTCGCGACCCTGCGGCCCGCG
 I  P  P  G  A  E  A  D  R  L  E  A  D  L  A  T  L  R  P  A 670       680       690       700       710       720
GTCGATGCGCTGCTGAAGGCGATGGGCGGCGATGCCTCCGATGCTGCCGGCGGCGGCAGC
 V  D  A  L  L  K  A  M  G  G  D  A  S  D  A  A  G  G  G  S 730       740       750       760       770       780
AACAACTGGGCGGTCGCTCCGGGCCGCACGGCGACCGGCAGGCCGATCCTCGCGGGCGAT
 N  N  W  A  V  A  P  G  R  T  A  T  G  R  P  I  L  A  G  D 790       800       810       820       830       840
CCGCATCGCGTCTTCGAAATACCGGGCATCTATGCGCAGCATCATCTGGCCTGCGACCGG
 P  H  R  V  F  E  I  P  G  I  Y  A  Q  H  H  L  A  C  D  R 850       860       870       880       890       900
TTCGACATGATCGGCCTGACCGTGCCGGGCGTGCCGGGCTTCCCGCACTTCGCGCATAAC
 F  D  M  I  G  L  T  V  P  G  V  P  G  F  P  H  F  A  H  N 910       920       930       940       950       960
GGCAAGGTCGCCTATTGCGTCACCCATGCCTTCATGGACATCCACGATCTCTATCTCGAG
 G  K  V  A  Y  C  V  T  H  A  F  M  D  I  H  D  L  Y  L  E
```

*FIG. 24B*

```
        970       980       990      1000      1010      1020
CAGTTCGCGGGGGAGGGCCGCACTGCGCGGTTCGGCAACGATTTCGAGCCCGTCGCCTGG
 Q  F  A  G  E  G  R  T  A  R  F  G  N  D  F  E  P  V  A  W 1030      1040      1050      1060      1070      1080
AGCCGGGACCGTATCGCGGTCCGGGGTGGCGCCGATCGCGAGTTCGATATAGTCAAGACG
 S  R  D  R  I  A  V  R  G  G  A  D  R  E  F  D  I  V  K  T 1090      1100      1110      1120      1130      1140
CGCCATGGCCCGGTTATCGCGGGCGATCCGCGCGATGGCGCAGCGCTCACGCTGCGTTCG
 R  H  G  P  V  I  A  G  D  P  R  D  G  A  A  L  T  L  R  S 1150      1160      1170      1180      1190      1200
GTCCAGTTCGCCGAGACCGATCTGTCCTTCGACTGCCTGACGCGGATGCCGGGCGCATCG
 V  Q  F  A  E  T  D  L  S  F  D  C  L  T  R  M  P  G  A  S 1210      1220      1230      1240      1250      1260
ACCGTGGCCCAGCTCTACGACGCGACGCGCGGCTGGGGCCTGATCGACCATAACCTCGTC
 T  V  A  Q  L  Y  D  A  T  R  G  W  G  L  I  D  H  N  L  V 1270      1280      1290      1300      1310      1320
GCCGGGGATGTCGCGGGCTCGATCGGCCATCTGGTCCGCGCCCGCGTTCCGTCCCGTCCG
 A  G  D  V  A  G  S  I  G  H  L  V  R  A  R  V  P  S  R  P 1330      1340      1350      1360      1370      1380
CGCGAAAACGGCTGGCTGCCGGTGCCGGGCTGGTCCGGCGAGCATGAATGGCGGGGCTGG
 R  E  N  G  W  L  P  V  P  G  W  S  G  E  H  E  W  R  G  W 1390      1400      1410      1420      1430      1440
ATTCCGCACGAGGCGATGCCGCGCGTGATCGATCCGCCGGGCGGCATCATCGTCACGGCG
 I  P  H  E  A  M  P  R  V  I  D  P  P  G  G  I  I  V  T  A
```

*FIG. 24C*

```
      1450       1460       1470       1480       1490       1500
AATAATCGCGTCGTGGCCGATGACCATCCCGATTATCTCTGCACCGATTGCCATCCGCCC
 N  N  R  V  V  A  D  D  H  P  D  Y  L  C  T  D  C  H  P  P 1510       1520       1530       1540       1550       1560
TACCGCGCCGAGCGCATCATGAAGCGCCTGGTCGCCAATCCGGCTTTCGCCGTCGACGAT
 Y  R  A  E  R  I  M  K  R  L  V  A  N  P  A  F  A  V  D  D 1570       1580       1590       1600       1610       1620
GCCGCCGCGATCCATGCCGATACGCTGTCGCCCCATGTCGGGTTGCTGCGCCGGAGGCTC
 A  A  A  I  H  A  D  T  L  S  P  H  V  G  L  L  R  R  R  L 1630       1640       1650       1670       1680       1690
GAGGCGCTTGGAGCCCGCGACGACTCCGCGGCCGAAGGGCTGAGGCAGATGCTCGTCGCC
 E  A  L  G  A  R  D  D  S  A  A  E  G  L  R  Q  M  L  V  A 1690       1700       1710       1720       1730       1740
TGGGACGGCCGCATGGATGCGGCTTCGGAGGTCGCGTCTGCCTACAATGCGTTCCGCAGG
 W  D  G  R  M  D  A  A  S  E  V  A  S  A  Y  N  A  F  R  R 1750       1760       1770       1780       1790       1800
GCGCTGACGCGGCTGGTGACGGACCGCAGCGGGCTGGAGCAGGCGATATCGCATCCCTTC
 A  L  T  R  L  V  T  D  R  S  G  L  E  Q  A  I  S  H  P  F 1810       1820       1830       1840       1850       1860
GCGGCTGTCGCGCCGGGCGTCTCACCGCAAGGCCAGGTCTGGTGGGCCGTGCCGACCCTG
 A  A  V  A  P  G  V  S  P  Q  G  Q  V  W  W  A  V  P  T  L 1870       1880       1890       1900       1910       1920
CTGCGCGACGACGATGCCGGAATGCTGAAGGGCTGGAGCTGGGACCAGGCCTTGTCTGAG
 L  R  D  D  D  A  G  M  L  K  G  W  S  W  D  Q  A  L  S  E
```

*FIG. 24D*

```
     1930      1940      1950      1960      1970      1980
GCCCTCTCGGTCGCGTCGCAGAACCTGACCGGGCGAAGCTGGGGCGAAGAGCATCGGCCG
 A  L  S  V  A  S  Q  N  L  T  G  R  S  W  G  E  E  H  R  P 1990      2000      2010      2020      2030      2040
CGCTTCACGCATCCGCTTGCCACGCAATTCCCGGCCTGGGCGGGGCTGCTGAATCCGGCT
 R  F  T  H  P  L  A  T  Q  F  P  A  W  A  G  L  L  N  P  A 2050      2060      2070      2080      2080      2100
TCCCGTCCGATCGGTGGCGATGGCGATACCGTGCTGGCGAACGGGCTCGTCCCGTCAGCC
 S  R  P  I  G  G  D  G  D  T  V  L  A  N  G  L  V  P  S  A 2110      2120      2130      2140      2150      2160
GGGCCGCAGGCGACCTATGGTGCCCTGTCGCGCTACGTCTTCGATGTCGGCAATTGGGAC
 G  P  Q  A  T  Y  G  A  L  S  R  Y  V  F  D  V  G  N  W  D 2170      2180      2190      2200      2210      2220
AATAGCCGCTGGGTCGTCTTCCACGGCGCCTCCGGGCATCCGGCCAGCGCCCATTATGCC
 N  S  R  W  V  V  F  H  G  A  S  G  H  P  A  S  A  H  Y  A 2230      2240      2250      2260      2270      2280
GATCAGAATGCGCCCTGGAGCGACTGTGCGATGGTGCCGATGCTCTATAGCTGGGACAGG
 D  Q  N  A  P  W  S  D  C  A  M  V  P  M  L  Y  S  W  D  R 2290      2300      2310      2320
ATCGCGGCAGAGGCCGTGACGTCGCAGGAACTCGTCCCGGCCTGA
 I  A  A  E  A  V  T  S  Q  E  L  V  P  A  *
```

*FIG. 24E*

```
       10         20         30         40         50         60
ATGACTATGGCAGCTAATACGGATCGCGCGGTCTTGCAGGCGGCGCTGCCGCCGCTTTCC
 M  T  M  A  A  N  T  D  R  A  V  L  Q  A  A  L  P  P  L  S 70         80         90        100        110        120
GGCAGCCTCCCCATTCCCGGATTGAGCGCGTCGGTCCGCGTCCGGCGCGATGCCTGGGGC
 G  S  L  P  I  P  G  L  S  A  S  V  R  V  R  R  D  A  W  G 130        140        150        160        170        180
ATCCCGCATATCAAGGCCTCGGGCGAGGCCGATGCCTATCGGGCGCTGGGCTTCGTCCAT
 I  P  H  I  K  A  S  G  E  A  D  A  Y  R  A  L  G  F  V  H 190        200        210        220        230        240
TCGCAGGACCGTCTTTTCCAGATGGAGCTGACGCGTCGCAAGGCGCTGGGACGCGCGGCC
 S  Q  D  R  L  F  Q  M  E  L  T  R  R  K  A  L  G  R  A  A 250        260        270        280        290        300
GAATGGCTGGGCGCCGAGGCCGCCGAGGCCGATATCCTCGTGCGCCGGCTCGGAATGGAA
 E  W  L  G  A  E  A  A  E  A  D  I  L  V  R  R  L  G  M  E 310        320        330        340        350        360
AAAGTCTGCCGGCGCGACTTCGAGGCCTTGGGCGTCGAGGCGAAGGACATGCTGCGGGCT
 K  V  C  R  R  D  F  E  A  L  G  V  E  A  K  D  M  L  R  A 370        380        390        400        410        420
TATGTCGCCGGCGTGAACGCATTCCTGGCTTCCGGTGCTCCCCTGCCTGTCGAATACGGA
 Y  V  A  G  V  N  A  F  L  A  S  G  A  P  L  P  V  E  Y  G 430        440        450        460        470        480
TTGCTCGGAGCAGAGCCGGAGCCCTGGGAGCCTTGGCACAGCATCGCGGTGATGCGTCGA
 L  L  G  A  E  P  E  P  W  E  P  W  H  S  I  A  V  M  R  R
```

*FIG. 25A*

```
       490        500        510        520        530        540
CTCGGCCTGCTTCTGGGATCCGTGTGGTTCAAGCTCTGGCGGGCGCTAGCGCTGCCGGTG
 L  G  L  L  G  S  V  W  F  K  L  W  R  A  L  A  L  P  V 550        560        570        580        590        600
GTCGGAGCCGCGAATGCGCTGAAGCTGCGCTATGACGATGGCGGCCGGGATTTGCTCTGC
 V  G  A  A  N  A  L  K  L  R  Y  D  D  G  G  R  D  L  L  C 610        620        630        640        650        660
ATCCCGCCGGGCGCCGAAGCCGATCGGCTCGAGGCGGATCTCGCGACCCTGCGGCCCGCG
 I  P  P  G  A  E  A  D  R  L  E  A  D  L  A  T  L  R  P  A 670        680        690        700        710        720
GTCGATGCGCTGCTGAAGGCGATGGGCGGCGATGCCTCCGATGCTGCCGGCGGCGGCAGC
 V  D  A  L  L  K  A  M  G  G  D  A  S  D  A  A  G  G  G  S 730        740        750        760        770        780
AACAACTGGGCGGTCGCTCCGGGCCGCACGGCGACCGGCAGGCCGATCCTCGCGGGCGAT
 N  N  W  A  V  A  P  G  R  T  A  T  G  R  P  I  L  A  G  D 790        800        810        820        830        840
CCGCATCGCGTCTTCGAAATCCCTGGCTATTATGCGCAGCATCATCTGGCCTGCGACCGG
 P  H  R  V  F  E  I  P  G  Y  Y  A  Q  H  H  L  A  C  D  R 850        860        870        880        890        900
TTCGACATGATCGGCCTGACCGTGCCGGGCGTGCCGGGCTTCCCGCACTTCGCGCATAAC
 F  D  M  I  G  L  T  V  P  G  V  P  G  F  P  H  F  A  H  N 910        920        930        940        950        960
GGCAAGGTCGCCTATTGCGTCACCCATGCCTTCATGGACATCCACGATCTCTATCTCGAG
 G  K  V  A  Y  C  V  T  H  A  F  M  D  I  H  D  L  Y  L  E
```

*FIG. 25B*

```
       970        980        990       1000       1010       1020
CAGTTCGCGGGGGAGGGCCGCACTGCGCGGTTCGGCAACGATTTCGAGCCCGTCGCCTGG
 Q   F   A   G   E   G   R   T   A   R   F   G   N   D   F   E   P   V   A   W 1030       1040       1050       1060       1070       1080
AGCCGGGACCGTATCGCGGTCCGGGGTGGCGCCGATCGCGAGTTCGATATCGTCGAGACG
 S   R   D   R   I   A   V   R   G   G   A   D   R   E   F   D   I   V   E   T 1090       1100       1110       1120       1130       1140
CGCCATGGCCCGGTTATCGCGGGCGATCCGCGCGATGGCGCAGCGCTCACGCTGCGTTCG
 R   H   G   P   V   I   A   G   D   P   R   D   G   A   A   L   T   L   R   S 1150       1160       1170       1180       1190       1200
GTCCAGTTCGCCGAGACCGATCTGTCCTTCGACTGCCTGACGCGGATGCCGGGCGCATCG
 V   Q   F   A   E   T   D   L   S   F   D   C   L   T   R   M   P   G   A   S 1210       1220       1230       1240       1250       1260
ACCGTGGCCCAGCTCTACGACGCGACGCGCGGCTGGGGCCTGATCGACCATAACCTCGTC
 T   V   A   Q   L   Y   D   A   T   R   G   W   G   L   I   D   H   N   L   V 1270       1280       1290       1300       1310       1320
GCCGGGGATGTCGCGGGCTCGATCGGCCATCTGGTCCGCGCCCGCGTTCCGTCCCGTCCG
 A   G   D   V   A   G   S   I   G   H   L   V   R   A   R   V   P   S   R   P 1330       1340       1350       1360       1370       1380
CGCGAAAACGGCTGGCTGCCGGTGCCGGGCTGGTCCGGCGAGCATGAATGGCGGGGCTGG
 R   E   N   G   W   L   P   V   P   G   W   S   G   E   H   E   W   R   G   W 1390       1400       1410       1420       1430       1440
ATTCCGCACGAGGCGATGCCGCGCGTGATCGATCCGCCGGGCGGCATCATCGTCACGGCG
 I   P   H   E   A   M   P   R   V   I   D   P   P   G   G   I   I   V   T   A
```

*FIG.25C*

```
       1450      1460      1470      1480      1490      1500
AATAATCGCGTCGTGGCCGATGACCATCCCGATTATCTCTGCACCGATTGCCATCCGCCC
 N  N  R  V  V  A  D  D  H  P  D  Y  L  C  T  D  C  H  P  P 1510      1520      1530      1540      1550      1560
TACCGCGCCGAGCGCATCATGAAGCGCCTGGTCGCCAATCCGGCTTTCGCCGTCGACGAT
 Y  R  A  E  R  I  M  K  R  L  V  A  N  P  A  F  A  V  D  D 1570      1580      1590      1600      1610      1620
GCCGCCGCGATCCATGCCGATACGCTGTCGCCCCATGTCGGGTTGCTGCGCCGGAGGCTC
 A  A  A  I  H  A  D  T  L  S  P  H  V  G  L  L  R  R  R  L 1630      1640      1650      1660      1670      1680
GAGGCGCTTGGAGCCCGCGACGACTCCGCGGCCGAAGGGCTGAGGCAGATGCTCGTCGCC
 E  A  L  G  A  R  D  D  S  A  A  E  G  L  R  Q  M  L  V  A 1690      1700      1710      1720      1730      1740
TGGGACGGCCGCATGGATGCGGCTTCGGAGGTCGCGTCTGCCTACAATGCGTTCCGCAGG
 W  D  G  R  M  D  A  A  S  E  V  A  S  A  Y  N  A  F  R  R 1750      1760      1770      1780      1790      1800
GCGCTGACGCGGCTGGTGACGGACCGCAGCGGGCTGGAGCAGGCGATATCGCATCCCTTC
 A  L  T  R  L  V  T  D  R  S  G  L  E  Q  A  I  S  H  P  F 1810      1820      1830      1840      1850      1860
GCGGCTGTCGCGCCGGGCGTCTCACCGCAAGGCCAGGTCTGGTGGGCCGTGCCGACCCTG
 A  A  V  A  P  G  V  S  P  Q  G  Q  V  W  W  A  V  P  T  L 1870      1880      1890      1900      1910      1920
CTGCGCGACGACGATGCCGGAATGCTGAAGGGCTGGAGCTGGGACCAGGCCTTGTCTGAG
 L  R  D  D  D  A  G  M  L  K  G  W  S  W  D  Q  A  L  S  E
```

*FIG. 25D*

```
      1930       1940       1950       1960       1970       1980
GCCCTCTCGGTCGCGTCGCAGAACCTGACCGGGCGAAGCTGGGGCGAAGAGCATCGGCCG
 A  L  S  V  A  S  Q  N  L  T  G  R  S  W  G  E  E  H  R  P 1990       2000       2010       2020       2030       2040
CGCTTCACGCATCCGCTTGCCACGCAATTCCCGGCCTGGGCGGGGCTGCTGAATCCGGCT
 R  F  T  H  P  L  A  T  Q  F  P  A  W  A  G  L  L  N  P  A 2050       2060       2070       2080       2090       2100
TCCCGTCCGATCGGTGGCGATGGCGATACCGTGCTGGCGAACGGGCTCGTCCCGTCAGCC
 S  R  P  I  G  G  D  G  D  T  V  L  A  N  G  L  V  P  S  A 2110       2120       2130       2140       2150       2160
GGGCCGCAGGCGACCTATGGTGCCCTGTCGCGCTACGTCTTCGATGTCGGCAATTGGGAC
 G  P  Q  A  T  Y  G  A  L  S  R  Y  V  F  D  V  G  N  W  D 2170       2180       2190       2200       2210       2220
AATAGCCGCTGGGTCGTCTTCCACGGCGCCTCCGGGCATCCGGCCAGCGCCCATTATGCC
 N  S  R  W  V  V  F  H  G  A  S  G  H  P  A  S  A  H  Y  A 2230       2240       2250       2260       2270       2280
GATCAGAATGCGCCCTGGAGCGACTGTGCGATGGTGCCGATGCTCTATAGCTGGGACAGG
 D  Q  N  A  P  W  S  D  C  A  M  V  P  M  L  Y  S  W  D  R 2290       2300       2310       2320
ATCGCGGCAGAGGCCGTGACGTCGCAGGAACTCGTCCCGGCCTGA
 I  A  A  E  A  V  T  S  Q  E  L  V  P  A  *
```

*FIG. 25E*

```
         10        20        30        40        50        60
ATGACTATGGCAGCTAATACGGATCGCGCGGTCTTGCAGGCGGCGCTGCCGCCGCTTTCC
 M  T  M  A  A  N  T  D  R  A  V  L  Q  A  A  L  P  P  L  S 70        80        90       100       110       120
GGCAGCCTCCCCATTCCCGGATTGAGCGCGTCGGTCCGCGTCCGGCGCGATGCCTGGGGC
 G  S  L  P  I  P  G  L  S  A  S  V  R  V  R  R  D  A  W  G 130       140       150       160       170       180
ATCCCGCATATCAAGGCCTCGGGCGAGCTCGATGCCTATCGGGCGCTGGGCTTCGTCCAT
 I  P  H  I  K  A  S  G  E  L  D  A  Y  R  A  L  G  F  V  H 190       200       210       220       230       240
TCGCAGGACCGTCTTTTCCAGATGGAGCTGACGCGTCGCAAGGCGCTGGGACGCGCGGCC
 S  Q  D  R  L  F  Q  M  E  L  T  R  R  K  A  L  G  R  A  A 250       260       270       280       290       300
GAATGGCTGGGCGCCGAGGCCGCCGAGGCCGATATCCTCGTGCGCCGGCTCGGAATGGAA
 E  W  L  G  A  E  A  A  E  A  D  I  L  V  R  R  L  G  M  E 310       320       330       340       350       360
AAAGTCTGCCGGCGCGACTTCGAGGCCTTGGGCGTCGAGGCGAAGGACATGCTGCGGGCT
 K  V  C  R  R  D  F  E  A  L  G  V  E  A  K  D  M  L  R  A 370       380       390       400       410       420
TATGTCGCCGGCGTGAACGCATTCCTGGCTTCCGGTGCTCCCCTGCCTGTCGAATACGGA
 Y  V  A  G  V  N  A  F  L  A  S  G  A  P  L  P  V  E  Y  G 430       440       450       460       470       480
TTGCTCGGAGCAGAGCCGGAGCCCTGGGAGCCTTGGCACAGCATCGCGGTGATGCGCCGG
 L  L  G  A  E  P  E  P  W  E  P  W  H  S  I  A  V  M  R  R
```

*FIG. 26A*

```
         490        500        510        520        530        540
CTGGGCCTGCTTATGGGTTCGGTGTGGTTCAAGCTCTGGCGGATGCTGGCGCTGCCGGTG
 L   G   L   L   M   G   S   V   W   F   K   L   W   R   M   L   A   L   P   V 550        560        570        580        590        600
GTCGGAGCCGCGAATGCGCTGAAGCTGCGCTATGACGATGGCGGCCGGGATTTGCTCTGC
 V   G   A   A   N   A   L   K   L   R   Y   D   D   G   G   R   D   L   L   C 610        620        630        640        650        660
ATCCCGCCGGGCGCCGAAGCCGATCGGCTCGAGGCGGATCTCGCGACCCTGCGGCCCGCG
 I   P   P   G   A   E   A   D   R   L   E   A   D   L   A   T   L   R   P   A 670        680        690        700        710        720
GTCGATGCGCTGCTGAAGGCGATGGGCGGCGATGCCTCCGATGCTGCCGGCGGCGGCAGC
 V   D   A   L   L   K   A   M   G   G   D   A   S   D   A   A   G   G   G   S 730        740        750        760        770        780
AACAACTGGGCGGTCGCTCCGGGCCGCACGGCGACCGGCAGGCCGATCCTCGCGGGCGAT
 N   N   W   A   V   A   P   G   R   T   A   T   G   R   P   I   L   A   G   D 790        800        810        820        830        840
CCGCATCGCGTCTTCGAAATCCCGGGCATGTATGCGCAGCATCATCTGGCCTGCGACCGG
 P   H   R   V   F   E   I   P   G   M   Y   A   Q   H   H   L   A   C   D   R 850        860        870        880        890        900
TTCGACATGATCGGCCTGACCGTGCCGGGCGTGCCGGGCTTCCCGCACTTCGCGCATAAC
 F   D   M   I   G   L   T   V   P   G   V   P   G   F   P   H   F   A   H   N 910        920        930        940        950        960
GGCAAGGTCGCCTATTGCGTCACCCATGCCTTCATGGACATCCACGATCTCTATCTCGAG
 G   K   V   A   Y   C   V   T   H   A   F   M   D   I   H   D   L   Y   L   E
```

*FIG. 26B*

```
      970       980       990      1000      1010      1020
CAGTTCGCGGGGGAGGGCCGCACTGCGCGGTTCGGCAACGATTTCGAGCCCGTCGCCTGG
 Q  F  A  G  E  G  R  T  A  R  F  G  N  D  F  E  P  V  A  W 1030      1040      1050      1060      1070      1080
AGCCGGGACCGTATCGCGGTCCGGGGTGGCGCCGATCGCGAGTTCGATATCGTCGAGACG
 S  R  D  R  I  A  V  R  G  G  A  D  R  E  F  D  I  V  E  T 1090      1100      1110      1120      1130      1140
CGCCATGGCCCGGTTATCGCGGGCGATCCGCGCGATGGCGCAGCGCTCACGCTGCGTTCG
 R  H  G  P  V  I  A  G  D  P  R  D  G  A  A  L  T  L  R  S 1150      1160      1170      1180      1190      1200
GTCCAGTTCGCCGAGACCGATCTGTCCTTCGACTGCCTGACGCGGATGCCGGGCGCATCG
 V  Q  F  A  E  T  D  L  S  F  D  C  L  T  R  M  P  G  A  S 1210      1220      1230      1240      1250      1260
ACCGTGGCCCAGCTCTACGACGCGACGCGCGGCTGGGGCCTGATCGACCATAACCTCGTC
 T  V  A  Q  L  Y  D  A  T  R  G  W  G  L  I  D  H  N  L  V 1270      1280      1290      1300      1310      1320
GCCGGGGATGTCGCGGGCTCGATCGGCCATCTGGTCCGCGCCCGCGTTCCGTCCCGTCCG
 A  G  D  V  A  G  S  I  G  H  L  V  R  A  R  V  P  S  R  P 1330      1340      1350      1360      1370      1380
CGCGAAAACGGCTGGCTGCCGGTGCCGGGCTGGTCCGGCGAGCATGAATGGCGGGGCTGG
 R  E  N  G  W  L  P  V  P  G  W  S  G  E  H  E  W  R  G  W 1390      1400      1410      1420      1430      1440
ATTCCGCACGAGGCGATGCCGCGCGTGATCGATCCGCCGGGCGGCATCATCGTCACGGCG
 I  P  H  E  A  M  P  R  V  I  D  P  P  G  G  I  I  V  T  A
```

*FIG. 26C*

```
       1450      1460      1470      1480      1490      1500
AATAATCGCGTCGTGGCCGATGACCATCCCGATTATCTCTGCACCGATTGCCATCCGCCC
 N  N  R  V  V  A  D  D  H  P  D  Y  L  C  T  D  C  H  P  P 1510      1520      1530      1540      1550      1560
TACCGCGCCGAGCGCATCATGAAGCGCCTGGTCGCCAATCCGGCTTTCGCCGTCGACGAT
 Y  R  A  E  R  I  M  K  R  L  V  A  N  P  A  F  A  V  D  D 1570      1580      1590      1600      1610      1620
GCCGCCGCGATCCATGCCGATACGCTGTCGCCCCATGTCGGGTTGCTGCGCCGGAGGCTC
 A  A  A  I  H  A  D  T  L  S  P  H  V  G  L  L  R  R  R  L 1630      1640      1650      1660      1670      1680
GAGGCGCTTGGAGCCCGCGACGACTCCGCGGCCGAAGGGCTGAGGCAGATGCTCGTCGCC
 E  A  L  G  A  R  D  D  S  A  A  E  G  L  R  Q  M  L  V  A 1690      1700      1710      1720      1730      1740
TGGGACGGCCGCATGGATGCGGCTTCGGAGGTCGCGTCTGCCTACAATGCGTTCCGCAGG
 W  D  G  R  M  D  A  A  S  E  V  A  S  A  Y  N  A  F  R  R 1750      1760      1770      1780      1790      1800
GCGCTGACGCGGCTGGTGACGGACCGCAGCGGGCTGGAGCAGGCGATATCGCATCCCTTC
 A  L  T  R  L  V  T  D  R  S  G  L  E  Q  A  I  S  H  P  F 1810      1820      1830      1840      1850      1860
GCGGCTGTCGCGCCGGGCGTCTCACCGCAAGGCCAGGTCTGGTGGGCCGTGCCGACCCTG
 A  A  V  A  P  G  V  S  P  Q  G  Q  V  W  W  A  V  P  T  L 1870      1880      1890      1900      1910      1920
CTGCGCGACGACGATGCCGGAATGCTGAAGGGCTGGAGCTGGGACCAGGCCTTGTCTGAG
 L  R  D  D  D  A  G  M  L  K  G  W  S  W  D  Q  A  L  S  E
```

FIG. 26D

```
      1930      1940      1950      1960      1970      1980
GCCCTCTCGGTCGCGTCGCAGAACCTGACCGGGCGAAGCTGGGGCGAAGAGCATCGGCCG
 A  L  S  V  A  S  Q  N  L  T  G  R  S  W  G  E  E  H  R  P 1990      2000      2010      2020      2030      2040
CGCTTCACGCATCCGCTTGCCACGCAATTCCCGGCCTGGGCGGGGCTGCTGAATCCGGCT
 R  F  T  H  P  L  A  T  Q  F  P  A  W  A  G  L  L  N  P  A 2050      2060      2070      2080      2090      2100
TCCCGTCCGATCGGTGGCGATGGCGATACCGTGCTGGCGAACGGGCTCGTCCCGTCAGCC
 S  R  P  I  G  G  D  G  D  T  V  L  A  N  G  L  V  P  S  A 2110      2120      2130      2140      2150      2160
GGGCCGCAGGCGACCTATGGTGCCCTGTCGCGCTACGTCTTCGATGTCGGCAATTGGGAC
 G  P  Q  A  T  Y  G  A  L  S  R  Y  V  F  D  V  G  N  W  D 2170      2180      2190      2200      2210      2220
AATAGCCGCTGGGTCGTCTTCCACGGCGCCTCCGGGCATCCGGCCAGCGCCCATTATGCC
 N  S  R  W  V  V  F  H  G  A  S  G  H  P  A  S  A  H  Y  A 2230      2240      2250      2260      2270      2280
GATCAGAATGCGCCCTGGAGCGACTGTGCGATGGTGCCGATGCTCTATAGCTGGGACAGG
 D  Q  N  A  P  W  S  D  C  A  M  V  P  M  L  Y  S  W  D  R 2290      2300      2310      2320
ATCGCGGCAGAGGCCGTGACGTCGCAGGAACTCGTCCCGGCCTGA
 I  A  A  E  A  V  T  S  Q  E  L  V  P  A  *
```

*FIG. 26E*

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly Leu Leu Ala Gly Ser Val Trp Phe
    1                      5

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

GGGCCTGCTT GCGGGATCCG TGTGGTTCA    29

-continued (2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Leu Trp Arg Ala Leu Ala Leu Pro
1                   5

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GCTCTGGCGG GCGCTAGCGC TGCCGG        26

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

His Glu Ala Ala Pro Arg Val Ile
1                   5

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GCACGAGGCG GCGCCACGCG TGATCG        26

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Glu Arg Ile Ala Lys Arg Leu Val Ala
1                   5

(2) INFORMATION FOR SEQ ID NO:8:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:8:

GAGCGCATCG CGAAGCGCTT GGTCGCCA    28

(2) INFORMATION FOR SEQ ID NO:9:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Asp Cys Ala Ala Val Pro Met Leu
  1               5

(2) INFORMATION FOR SEQ ID NO:10:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:10:

CGACTGTGCG GCGGTACCGA TGCTCT    26

(2) INFORMATION FOR SEQ ID NO:11:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Ala Ser Gly Glu Leu Asp Ala Tyr Arg
  1               5

(2) INFORMATION FOR SEQ ID NO:12:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:12:

GCCTCGGGCG AGCTCGATGC CTATCGG    27

(2) INFORMATION FOR SEQ ID NO:13:

(i) SEQUENCE CHARACTERISTICS:
    (A) LENGTH: 36 base pairs
    (B) TYPE: nucleic acid (C) STRANDEDNESS: single
      (D) TOPOLOGY: linear (i i) MOLECULE TYPE: other nucleic acid (x i) SEQUENCE DESCRIPTION: SEQ ID NO:13:

CATCCGCCAA AGCTTGAACC ACACCGCACC CATAAG 36

(2) INFORMATION FOR SEQ ID NO:14:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:14:

Met  Glu  Leu  Thr  Arg  Arg  Lys  Ala  Leu  Gly  Arg
1                  5                        10

(2) INFORMATION FOR SEQ ID NO:15:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (i i) MOLECULE TYPE: other nucleic acid (x i) SEQUENCE DESCRIPTION: SEQ ID NO:15:

ATGGAGCTGA CGCGTCGCAA AGCGCTGGGA CG 32

(2) INFORMATION FOR SEQ ID NO:16:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:16:

Val  Met  Arg  Arg  Leu  Gly  Leu  Leu  Cys  Gly  Ser  Val
1                  5                        10

(2) INFORMATION FOR SEQ ID NO:17:

(i) SEQUENCE CHARACTERISTICS:
      (A) LENGTH: 38 base pairs
      (B) TYPE: nucleic acid
      (C) STRANDEDNESS: double
      (D) TOPOLOGY: linear (i i) MOLECULE TYPE: other nucleic acid (x i) SEQUENCE DESCRIPTION: SEQ ID NO:17:

CGGTGATGCG TCGACTCGGC CTGCTTTGCG GATCCGTG 38

(2) INFORMATION FOR SEQ ID NO:18:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (i i) MOLECULE TYPE: other nucleic acid (x i) SEQUENCE DESCRIPTION: SEQ ID NO:18:

CACGGATCCA TCAAGCAGGC CGAGTCGACG CATCACCG    38

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (i i) MOLECULE TYPE: other nucleic acid (x i) SEQUENCE DESCRIPTION: SEQ ID NO:19:

CACGGATCCT TCAAGCAGGC CGAGTCGACG CATCACCG    38

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:20:

CACGGATCCG AAAAGCAGGC CGAGTCGACG CATCACCG    38

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:21:

CACGGATCCG CCAAGCAGGC CGAGTCGACG CATCACCG    38

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:22:

CACGGATCCA TGAAGCAGGC CGAGTCGACG CATCACCG    38

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:23:

CACGGATCCG ATAAGCAGGC CGAGTCGACG CATCACCG    38

( 2 ) INFORMATION FOR SEQ ID NO:24:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:24:

CACGGATCCC TTAAGCAGGC CGAGTCGACG CATCACCG        38

( 2 ) INFORMATION FOR SEQ ID NO:25:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:25:

CACGGATCCC AGAAGCAGGC CGAGTCGACG CATCACCG        38

( 2 ) INFORMATION FOR SEQ ID NO:26:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:26:

CACGGATCCG TTAAGCAGGC CGAGTCGACG CATCACCG        38

( 2 ) INFORMATION FOR SEQ ID NO:27:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:27:

CACGGATCCC GGAAGCAGGC CGAGTCGACG CATCACCG        38

( 2 ) INFORMATION FOR SEQ ID NO:28:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:28:

CACGGATCCC TGAAGCAGGC CGAGTCGACG CATCACCG        38

( 2 ) INFORMATION FOR SEQ ID NO:29:

( i ) SEQUENCE CHARACTERISTICS:

(A) LENGTH: 38 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:29:

CACGGATCCA CGAAGCAGGC CGAGTCGACG CATCACCG    38

(2) INFORMATION FOR SEQ ID NO:30:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:30:

CACGGATCCC GAAAGCAGGC CGAGTCGACG CATCACCG    38

(2) INFORMATION FOR SEQ ID NO:31:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:31:

CACGGATCCC GTAAGCAGGC CGAGTCGACG CATCACCG    38

(2) INFORMATION FOR SEQ ID NO:32:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:32:

CACGGATCCC ACAAGCAGGC CGAGTCGACG CATCACCG    38

(2) INFORMATION FOR SEQ ID NO:33:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:33:

CACGGATCCC CAAAGCAGGC CGAGTCGACG CATCACCG    38

(2) INFORMATION FOR SEQ ID NO:34:

(i) SEQUENCE CHARACTERISTICS:
(A) LENGTH: 38 base pairs
(B) TYPE: nucleic acid
(C) STRANDEDNESS: single
(D) TOPOLOGY: linear ( i i ) MOLECULE TYPE: other nucleic acid ( x i ) SEQUENCE DESCRIPTION: SEQ ID NO:34:

CACGGATCCC ACAAGCAGGC CGAGTCGACG CATCACCG     38

( 2 ) INFORMATION FOR SEQ ID NO:35:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

Arg Val Phe Glu Ile Pro Gly Ile
1               5

( 2 ) INFORMATION FOR SEQ ID NO:36:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:36:

CACGGATCCA TAAAGCAGGC CGAGTCGACG CATCACCG     38

( 2 ) INFORMATION FOR SEQ ID NO:37:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Phe Asp Ile Val Lys Thr Arg His Gly Pro Val
1               5                       10

( 2 ) INFORMATION FOR SEQ ID NO:38:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:38:

TCAAGCTATA TCAGTTCTGC GCGGTACCGG GCCAAT       36

( 2 ) INFORMATION FOR SEQ ID NO:39:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:39:

TAACCGGGCC ATGGCGCGTC AGGACTATAT CGAACT     36

( 2 ) INFORMATION FOR SEQ ID NO:40:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:40:

TAACCGGGCC ATGGCGCGTG CGGACTATAT CGAACT     36

( 2 ) INFORMATION FOR SEQ ID NO:41:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:41:

TAACCGGGCC ATGGCGCGTC GAGACTATAT CGAACT     36

( 2 ) INFORMATION FOR SEQ ID NO:42:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:42:

TAACCGGGCC ATGGCGCGTG GTGACTATAT CGAACT     36

( 2 ) INFORMATION FOR SEQ ID NO:43:

( i ) SEQUENCE CHARACTERISTICS:
        ( A ) LENGTH: 2325 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2325

( i x ) FEATURE:
        ( A ) NAME/KEY: mat_peptide
        ( B ) LOCATION: 4..2322

( x i ) SEQUENCE DESCRIPTION: SEQ ID NO:43:

```
ATG  ACT  ATG  GCA  GCT  AAT  ACG  GAT  CGC  GCG  GTC  TTG  CAG  GCG  GCG  CTG        48
Met  Thr  Met  Ala  Ala  Asn  Thr  Asp  Arg  Ala  Val  Leu  Gln  Ala  Ala  Leu
 -1    1                  5                      10                      15

CCG  CCG  CTT  TCC  GGC  AGC  CTC  CCC  ATT  CCC  GGA  TTG  AGC  GCG  TCG  GTC        96
Pro  Pro  Leu  Ser  Gly  Ser  Leu  Pro  Ile  Pro  Gly  Leu  Ser  Ala  Ser  Val
                    20                      25                      30

CGC  GTC  CGG  CGC  GAT  GCC  TGG  GGC  ATC  CCG  CAT  ATC  AAG  GCC  TCG  GGC       144
Arg  Val  Arg  Arg  Asp  Ala  Trp  Gly  Ile  Pro  His  Ile  Lys  Ala  Ser  Gly
               35                      40                      45
```

```
GAG  GCC  GAT  GCC  TAT  CGG  GCG  CTG  GGC  TTC  GTC  CAT  TCG  CAG  GAC  CGT      192
Glu  Ala  Asp  Ala  Tyr  Arg  Ala  Leu  Gly  Phe  Val  His  Ser  Gln  Asp  Arg
              50                  55                  60

CTT  TTC  CAG  ATG  GAG  CTG  ACG  CGT  CGC  AAG  GCG  CTG  GGA  CGC  GCG  GCC      240
Leu  Phe  Gln  Met  Glu  Leu  Thr  Arg  Arg  Lys  Ala  Leu  Gly  Arg  Ala  Ala
          65                  70                  75

GAA  TGG  CTG  GGC  GCC  GAG  GCC  GCC  GAG  GCC  GAT  ATC  CTC  GTG  CGC  CGG      288
Glu  Trp  Leu  Gly  Ala  Glu  Ala  Ala  Glu  Ala  Asp  Ile  Leu  Val  Arg  Arg
     80                  85                  90                              95

CTC  GGA  ATG  GAA  AAA  GTC  TGC  CGG  CGC  GAC  TTC  GAG  GCC  TTG  GGC  GTC      336
Leu  Gly  Met  Glu  Lys  Val  Cys  Arg  Arg  Asp  Phe  Glu  Ala  Leu  Gly  Val
                         100                 105                      110

GAG  GCG  AAG  GAC  ATG  CTG  CGG  GCT  TAT  GTC  GCC  GGC  GTG  AAC  GCA  TTC      384
Glu  Ala  Lys  Asp  Met  Leu  Arg  Ala  Tyr  Val  Ala  Gly  Val  Asn  Ala  Phe
                    115                 120                      125

CTG  GCT  TCC  GGT  GCT  CCC  CTG  CCT  GTC  GAA  TAC  GGA  TTG  CTC  GGA  GCA      432
Leu  Ala  Ser  Gly  Ala  Pro  Leu  Pro  Val  Glu  Tyr  Gly  Leu  Leu  Gly  Ala
               130                 135                      140

GAG  CCG  GAG  CCC  TGG  GAG  CCT  TGG  CAC  AGC  ATC  GCG  GTG  ATG  CGC  CGG      480
Glu  Pro  Glu  Pro  Trp  Glu  Pro  Trp  His  Ser  Ile  Ala  Val  Met  Arg  Arg
145                      150                      155

CTG  GGC  CTG  CTT  GCG  GGA  TCC  GTG  TGG  TTC  AAG  CTC  TGG  CGG  ATG  CTG      528
Leu  Gly  Leu  Leu  Ala  Gly  Ser  Val  Trp  Phe  Lys  Leu  Trp  Arg  Met  Leu
160                      165                      170                      175

GCG  CTG  CCG  GTG  GTC  GGA  GCC  GCG  AAT  GCG  CTG  AAG  CTG  CGC  TAT  GAC      576
Ala  Leu  Pro  Val  Val  Gly  Ala  Ala  Asn  Ala  Leu  Lys  Leu  Arg  Tyr  Asp
                    180                      185                      190

GAT  GGC  GGC  CGG  GAT  TTG  CTC  TGC  ATC  CCG  CCG  GGC  GCC  GAA  GCC  GAT      624
Asp  Gly  Gly  Arg  Asp  Leu  Leu  Cys  Ile  Pro  Pro  Gly  Ala  Glu  Ala  Asp
               195                 200                      205

CGG  CTC  GAG  GCG  GAT  CTC  GCG  ACC  CTG  CGG  CCC  GCG  GTC  GAT  GCG  CTG      672
Arg  Leu  Glu  Ala  Asp  Leu  Ala  Thr  Leu  Arg  Pro  Ala  Val  Asp  Ala  Leu
          210                 215                      220

CTG  AAG  GCG  ATG  GGC  GGC  GAT  GCC  TCC  GAT  GCT  GCC  GGC  GGC  GGC  AGC      720
Leu  Lys  Ala  Met  Gly  Gly  Asp  Ala  Ser  Asp  Ala  Ala  Gly  Gly  Gly  Ser
     225                 230                      235

AAC  AAC  TGG  GCG  GTC  GCT  CCG  GGC  CGC  ACG  GCG  ACC  GGC  AGG  CCG  ATC      768
Asn  Asn  Trp  Ala  Val  Ala  Pro  Gly  Arg  Thr  Ala  Thr  Gly  Arg  Pro  Ile
240                      245                      250                      255

CTC  GCG  GGC  GAT  CCG  CAT  CGC  GTC  TTC  GAA  ATC  CCG  GGC  ATG  TAT  GCG      816
Leu  Ala  Gly  Asp  Pro  His  Arg  Val  Phe  Glu  Ile  Pro  Gly  Met  Tyr  Ala
                    260                      265                      270

CAG  CAT  CAT  CTG  GCC  TGC  GAC  CGG  TTC  GAC  ATG  ATC  GGC  CTG  ACC  GTG      864
Gln  His  His  Leu  Ala  Cys  Asp  Arg  Phe  Asp  Met  Ile  Gly  Leu  Thr  Val
               275                 280                      285

CCG  GGC  GTG  CCG  GGC  TTC  CCG  CAC  TTC  GCG  CAT  AAC  GGC  AAG  GTC  GCC      912
Pro  Gly  Val  Pro  Gly  Phe  Pro  His  Phe  Ala  His  Asn  Gly  Lys  Val  Ala
          290                 295                      300

TAT  TGC  GTC  ACC  CAT  GCC  TTC  ATG  GAC  ATC  CAC  GAT  CTC  TAT  CTC  GAG      960
Tyr  Cys  Val  Thr  His  Ala  Phe  Met  Asp  Ile  His  Asp  Leu  Tyr  Leu  Glu
     305                 310                      315

CAG  TTC  GCG  GGG  GAG  GGC  CGC  ACT  GCG  CGG  TTC  GGC  AAC  GAT  TTC  GAG     1008
Gln  Phe  Ala  Gly  Glu  Gly  Arg  Thr  Ala  Arg  Phe  Gly  Asn  Asp  Phe  Glu
320                      325                      330                      335

CCC  GTC  GCC  TGG  AGC  CGG  GAC  CGT  ATC  GCG  GTC  CGG  GGT  GGC  GCC  GAT     1056
Pro  Val  Ala  Trp  Ser  Arg  Asp  Arg  Ile  Ala  Val  Arg  Gly  Gly  Ala  Asp
                    340                      345                      350

CGC  GAG  TTC  GAT  ATC  GTC  GAG  ACG  CGC  CAT  GGC  CCG  GTT  ATC  GCG  GGC     1104
Arg  Glu  Phe  Asp  Ile  Val  Glu  Thr  Arg  His  Gly  Pro  Val  Ile  Ala  Gly
               355                 360                      365
```

| | | | | | | | | | | | | | | | | |
|---|---|---|---|---|---|---|---|---|---|---|---|---|---|---|---|---|
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | | 370 | | | | | 375 | | | | | 380 | | | | |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| 385 | | | | | 390 | | | | | 395 | | | | | | |
| ACC | GTG | GCC | CAG | CTC | TAC | GAC | GCG | ACG | CGC | GGC | TGG | GGC | CTG | ATC | GAC | 1248 |
| Thr | Val | Ala | Gln | Leu | Tyr | Asp | Ala | Thr | Arg | Gly | Trp | Gly | Leu | Ile | Asp | |
| 400 | | | | | 405 | | | | | 410 | | | | | 415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala | Gly | Asp | Val | Ala | Gly | Ser | Ile | Gly | His | Leu | Val | |
| | | | | 420 | | | | | 425 | | | | | 430 | | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val | |
| | | | 435 | | | | | 440 | | | | | 445 | | | |
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | | | 450 | | | | | 455 | | | | | 460 | | | |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala | |
| | 465 | | | | | 470 | | | | | 475 | | | | | |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | | 500 | | | | | 505 | | | | | 510 | | |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr | |
| | | | 515 | | | | | 520 | | | | | 525 | | | |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly | |
| | | 530 | | | | | 535 | | | | | 540 | | | | |
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala | |
| | 545 | | | | | 550 | | | | | 555 | | | | | |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | | 630 | | | | | 635 | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |

| | | | | | | | | | | | | | | | | |
|---|---|---|---|---|---|---|---|---|---|---|---|---|---|---|---|---|
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | 690 | | | | | 695 | | | | | 700 | | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| 705 | | | | | 710 | | | | | 715 | | | | | | |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | | 725 | | | | | 730 | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | 755 | | | | | 760 | | | | | 765 | | | |
| CAG | GAA | CTC | GTC | CCG | GCC | TGA | | | | | | | | | | 2325 |
| Gln | Glu | Leu | Val | Pro | Ala | * | | | | | | | | | | |
| | | 770 | | | | | | | | | | | | | | |

( 2 ) INFORMATION FOR SEQ ID NO:44:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| | | | | | | | | | | | | | | |
|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| -1 | 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | | 20 | | | | | 25 | | | | | 30 | |
| Arg | Val | Arg | Arg | Asp | Ala | Trp | Gly | Ile | Pro | His | Ile | Lys | Ala | Ser | Gly |
| | | | 35 | | | | | 40 | | | | | 45 | | |
| Glu | Ala | Asp | Ala | Tyr | Arg | Ala | Leu | Gly | Phe | Val | His | Ser | Gln | Asp | Arg |
| | | 50 | | | | | 55 | | | | | 60 | | | |
| Leu | Phe | Gln | Met | Glu | Leu | Thr | Arg | Arg | Lys | Ala | Leu | Gly | Arg | Ala | Ala |
| 65 | | | | | 70 | | | | | 75 | | | | | |
| Glu | Trp | Leu | Gly | Ala | Glu | Ala | Ala | Glu | Ala | Asp | Ile | Leu | Val | Arg | Arg |
| 80 | | | | | 85 | | | | | 90 | | | | | 95 |
| Leu | Gly | Met | Glu | Lys | Val | Cys | Arg | Arg | Asp | Phe | Glu | Ala | Leu | Gly | Val |
| | | | | 100 | | | | | 105 | | | | | 110 | |
| Glu | Ala | Lys | Asp | Met | Leu | Arg | Ala | Tyr | Val | Ala | Gly | Val | Asn | Ala | Phe |
| | | | 115 | | | | | 120 | | | | | 125 | | |
| Leu | Ala | Ser | Gly | Ala | Pro | Leu | Pro | Val | Glu | Tyr | Gly | Leu | Leu | Gly | Ala |
| | | 130 | | | | | 135 | | | | | 140 | | | |
| Glu | Pro | Glu | Pro | Trp | Glu | Pro | Trp | His | Ser | Ile | Ala | Val | Met | Arg | Arg |
| | 145 | | | | | 150 | | | | | 155 | | | | |
| Leu | Gly | Leu | Leu | Ala | Gly | Ser | Val | Trp | Phe | Lys | Leu | Trp | Arg | Met | Leu |
| 160 | | | | | 165 | | | | | 170 | | | | | 175 |
| Ala | Leu | Pro | Val | Val | Gly | Ala | Ala | Asn | Ala | Leu | Lys | Leu | Arg | Tyr | Asp |
| | | | | 180 | | | | | 185 | | | | | 190 | |
| Asp | Gly | Gly | Arg | Asp | Leu | Leu | Cys | Ile | Pro | Pro | Gly | Ala | Glu | Ala | Asp |
| | | | 195 | | | | | 200 | | | | | 205 | | |
| Arg | Leu | Glu | Ala | Asp | Leu | Ala | Thr | Leu | Arg | Pro | Ala | Val | Asp | Ala | Leu |
| | | 210 | | | | | 215 | | | | | 220 | | | |

-continued

```
Leu  Lys  Ala  Met  Gly  Gly  Asp  Ala  Ser  Asp  Ala  Ala  Gly  Gly  Gly  Ser
     225                 230                 235
Asn  Asn  Trp  Ala  Val  Ala  Pro  Gly  Arg  Thr  Ala  Thr  Gly  Arg  Pro  Ile
240                 245                 250                 255
Leu  Ala  Gly  Asp  Pro  His  Arg  Val  Phe  Glu  Ile  Pro  Gly  Met  Tyr  Ala
               260                 265                 270
Gln  His  His  Leu  Ala  Cys  Asp  Arg  Phe  Asp  Met  Ile  Gly  Leu  Thr  Val
               275                 280                 285
Pro  Gly  Val  Pro  Gly  Phe  Pro  His  Phe  Ala  His  Asn  Gly  Lys  Val  Ala
               290                 295                 300
Tyr  Cys  Val  Thr  His  Ala  Phe  Met  Asp  Ile  His  Asp  Leu  Tyr  Leu  Glu
     305                 310                 315
Gln  Phe  Ala  Gly  Glu  Gly  Arg  Thr  Ala  Arg  Phe  Gly  Asn  Asp  Phe  Glu
320                 325                 330                 335
Pro  Val  Ala  Trp  Ser  Arg  Asp  Arg  Ile  Ala  Val  Arg  Gly  Gly  Ala  Asp
               340                 345                 350
Arg  Glu  Phe  Asp  Ile  Val  Glu  Thr  Arg  His  Gly  Pro  Val  Ile  Ala  Gly
               355                 360                 365
Asp  Pro  Arg  Asp  Gly  Ala  Ala  Leu  Thr  Leu  Arg  Ser  Val  Gln  Phe  Ala
               370                 375                 380
Glu  Thr  Asp  Leu  Ser  Phe  Asp  Cys  Leu  Thr  Arg  Met  Pro  Gly  Ala  Ser
     385                 390                 395
Thr  Val  Ala  Gln  Leu  Tyr  Asp  Ala  Thr  Arg  Gly  Trp  Gly  Leu  Ile  Asp
400                 405                 410                 415
His  Asn  Leu  Val  Ala  Gly  Asp  Val  Ala  Gly  Ser  Ile  Gly  His  Leu  Val
               420                 425                 430
Arg  Ala  Arg  Val  Pro  Ser  Arg  Pro  Arg  Glu  Asn  Gly  Trp  Leu  Pro  Val
               435                 440                 445
Pro  Gly  Trp  Ser  Gly  Glu  His  Glu  Trp  Arg  Gly  Trp  Ile  Pro  His  Glu
               450                 455                 460
Ala  Met  Pro  Arg  Val  Ile  Asp  Pro  Pro  Gly  Gly  Ile  Ile  Val  Thr  Ala
     465                 470                 475
Asn  Asn  Arg  Val  Val  Ala  Asp  Asp  His  Pro  Asp  Tyr  Leu  Cys  Thr  Asp
480                 485                 490                 495
Cys  His  Pro  Pro  Tyr  Arg  Ala  Glu  Arg  Ile  Met  Lys  Arg  Leu  Val  Ala
               500                 505                 510
Asn  Pro  Ala  Phe  Ala  Val  Asp  Asp  Ala  Ala  Ala  Ile  His  Ala  Asp  Thr
               515                 520                 525
Leu  Ser  Pro  His  Val  Gly  Leu  Leu  Arg  Arg  Arg  Leu  Glu  Ala  Leu  Gly
               530                 535                 540
Ala  Arg  Asp  Asp  Ser  Ala  Ala  Glu  Gly  Leu  Arg  Gln  Met  Leu  Val  Ala
     545                 550                 555
Trp  Asp  Gly  Arg  Met  Asp  Ala  Ala  Ser  Glu  Val  Ala  Ser  Ala  Tyr  Asn
560                 565                 570                 575
Ala  Phe  Arg  Arg  Ala  Leu  Thr  Arg  Leu  Val  Thr  Asp  Arg  Ser  Gly  Leu
               580                 585                 590
Glu  Gln  Ala  Ile  Ser  His  Pro  Phe  Ala  Ala  Val  Ala  Pro  Gly  Val  Ser
               595                 600                 605
Pro  Gln  Gly  Gln  Val  Trp  Trp  Ala  Val  Pro  Thr  Leu  Leu  Arg  Asp  Asp
               610                 615                 620
Asp  Ala  Gly  Met  Leu  Lys  Gly  Trp  Ser  Trp  Asp  Gln  Ala  Leu  Ser  Glu
     625                 630                 635
Ala  Leu  Ser  Val  Ala  Ser  Gln  Asn  Leu  Thr  Gly  Arg  Ser  Trp  Gly  Glu
640                 645                 650                 655
```

```
Glu   His   Arg   Pro   Arg   Phe   Thr   His   Pro   Leu   Ala   Thr   Gln   Phe   Pro   Ala
                        660                     665                           670

Trp   Ala   Gly   Leu   Leu   Asn   Pro   Ala   Ser   Arg   Pro   Ile   Gly   Gly   Asp   Gly
                  675                     680                           685

Asp   Thr   Val   Leu   Ala   Asn   Gly   Leu   Val   Pro   Ser   Ala   Gly   Pro   Gln   Ala
            690                           695                     700

Thr   Tyr   Gly   Ala   Leu   Ser   Arg   Tyr   Val   Phe   Asp   Val   Gly   Asn   Trp   Asp
      705                           710                           715

Asn   Ser   Arg   Trp   Val   Val   Phe   His   Gly   Ala   Ser   Gly   His   Pro   Ala   Ser
720                           725                     730                                 735

Ala   His   Tyr   Ala   Asp   Gln   Asn   Ala   Pro   Trp   Ser   Asp   Cys   Ala   Met   Val
                        740                     745                           750

Pro   Met   Leu   Tyr   Ser   Trp   Asp   Arg   Ile   Ala   Ala   Glu   Ala   Val   Thr   Ser
                  755                     760                                 765

Gln   Glu   Leu   Val   Pro   Ala
                  770
```

( 2 ) INFORMATION FOR SEQ ID NO:45:

( i ) SEQUENCE CHARACTERISTICS:
        ( A ) LENGTH: 2325 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2325

( i x ) FEATURE:
        ( A ) NAME/KEY: mat_peptide
        ( B ) LOCATION: 4..2322

( x i ) SEQUENCE DESCRIPTION: SEQ ID NO:45:

```
ATG   ACT   ATG   GCA   GCT   AAT   ACG   GAT   CGC   GCG   GTC   TTG   CAG   GCG   GCG   CTG         48
Met   Thr   Met   Ala   Ala   Asn   Thr   Asp   Arg   Ala   Val   Leu   Gln   Ala   Ala   Leu
-1     1                       5                       10                              15

CCG   CCG   CTT   TCC   GGC   AGC   CTC   CCC   ATT   CCC   GGA   TTG   AGC   GCG   TCG   GTC         96
Pro   Pro   Leu   Ser   Gly   Ser   Leu   Pro   Ile   Pro   Gly   Leu   Ser   Ala   Ser   Val
                        20                              25                              30

CGC   GTC   CGG   CGC   GAT   GCC   TGG   GGC   ATC   CCG   CAT   ATC   AAG   GCC   TCG   GGC        144
Arg   Val   Arg   Arg   Asp   Ala   Trp   Gly   Ile   Pro   His   Ile   Lys   Ala   Ser   Gly
                  35                              40                        45

GAG   GCC   GAT   GCC   TAT   CGG   GCG   CTG   GGC   TTC   GTC   CAT   TCG   CAG   GAC   CGT        192
Glu   Ala   Asp   Ala   Tyr   Arg   Ala   Leu   Gly   Phe   Val   His   Ser   Gln   Asp   Arg
            50                              55                        60

CTT   TTC   CAG   ATG   GAG   CTG   ACG   CGT   CGC   AAG   GCG   CTG   GGA   CGC   GCG   GCC        240
Leu   Phe   Gln   Met   Glu   Leu   Thr   Arg   Arg   Lys   Ala   Leu   Gly   Arg   Ala   Ala
      65                              70                        75

GAA   TGG   CTG   GGC   GCC   GAG   GCC   GCC   GAG   GCC   GAT   ATC   CTC   GTG   CGC   CGG        288
Glu   Trp   Leu   Gly   Ala   Glu   Ala   Ala   Glu   Ala   Asp   Ile   Leu   Val   Arg   Arg
80                            85                              90                        95

CTC   GGA   ATG   GAA   AAA   GTC   TGC   CGG   CGC   GAC   TTC   GAG   GCC   TTG   GGC   GTC        336
Leu   Gly   Met   Glu   Lys   Val   Cys   Arg   Arg   Asp   Phe   Glu   Ala   Leu   Gly   Val
                        100                           105                         110

GAG   GCG   AAG   GAC   ATG   CTG   CGG   GCT   TAT   GTC   GCC   GGC   GTG   AAC   GCA   TTC        384
Glu   Ala   Lys   Asp   Met   Leu   Arg   Ala   Tyr   Val   Ala   Gly   Val   Asn   Ala   Phe
            115                           120                       125
```

| | | | | | | | | | | | | | | | | |
|---|---|---|---|---|---|---|---|---|---|---|---|---|---|---|---|---|
| CTG | GCT | TCC | GGT | GCT | CCC | CTG | CCT | GTC | GAA | TAC | GGA | TTG | CTC | GGA | GCA | 432 |
| Leu | Ala | Ser | Gly 130 | Ala | Pro | Leu | Pro 135 | Val | Glu | Tyr | Gly | Leu 140 | Leu | Gly | Ala | |
| GAG | CCG | GAG | CCC | TGG | GAG | CCT | TGG | CAC | AGC | ATC | GCG | GTG | ATG | CGC | CGG | 480 |
| Glu | Pro 145 | Glu | Pro | Trp | Glu | Pro 150 | Trp | His | Ser | Ile 155 | Ala | Val | Met | Arg | Arg | |
| CTG | GGC | CTG | CTT | ATG | GGT | GCG | GTG | TGG | TTC | AAG | CTT | TGG | CGG | ATG | CTG | 528 |
| Leu 160 | Gly | Leu | Leu | Met 165 | Gly | Ala | Val | Trp | Phe 170 | Lys | Leu | Trp | Arg | Met 175 | Leu | |
| GCG | CTG | CCG | GTG | GTC | GGA | GCC | GCG | AAT | GCG | CTG | AAG | CTG | CGC | TAT | GAC | 576 |
| Ala | Leu | Pro | Val | Val 180 | Gly | Ala | Ala | Asn | Ala 185 | Leu | Lys | Leu | Arg | Tyr 190 | Asp | |
| GAT | GGC | GGC | CGG | GAT | TTG | CTC | TGC | ATC | CCG | CCG | GGC | GCC | GAA | GCC | GAT | 624 |
| Asp | Gly | Gly | Arg 195 | Asp | Leu | Leu | Cys | Ile 200 | Pro | Pro | Gly | Ala | Glu 205 | Ala | Asp | |
| CGG | CTC | GAG | GCG | GAT | CTC | GCG | ACC | CTG | CGG | CCC | GCG | GTC | GAT | GCG | CTG | 672 |
| Arg | Leu | Glu 210 | Ala | Asp | Leu | Ala | Thr 215 | Leu | Arg | Pro | Ala | Val 220 | Asp | Ala | Leu | |
| CTG | AAG | GCG | ATG | GGC | GGC | GAT | GCC | TCC | GAT | GCT | GCC | GGC | GGC | GGC | AGC | 720 |
| Leu | Lys 225 | Ala | Met | Gly | Gly 230 | Asp | Ala | Ser | Asp | Ala 235 | Ala | Gly | Gly | Gly | Ser | |
| AAC | AAC | TGG | GCG | GTC | GCT | CCG | GGC | CGC | ACG | GCG | ACC | GGC | AGG | CCG | ATC | 768 |
| Asn 240 | Asn | Trp | Ala | Val | Ala 245 | Pro | Gly | Arg | Thr | Ala 250 | Thr | Gly | Arg | Pro | Ile 255 | |
| CTC | GCG | GGC | GAT | CCG | CAT | CGC | GTC | TTC | GAA | ATC | CCG | GGC | ATG | TAT | GCG | 816 |
| Leu | Ala | Gly | Asp | Pro 260 | His | Arg | Val | Phe | Glu 265 | Ile | Pro | Gly | Met | Tyr 270 | Ala | |
| CAG | CAT | CAT | CTG | GCC | TGC | GAC | CGG | TTC | GAC | ATG | ATC | GGC | CTG | ACC | GTG | 864 |
| Gln | His | His | Leu 275 | Ala | Cys | Asp | Arg | Phe 280 | Asp | Met | Ile | Gly | Leu 285 | Thr | Val | |
| CCG | GGC | GTG | CCG | GGC | TTC | CCG | CAC | TTC | GCG | CAT | AAC | GGC | AAG | GTC | GCC | 912 |
| Pro | Gly | Val 290 | Pro | Gly | Phe | Pro | His 295 | Phe | Ala | His | Asn | Gly 300 | Lys | Val | Ala | |
| TAT | TGC | GTC | ACC | CAT | GCC | TTC | ATG | GAC | ATC | CAC | GAT | CTC | TAT | CTG | GAG | 960 |
| Tyr | Cys 305 | Val | Thr | His | Ala | Phe 310 | Met | Asp | Ile | His | Asp 315 | Leu | Tyr | Leu | Glu | |
| CAG | TTC | GCG | GGG | GAG | GGC | CGC | ACT | GCG | CGG | TTC | GGC | AAC | GAT | TTC | GAG | 1008 |
| Gln 320 | Phe | Ala | Gly | Glu | Gly 325 | Arg | Thr | Ala | Arg | Phe 330 | Gly | Asn | Asp | Phe | Glu 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser 340 | Arg | Asp | Arg | Ile | Ala 345 | Val | Arg | Gly | Gly | Ala 350 | Asp | |
| CGC | GAG | TTC | GAT | ATC | GTC | GAG | ACG | CGC | CAT | GGC | CCG | GTT | ATC | GCG | GGC | 1104 |
| Arg | Glu | Phe | Asp | Ile 355 | Val | Glu | Thr | Arg | His 360 | Gly | Pro | Val | Ile | Ala 365 | Gly | |
| GAT | CCG | CGC | GAT | GGC | GCA | GCG | CTC | ACG | CTG | CGT | TCG | GTC | CAG | TTC | GCC | 1152 |
| Asp | Pro | Arg 370 | Asp | Gly | Ala | Ala | Leu 375 | Thr | Leu | Arg | Ser | Val 380 | Gln | Phe | Ala | |
| GAG | ACC | GAT | CTG | TCC | TTC | GAC | TGC | CTG | ACG | CGG | ATG | CCG | GGC | GCA | TCG | 1200 |
| Glu | Thr | Asp 385 | Leu | Ser | Phe | Asp | Cys 390 | Leu | Thr | Arg | Met | Pro 395 | Gly | Ala | Ser | |
| ACC | GTG | GCC | CAG | CTC | TAC | GAC | GCG | ACG | CGG | GGC | TGG | GGC | CTG | ATC | GAC | 1248 |
| Thr 400 | Val | Ala | Gln | Leu | Tyr 405 | Asp | Ala | Thr | Arg | Gly 410 | Trp | Gly | Leu | Ile | Asp 415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala 420 | Gly | Asp | Val | Ala | Gly 425 | Ser | Ile | Gly | His | Leu 430 | Val | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro 435 | Ser | Arg | Pro | Arg | Glu 440 | Asn | Gly | Trp | Leu | Pro 445 | Val | |

| | | | | | | | | | | | | | | | | |
|---|---|---|---|---|---|---|---|---|---|---|---|---|---|---|---|---|
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | | 450 | | | | 455 | | | | | 460 | | | | | |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala | |
| | 465 | | | | 470 | | | | | 475 | | | | | | |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | | 500 | | | | | 505 | | | | | 510 | | |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr | |
| | | | 515 | | | | | 520 | | | | | 525 | | | |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly | |
| | | 530 | | | | | 535 | | | | | 540 | | | | |
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala | |
| | 545 | | | | | 550 | | | | | 555 | | | | | |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | | 630 | | | | | 635 | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |
| GAT | ACC | GTG | CTG | GCC | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | | 690 | | | | | 695 | | | | | 700 | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| | 705 | | | | | 710 | | | | | 715 | | | | | |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | | 725 | | | | | 730 | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | 755 | | | | | 760 | | | | | 765 | | | |

```
CAG GAA CTC GTC CCG GCC TGA                                                                    2325
Gln Glu Leu Val Pro Ala  *
    770
```

(2) INFORMATION FOR SEQ ID NO:46:

(i) SEQUENCE CHARACTERISTICS:
        (A) LENGTH: 774 amino acids
        (B) TYPE: amino acid
        (D) TOPOLOGY: linear (ii) MOLECULE TYPE: protein (xi) SEQUENCE DESCRIPTION: SEQ ID NO:46:

```
Met Thr Met Ala Ala Asn Thr Asp Arg Ala Val Leu Gln Ala Ala Leu
 -1   1           5                  10                      15

Pro Pro Leu Ser Gly Ser Leu Pro Ile Pro Gly Leu Ser Ala Ser Val
                 20              25                      30

Arg Val Arg Arg Asp Ala Trp Gly Ile Pro His Ile Lys Ala Ser Gly
             35                  40                  45

Glu Ala Asp Ala Tyr Arg Ala Leu Gly Phe Val His Ser Gln Asp Arg
             50              55                  60

Leu Phe Gln Met Glu Leu Thr Arg Arg Lys Ala Leu Gly Arg Ala Ala
     65              70                      75

Glu Trp Leu Gly Ala Glu Ala Ala Glu Ala Asp Ile Leu Val Arg Arg
 80              85                      90                  95

Leu Gly Met Glu Lys Val Cys Arg Arg Asp Phe Glu Ala Leu Gly Val
                 100                 105                     110

Glu Ala Lys Asp Met Leu Arg Ala Tyr Val Ala Gly Val Asn Ala Phe
             115                 120                 125

Leu Ala Ser Gly Ala Pro Leu Pro Val Glu Tyr Gly Leu Leu Gly Ala
             130                 135                 140

Glu Pro Glu Pro Trp Glu Pro Trp His Ser Ile Ala Val Met Arg Arg
         145                 150                 155

Leu Gly Leu Leu Met Gly Ala Val Trp Phe Lys Leu Trp Arg Met Leu
160                  165                 170                 175

Ala Leu Pro Val Val Gly Ala Ala Asn Ala Leu Lys Leu Arg Tyr Asp
                 180                 185                 190

Asp Gly Gly Arg Asp Leu Leu Cys Ile Pro Pro Gly Ala Glu Ala Asp
             195                 200                 205

Arg Leu Glu Ala Asp Leu Ala Thr Leu Arg Pro Ala Val Asp Ala Leu
         210                 215                 220

Leu Lys Ala Met Gly Gly Asp Ala Ser Asp Ala Ala Gly Gly Gly Ser
     225                 230                 235

Asn Asn Trp Ala Val Ala Pro Gly Arg Thr Ala Thr Gly Arg Pro Ile
240                  245                 250                 255

Leu Ala Gly Asp Pro His Arg Val Phe Glu Ile Pro Gly Met Tyr Ala
                 260                 265                 270

Gln His His Leu Ala Cys Asp Arg Phe Asp Met Ile Gly Leu Thr Val
             275                 280                 285

Pro Gly Val Pro Gly Phe Pro His Phe Ala His Asn Gly Lys Val Ala
         290                 295                 300

Tyr Cys Val Thr His Ala Phe Met Asp Ile His Asp Leu Tyr Leu Glu
     305                 310                 315

Gln Phe Ala Gly Glu Gly Arg Thr Ala Arg Phe Gly Asn Asp Phe Glu
320                  325                 330                 335
```

| Pro | Val | Ala | Trp | Ser | Arg | Asp | Arg | Ile | Ala | Val | Arg | Gly | Gly | Ala | Asp |
|  |  |  | 340 |  |  |  |  | 345 |  |  |  |  |  | 350 |  |

| Arg | Glu | Phe | Asp | Ile | Val | Glu | Thr | Arg | His | Gly | Pro | Val | Ile | Ala | Gly |
|  |  |  |  | 355 |  |  |  | 360 |  |  |  |  | 365 |  |  |

| Asp | Pro | Arg | Asp | Gly | Ala | Ala | Leu | Thr | Leu | Arg | Ser | Val | Gln | Phe | Ala |
|  |  | 370 |  |  |  |  | 375 |  |  |  |  | 380 |  |  |  |

| Glu | Thr | Asp | Leu | Ser | Phe | Asp | Cys | Leu | Thr | Arg | Met | Pro | Gly | Ala | Ser |
| 385 |  |  |  |  |  | 390 |  |  |  |  | 395 |  |  |  |  |

| Thr | Val | Ala | Gln | Leu | Tyr | Asp | Ala | Thr | Arg | Gly | Trp | Gly | Leu | Ile | Asp |
| 400 |  |  |  |  | 405 |  |  |  |  | 410 |  |  |  |  | 415 |

| His | Asn | Leu | Val | Ala | Gly | Asp | Val | Ala | Gly | Ser | Ile | Gly | His | Leu | Val |
|  |  |  |  | 420 |  |  |  |  | 425 |  |  |  |  | 430 |  |

| Arg | Ala | Arg | Val | Pro | Ser | Arg | Pro | Arg | Glu | Asn | Gly | Trp | Leu | Pro | Val |
|  |  |  | 435 |  |  |  |  | 440 |  |  |  |  | 445 |  |  |

| Pro | Gly | Trp | Ser | Gly | Glu | His | Glu | Trp | Arg | Gly | Trp | Ile | Pro | His | Glu |
|  |  |  | 450 |  |  |  | 455 |  |  |  |  | 460 |  |  |  |

| Ala | Met | Pro | Arg | Val | Ile | Asp | Pro | Gly | Gly | Ile | Ile | Val | Thr | Ala |
|  | 465 |  |  |  |  | 470 |  |  |  |  | 475 |  |  |  |

| Asn | Asn | Arg | Val | Val | Ala | Asp | Asp | His | Pro | Asp | Tyr | Leu | Cys | Thr | Asp |
| 480 |  |  |  |  | 485 |  |  |  |  | 490 |  |  |  |  | 495 |

| Cys | His | Pro | Pro | Tyr | Arg | Ala | Glu | Arg | Ile | Met | Lys | Arg | Leu | Val | Ala |
|  |  |  |  | 500 |  |  |  |  | 505 |  |  |  |  | 510 |  |

| Asn | Pro | Ala | Phe | Ala | Val | Asp | Asp | Ala | Ala | Ile | His | Ala | Asp | Thr |
|  |  |  |  | 515 |  |  |  |  | 520 |  |  |  |  | 525 |  |

| Leu | Ser | Pro | His | Val | Gly | Leu | Leu | Arg | Arg | Arg | Leu | Glu | Ala | Leu | Gly |
|  |  |  | 530 |  |  |  |  | 535 |  |  |  |  | 540 |  |  |

| Ala | Arg | Asp | Asp | Ser | Ala | Ala | Glu | Gly | Leu | Arg | Gln | Met | Leu | Val | Ala |
|  |  | 545 |  |  |  |  | 550 |  |  |  |  | 555 |  |  |  |

| Trp | Asp | Gly | Arg | Met | Asp | Ala | Ala | Ser | Glu | Val | Ala | Ser | Ala | Tyr | Asn |
| 560 |  |  |  |  | 565 |  |  |  |  | 570 |  |  |  |  | 575 |

| Ala | Phe | Arg | Arg | Ala | Leu | Thr | Arg | Leu | Val | Thr | Asp | Arg | Ser | Gly | Leu |
|  |  |  |  | 580 |  |  |  |  | 585 |  |  |  |  | 590 |  |

| Glu | Gln | Ala | Ile | Ser | His | Pro | Phe | Ala | Val | Ala | Pro | Gly | Val | Ser |
|  |  |  | 595 |  |  |  |  | 600 |  |  |  |  | 605 |  |

| Pro | Gln | Gly | Gln | Val | Trp | Trp | Ala | Val | Pro | Thr | Leu | Leu | Arg | Asp | Asp |
|  |  |  | 610 |  |  |  |  | 615 |  |  |  |  | 620 |  |  |

| Asp | Ala | Gly | Met | Leu | Lys | Gly | Trp | Ser | Trp | Asp | Gln | Ala | Leu | Ser | Glu |
| 625 |  |  |  |  | 630 |  |  |  |  | 635 |  |  |  |  |  |

| Ala | Leu | Ser | Val | Ala | Ser | Gln | Asn | Leu | Thr | Gly | Arg | Ser | Trp | Gly | Glu |
| 640 |  |  |  |  | 645 |  |  |  |  | 650 |  |  |  |  | 655 |

| Glu | His | Arg | Pro | Arg | Phe | Thr | His | Pro | Leu | Ala | Thr | Gln | Phe | Pro | Ala |
|  |  |  |  | 660 |  |  |  |  | 665 |  |  |  |  | 670 |  |

| Trp | Ala | Gly | Leu | Leu | Asn | Pro | Ala | Ser | Arg | Pro | Ile | Gly | Gly | Asp | Gly |
|  |  |  | 675 |  |  |  |  | 680 |  |  |  |  | 685 |  |  |

| Asp | Thr | Val | Leu | Ala | Asn | Gly | Leu | Val | Pro | Ser | Ala | Gly | Pro | Gln | Ala |
|  |  | 690 |  |  |  |  | 695 |  |  |  |  | 700 |  |  |  |

| Thr | Tyr | Gly | Ala | Leu | Ser | Arg | Tyr | Val | Phe | Asp | Val | Gly | Asn | Trp | Asp |
|  |  | 705 |  |  |  | 710 |  |  |  |  | 715 |  |  |  |  |

| Asn | Ser | Arg | Trp | Val | Val | Phe | His | Gly | Ala | Ser | Gly | His | Pro | Ala | Ser |
| 720 |  |  |  |  | 725 |  |  |  |  | 730 |  |  |  |  | 735 |

| Ala | His | Tyr | Ala | Asp | Gln | Asn | Ala | Pro | Trp | Ser | Asp | Cys | Ala | Met | Val |
|  |  |  |  | 740 |  |  |  |  | 745 |  |  |  |  | 750 |  |

| Pro | Met | Leu | Tyr | Ser | Trp | Asp | Arg | Ile | Ala | Ala | Glu | Ala | Val | Thr | Ser |
|  |  |  |  | 755 |  |  |  |  | 760 |  |  |  |  | 765 |  |

```
Gln Glu Leu Val Pro Ala
        770
```

( 2 ) INFORMATION FOR SEQ ID NO:47:

( i ) SEQUENCE CHARACTERISTICS:
  ( A ) LENGTH: 2325 base pairs
  ( B ) TYPE: nucleic acid
  ( C ) STRANDEDNESS: double
  ( D ) TOPOLOGY: linear ( i i ) MOLECULE TYPE: DNA (genomic)

( i x ) FEATURE:
  ( A ) NAME/KEY: CDS
  ( B ) LOCATION: 1..2325

( i x ) FEATURE:
  ( A ) NAME/KEY: mat_peptide
  ( B ) LOCATION: 4..2322

( x i ) SEQUENCE DESCRIPTION: SEQ ID NO:47:

```
ATG ACT ATG GCA GCT AAT ACG GAT CGC GCG GTC TTG CAG GCG GCG CTG        48
Met Thr Met Ala Ala Asn Thr Asp Arg Ala Val Leu Gln Ala Ala Leu
 -1   1               5              10                  15

CCG CCG CTT TCC GGC AGC CTC CCC ATT CCC GGA TTG AGC GCG TCG GTC        96
Pro Pro Leu Ser Gly Ser Leu Pro Ile Pro Gly Leu Ser Ala Ser Val
                 20                  25                  30

CGC GTC CGG CGC GAT GCC TGG GGC ATC CCG CAT ATC AAG GCC TCG GGC       144
Arg Val Arg Arg Asp Ala Trp Gly Ile Pro His Ile Lys Ala Ser Gly
             35                  40                  45

GAG GCC GAT GCC TAT CGG GCG CTG GGC TTC GTC CAT TCG CAG GAC CGT       192
Glu Ala Asp Ala Tyr Arg Ala Leu Gly Phe Val His Ser Gln Asp Arg
         50                  55                  60

CTT TTC CAG ATG GAG CTG ACG CGT CGC AAG GCG CTG GGA CGC GCG GCC       240
Leu Phe Gln Met Glu Leu Thr Arg Arg Lys Ala Leu Gly Arg Ala Ala
     65                  70                  75

GAA TGG CTG GGC GCC GAG GCC GCC GAG GCC GAT ATC CTC GTG CGC CGG       288
Glu Trp Leu Gly Ala Glu Ala Ala Glu Ala Asp Ile Leu Val Arg Arg
 80                  85                  90                  95

CTC GGA ATG GAA AAA GTC TGC CGG CGC GAC TTC GAG GCC TTG GGC GTC       336
Leu Gly Met Glu Lys Val Cys Arg Arg Asp Phe Glu Ala Leu Gly Val
                100                 105                 110

GAG GCG AAG GAC ATG CTG CGG GCT TAT GTC GCC GGC GTG AAC GCA TTC       384
Glu Ala Lys Asp Met Leu Arg Ala Tyr Val Ala Gly Val Asn Ala Phe
            115                 120                 125

CTG GCT TCC GGT GCT CCC CTG CCT GTC GAA TAC GGA TTG CTC GGA GCA       432
Leu Ala Ser Gly Ala Pro Leu Pro Val Glu Tyr Gly Leu Leu Gly Ala
        130                 135                 140

GAG CCG GAG CCC TGG GAG CCT TGG CAC AGC ATC GCG GTG ATG CGC CGG       480
Glu Pro Glu Pro Trp Glu Pro Trp His Ser Ile Ala Val Met Arg Arg
    145                 150                 155

CTG GGC CTG CTT ATG GGT TCG GTG TGG TTC AAG CTC TGG CGG ATG CTG       528
Leu Gly Leu Leu Met Gly Ser Val Trp Phe Lys Leu Trp Arg Met Leu
160                 165                 170                 175

GCG CTG CCG GTG GTC GGA GCC GCG AAT GCG CTG AAG CTG CGC TAT GAC       576
Ala Leu Pro Val Val Gly Ala Ala Asn Ala Leu Lys Leu Arg Tyr Asp
                180                 185                 190

GAT GGC GGC CGG GAT TTG CTC TGC ATC CCG CCG GGC GCC GAA GCC GAT       624
Asp Gly Gly Arg Asp Leu Leu Cys Ile Pro Pro Gly Ala Glu Ala Asp
            195                 200                 205

CGG CTC GAG GCG GAT CTC GCG ACC CTG CGG CCC GCG GTC GAT GCG CTG       672
Arg Leu Glu Ala Asp Leu Ala Thr Leu Arg Pro Ala Val Asp Ala Leu
        210                 215                 220
```

| | | | | | | | | | | | | | | | | |
|---|---|---|---|---|---|---|---|---|---|---|---|---|---|---|---|---|
| CTG | AAG | GCG | ATG | GGC | GGC | GAT | GCC | TCC | GAT | GCT | GCC | GGC | GGC | GGC | AGC | 720 |
| Leu | Lys | Ala | Met | Gly | Gly | Asp | Ala | Ser | Asp | Ala | Ala | Gly | Gly | Gly | Ser | |
| | 225 | | | | 230 | | | | | 235 | | | | | | |
| AAC | AAC | TGG | GCG | GTC | GCT | CCG | GGC | CGC | ACG | GCG | ACC | GGC | AGG | CCG | ATC | 768 |
| Asn | Asn | Trp | Ala | Val | Ala | Pro | Gly | Arg | Thr | Ala | Thr | Gly | Arg | Pro | Ile | |
| 240 | | | | | 245 | | | | | 250 | | | | | 255 | |
| CTC | GCG | GGC | GAT | CCG | CAT | CGC | GTC | TTC | GAA | ATA | CCG | GGC | ATC | TAT | GCG | 816 |
| Leu | Ala | Gly | Asp | Pro | His | Arg | Val | Phe | Glu | Ile | Pro | Gly | Ile | Tyr | Ala | |
| | | | | | 260 | | | | | 265 | | | | | 270 | |
| CAG | CAT | CAT | CTG | GCC | TGC | GAC | CGG | TTC | GAC | ATG | ATC | GGC | CTG | ACC | GTG | 864 |
| Gln | His | His | Leu | Ala | Cys | Asp | Arg | Phe | Asp | Met | Ile | Gly | Leu | Thr | Val | |
| | | | 275 | | | | | 280 | | | | | 285 | | | |
| CCG | GGC | GTG | CCG | GGC | TTC | CCG | CAC | TTC | GCG | CAT | AAC | GGC | AAG | GTC | GCC | 912 |
| Pro | Gly | Val | Pro | Gly | Phe | Pro | His | Phe | Ala | His | Asn | Gly | Lys | Val | Ala | |
| | | 290 | | | | | 295 | | | | | 300 | | | | |
| TAT | TGC | GTC | ACC | CAT | GCC | TTC | ATG | GAC | ATC | CAC | GAT | CTC | TAT | CTC | GAG | 960 |
| Tyr | Cys | Val | Thr | His | Ala | Phe | Met | Asp | Ile | His | Asp | Leu | Tyr | Leu | Glu | |
| | 305 | | | | | 310 | | | | | 315 | | | | | |
| CAG | TTC | GCG | GGG | GAG | GGC | CGC | ACT | GCG | CGG | TTC | GGC | AAC | GAT | TTC | GAG | 1008 |
| Gln | Phe | Ala | Gly | Glu | Gly | Arg | Thr | Ala | Arg | Phe | Gly | Asn | Asp | Phe | Glu | |
| 320 | | | | | 325 | | | | | 330 | | | | | 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | | 340 | | | | | 345 | | | | | 350 | | |
| CGC | GAG | TTC | GAT | ATA | GTC | AAG | ACG | CGC | CAT | GGC | CCG | GTT | ATC | GCG | GGC | 1104 |
| Arg | Glu | Phe | Asp | Ile | Val | Lys | Thr | Arg | His | Gly | Pro | Val | Ile | Ala | Gly | |
| | | | 355 | | | | | 360 | | | | | 365 | | | |
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | | 370 | | | | | 375 | | | | | 380 | | | | |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| | 385 | | | | | 390 | | | | | 395 | | | | | |
| ACC | GTG | GCC | CAG | CTC | TAC | GAC | GCG | ACG | CGC | GGC | TGG | GGC | CTG | ATC | GAC | 1248 |
| Thr | Val | Ala | Gln | Leu | Tyr | Asp | Ala | Thr | Arg | Gly | Trp | Gly | Leu | Ile | Asp | |
| 400 | | | | | 405 | | | | | 410 | | | | | 415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala | Gly | Asp | Val | Ala | Gly | Ser | Ile | Gly | His | Leu | Val | |
| | | | | 420 | | | | | 425 | | | | | 430 | | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val | |
| | | | 435 | | | | | 440 | | | | | 445 | | | |
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | | 450 | | | | | 455 | | | | | 460 | | | | |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala | |
| | 465 | | | | | 470 | | | | | 475 | | | | | |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | | 500 | | | | | 505 | | | | | 510 | | |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr | |
| | | | 515 | | | | | 520 | | | | | 525 | | | |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly | |
| | | 530 | | | | | 535 | | | | | 540 | | | | |

| | | | | | | | | | | | | | | | | |
|---|---|---|---|---|---|---|---|---|---|---|---|---|---|---|---|---|
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala | |
| | 545 | | | | 550 | | | | | | 555 | | | | | |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | 630 | | | | | 635 | | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | | 690 | | | | | 695 | | | | | 700 | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| | 705 | | | | | 710 | | | | | 715 | | | | | |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | | 725 | | | | | 730 | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | | 755 | | | | | 760 | | | | | 765 | | |
| CAG | GAA | CTC | GTC | CCG | GCC | TGA | | | | | | | | | | 2325 |
| Gln | Glu | Leu | Val | Pro | Ala | * | | | | | | | | | | |
| | | | | 770 | | | | | | | | | | | | |

( 2 ) INFORMATION FOR SEQ ID NO:48:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

| | | | | | | | | | | | | | | |
|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| - 1 | 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | | 20 | | | | | 25 | | | | | 30 | |

| | | | | | | | | | | | | | | |
|---|---|---|---|---|---|---|---|---|---|---|---|---|---|---|
| Arg | Val | Arg | Arg 35 | Asp | Ala | Trp | Gly | Ile 40 | Pro | His | Ile | Lys 45 | Ala | Ser | Gly |
| Glu | Ala | Asp 50 | Ala | Tyr | Arg | Ala | Leu 55 | Gly | Phe | Val | His | Ser 60 | Gln | Asp | Arg |
| Leu | Phe 65 | Gln | Met | Glu | Leu | Thr 70 | Arg | Arg | Lys | Ala | Leu 75 | Gly | Arg | Ala | Ala |
| Glu 80 | Trp | Leu | Gly | Ala | Glu 85 | Ala | Ala | Glu | Ala | Asp 90 | Ile | Leu | Val | Arg | Arg 95 |
| Leu | Gly | Met | Glu | Lys 100 | Val | Cys | Arg | Arg | Asp 105 | Phe | Glu | Ala | Leu | Gly 110 | Val |
| Glu | Ala | Lys | Asp 115 | Met | Leu | Arg | Ala | Tyr 120 | Val | Ala | Gly | Val | Asn 125 | Ala | Phe |
| Leu | Ala | Ser 130 | Gly | Ala | Pro | Leu | Pro 135 | Val | Glu | Tyr | Gly | Leu 140 | Leu | Gly | Ala |
| Glu | Pro 145 | Glu | Pro | Trp | Glu | Pro 150 | Trp | His | Ser | Ile | Ala 155 | Val | Met | Arg | Arg |
| Leu 160 | Gly | Leu | Leu | Met | Gly 165 | Ser | Val | Trp | Phe | Lys 170 | Leu | Trp | Arg | Met | Leu 175 |
| Ala | Leu | Pro | Val | Val 180 | Gly | Ala | Ala | Asn | Ala 185 | Leu | Lys | Leu | Arg | Tyr 190 | Asp |
| Asp | Gly | Gly | Arg 195 | Asp | Leu | Leu | Cys | Ile 200 | Pro | Pro | Gly | Ala | Glu 205 | Ala | Asp |
| Arg | Leu | Glu 210 | Ala | Asp | Leu | Ala | Thr 215 | Leu | Arg | Pro | Ala | Val 220 | Asp | Ala | Leu |
| Leu | Lys 225 | Ala | Met | Gly | Gly | Asp 230 | Ala | Ser | Asp | Ala | Ala 235 | Gly | Gly | Gly | Ser |
| Asn 240 | Asn | Trp | Ala | Val | Ala 245 | Pro | Gly | Arg | Thr | Ala 250 | Thr | Gly | Arg | Pro | Ile 255 |
| Leu | Ala | Gly | Asp | Pro 260 | His | Arg | Val | Phe | Glu 265 | Ile | Pro | Gly | Ile | Tyr 270 | Ala |
| Gln | His | His | Leu 275 | Ala | Cys | Asp | Arg | Phe 280 | Asp | Met | Ile | Gly | Leu 285 | Thr | Val |
| Pro | Gly | Val 290 | Pro | Gly | Phe | Pro | His 295 | Phe | Ala | His | Asn | Gly 300 | Lys | Val | Ala |
| Tyr | Cys 305 | Val | Thr | His | Ala | Phe 310 | Met | Asp | Ile | His | Asp 315 | Leu | Tyr | Leu | Glu |
| Gln 320 | Phe | Ala | Gly | Glu | Gly 325 | Arg | Thr | Ala | Arg | Phe 330 | Gly | Asn | Asp | Phe | Glu 335 |
| Pro | Val | Ala | Trp | Ser 340 | Arg | Asp | Arg | Ile | Ala 345 | Val | Arg | Gly | Gly | Ala 350 | Asp |
| Arg | Glu | Phe | Asp 355 | Ile | Val | Lys | Thr | Arg 360 | His | Gly | Pro | Val | Ile 365 | Ala | Gly |
| Asp | Pro | Arg 370 | Asp | Gly | Ala | Ala | Leu 375 | Thr | Leu | Arg | Ser | Val 380 | Gln | Phe | Ala |
| Glu | Thr 385 | Asp | Leu | Ser | Phe | Asp 390 | Cys | Leu | Thr | Arg | Met 395 | Pro | Gly | Ala | Ser |
| Thr 400 | Val | Ala | Gln | Leu | Tyr 405 | Asp | Ala | Thr | Arg | Gly 410 | Trp | Gly | Leu | Ile | Asp 415 |
| His | Asn | Leu | Val | Ala 420 | Gly | Asp | Val | Ala | Gly 425 | Ser | Ile | Gly | His | Leu 430 | Val |
| Arg | Ala | Arg | Val 435 | Pro | Ser | Arg | Pro | Arg 440 | Glu | Asn | Gly | Trp | Leu 445 | Pro | Val |
| Pro | Gly | Trp 450 | Ser | Gly | Glu | His | Glu 455 | Trp | Arg | Gly | Trp | Ile 460 | Pro | His | Glu |

| Ala | Met | Pro | Arg | Val | Ile | Asp | Pro | Pro | Gly | Gly | Ile | Ile | Val | Thr | Ala |
|---|---|---|---|---|---|---|---|---|---|---|---|---|---|---|---|
| | 465 | | | | | 470 | | | | 475 | | | | | |

| Asn | Asn | Arg | Val | Val | Ala | Asp | Asp | His | Pro | Asp | Tyr | Leu | Cys | Thr | Asp |
|---|---|---|---|---|---|---|---|---|---|---|---|---|---|---|---|
| 480 | | | | | 485 | | | | 490 | | | | | | 495 |

| Cys | His | Pro | Pro | Tyr | Arg | Ala | Glu | Arg | Ile | Met | Lys | Arg | Leu | Val | Ala |
|---|---|---|---|---|---|---|---|---|---|---|---|---|---|---|---|
| | | | | 500 | | | | | 505 | | | | | 510 | |

| Asn | Pro | Ala | Phe | Ala | Val | Asp | Asp | Ala | Ala | Ile | His | Ala | Asp | Thr |
|---|---|---|---|---|---|---|---|---|---|---|---|---|---|---|
| | | | 515 | | | | 520 | | | | | 525 | | |

| Leu | Ser | Pro | His | Val | Gly | Leu | Leu | Arg | Arg | Arg | Leu | Glu | Ala | Leu | Gly |
|---|---|---|---|---|---|---|---|---|---|---|---|---|---|---|---|
| | | 530 | | | | | 535 | | | | | 540 | | | |

| Ala | Arg | Asp | Asp | Ser | Ala | Ala | Glu | Gly | Leu | Arg | Gln | Met | Leu | Val | Ala |
|---|---|---|---|---|---|---|---|---|---|---|---|---|---|---|---|
| | 545 | | | | | 550 | | | | | 555 | | | | |

| Trp | Asp | Gly | Arg | Met | Asp | Ala | Ala | Ser | Glu | Val | Ala | Ser | Ala | Tyr | Asn |
|---|---|---|---|---|---|---|---|---|---|---|---|---|---|---|---|
| 560 | | | | | 565 | | | | 570 | | | | | | 575 |

| Ala | Phe | Arg | Arg | Ala | Leu | Thr | Arg | Leu | Val | Thr | Asp | Arg | Ser | Gly | Leu |
|---|---|---|---|---|---|---|---|---|---|---|---|---|---|---|---|
| | | | | 580 | | | | 585 | | | | | 590 | | |

| Glu | Gln | Ala | Ile | Ser | His | Pro | Phe | Ala | Ala | Val | Ala | Pro | Gly | Val | Ser |
|---|---|---|---|---|---|---|---|---|---|---|---|---|---|---|---|
| | | | 595 | | | | 600 | | | | | 605 | | | |

| Pro | Gln | Gly | Gln | Val | Trp | Trp | Ala | Val | Pro | Thr | Leu | Leu | Arg | Asp | Asp |
|---|---|---|---|---|---|---|---|---|---|---|---|---|---|---|---|
| | | 610 | | | | | 615 | | | | | 620 | | | |

| Asp | Ala | Gly | Met | Leu | Lys | Gly | Trp | Ser | Trp | Asp | Gln | Ala | Leu | Ser | Glu |
|---|---|---|---|---|---|---|---|---|---|---|---|---|---|---|---|
| | 625 | | | | | 630 | | | | | 635 | | | | |

| Ala | Leu | Ser | Val | Ala | Ser | Gln | Asn | Leu | Thr | Gly | Arg | Ser | Trp | Gly | Glu |
|---|---|---|---|---|---|---|---|---|---|---|---|---|---|---|---|
| 640 | | | | | 645 | | | | 650 | | | | | | 655 |

| Glu | His | Arg | Pro | Arg | Phe | Thr | His | Pro | Leu | Ala | Thr | Gln | Phe | Pro | Ala |
|---|---|---|---|---|---|---|---|---|---|---|---|---|---|---|---|
| | | | | 660 | | | | | 665 | | | | | 670 | |

| Trp | Ala | Gly | Leu | Leu | Asn | Pro | Ala | Ser | Arg | Pro | Ile | Gly | Gly | Asp | Gly |
|---|---|---|---|---|---|---|---|---|---|---|---|---|---|---|---|
| | | | 675 | | | | | 680 | | | | | 685 | | |

| Asp | Thr | Val | Leu | Ala | Asn | Gly | Leu | Val | Pro | Ser | Ala | Gly | Pro | Gln | Ala |
|---|---|---|---|---|---|---|---|---|---|---|---|---|---|---|---|
| | | 690 | | | | | 695 | | | | | 700 | | | |

| Thr | Tyr | Gly | Ala | Leu | Ser | Arg | Tyr | Val | Phe | Asp | Val | Gly | Asn | Trp | Asp |
|---|---|---|---|---|---|---|---|---|---|---|---|---|---|---|---|
| | 705 | | | | | 710 | | | | | 715 | | | | |

| Asn | Ser | Arg | Trp | Val | Val | Phe | His | Gly | Ala | Ser | Gly | His | Pro | Ala | Ser |
|---|---|---|---|---|---|---|---|---|---|---|---|---|---|---|---|
| 720 | | | | | 725 | | | | | 730 | | | | | 735 |

| Ala | His | Tyr | Ala | Asp | Gln | Asn | Ala | Pro | Trp | Ser | Asp | Cys | Ala | Met | Val |
|---|---|---|---|---|---|---|---|---|---|---|---|---|---|---|---|
| | | | | 740 | | | | | 745 | | | | | 750 | |

| Pro | Met | Leu | Tyr | Ser | Trp | Asp | Arg | Ile | Ala | Ala | Glu | Ala | Val | Thr | Ser |
|---|---|---|---|---|---|---|---|---|---|---|---|---|---|---|---|
| | | | 755 | | | | | 760 | | | | | 765 | | |

| Gln | Glu | Leu | Val | Pro | Ala |
|---|---|---|---|---|---|
| | | 770 | | | |

( 2 ) INFORMATION FOR SEQ ID NO:49:

( i ) SEQUENCE CHARACTERISTICS:
        ( A ) LENGTH: 2325 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2325

( i x ) FEATURE:
        ( A ) NAME/KEY: mat_peptide
        ( B ) LOCATION: 4..2322

( x i ) SEQUENCE DESCRIPTION: SEQ ID NO:49:

| | | | | | | | | | | | | | | | | |
|---|---|---|---|---|---|---|---|---|---|---|---|---|---|---|---|---|
| ATG | ACT | ATG | GCA | GCT | AAT | ACG | GAT | CGC | GCG | GTC | TTG | CAG | GCG | GCG | CTG | 48 |
| Met | Thr | Met | Ala | Ala | Asn | Thr | Asp | Arg | Ala | Val | Leu | Gln | Ala | Ala | Leu | |
| -1 | 1 | | | | 5 | | | | | 10 | | | | | 15 | |
| CCG | CCG | CTT | TCC | GGC | AGC | CTC | CCC | ATT | CCC | GGA | TTG | AGC | GCG | TCG | GTC | 96 |
| Pro | Pro | Leu | Ser | Gly | Ser | Leu | Pro | Ile | Pro | Gly | Leu | Ser | Ala | Ser | Val | |
| | | | | 20 | | | | | 25 | | | | | 30 | | |
| CGC | GTC | CGG | CGC | GAT | GCC | TGG | GGC | ATC | CCG | CAT | ATC | AAG | GCC | TCG | GGC | 144 |
| Arg | Val | Arg | Arg | Asp | Ala | Trp | Gly | Ile | Pro | His | Ile | Lys | Ala | Ser | Gly | |
| | | | 35 | | | | | 40 | | | | | 45 | | | |
| GAG | GCC | GAT | GCC | TAT | CGG | GCG | CTG | GGC | TTC | GTC | CAT | TCG | CAG | GAC | CGT | 192 |
| Glu | Ala | Asp | Ala | Tyr | Arg | Ala | Leu | Gly | Phe | Val | His | Ser | Gln | Asp | Arg | |
| | | 50 | | | | | 55 | | | | | 60 | | | | |
| CTT | TTC | CAG | ATG | GAG | CTG | ACG | CGT | CGC | AAG | GCG | CTG | GGA | CGC | GCG | GCC | 240 |
| Leu | Phe | Gln | Met | Glu | Leu | Thr | Arg | Arg | Lys | Ala | Leu | Gly | Arg | Ala | Ala | |
| | 65 | | | | | 70 | | | | | 75 | | | | | |
| GAA | TGG | CTG | GGC | GCC | GAG | GCC | GCC | GAG | GCC | GAT | ATC | CTC | GTG | CGC | CGG | 288 |
| Glu | Trp | Leu | Gly | Ala | Glu | Ala | Ala | Glu | Ala | Asp | Ile | Leu | Val | Arg | Arg | |
| 80 | | | | | 85 | | | | | 90 | | | | | 95 | |
| CTC | GGA | ATG | GAA | AAA | GTC | TGC | CGG | CGC | GAC | TTC | GAG | GCC | TTG | GGC | GTC | 336 |
| Leu | Gly | Met | Glu | Lys | Val | Cys | Arg | Arg | Asp | Phe | Glu | Ala | Leu | Gly | Val | |
| | | | | 100 | | | | | 105 | | | | | 110 | | |
| GAG | GCG | AAG | GAC | ATG | CTG | CGG | GCT | TAT | GTC | GCC | GGC | GTG | AAC | GCA | TTC | 384 |
| Glu | Ala | Lys | Asp | Met | Leu | Arg | Ala | Tyr | Val | Ala | Gly | Val | Asn | Ala | Phe | |
| | | | 115 | | | | | 120 | | | | | 125 | | | |
| CTG | GCT | TCC | GGT | GCT | CCC | CTG | CCT | GTC | GAA | TAC | GGA | TTG | CTC | GGA | GCA | 432 |
| Leu | Ala | Ser | Gly | Ala | Pro | Leu | Pro | Val | Glu | Tyr | Gly | Leu | Leu | Gly | Ala | |
| | | | 130 | | | | | 135 | | | | | 140 | | | |
| GAG | CCG | GAG | CCC | TGG | GAG | CCT | TGG | CAC | AGC | ATC | GCG | GTG | ATG | CGT | CGA | 480 |
| Glu | Pro | Glu | Pro | Trp | Glu | Pro | Trp | His | Ser | Ile | Ala | Val | Met | Arg | Arg | |
| | 145 | | | | | 150 | | | | | 155 | | | | | |
| CTC | GGC | CTG | CTT | CTG | GGA | TCC | GTG | TGG | TTC | AAG | CTC | TGG | CGG | GCG | CTA | 528 |
| Leu | Gly | Leu | Leu | Leu | Gly | Ser | Val | Trp | Phe | Lys | Leu | Trp | Arg | Ala | Leu | |
| 160 | | | | | 165 | | | | | 170 | | | | | 175 | |
| GCG | CTG | CCG | GTG | GTC | GGA | GCC | GCG | AAT | GCG | CTG | AAG | CTG | CGC | TAT | GAC | 576 |
| Ala | Leu | Pro | Val | Val | Gly | Ala | Ala | Asn | Ala | Leu | Lys | Leu | Arg | Tyr | Asp | |
| | | | | 180 | | | | | 185 | | | | | 190 | | |
| GAT | GGC | GGC | CGG | GAT | TTG | CTC | TGC | ATC | CCG | CCG | GGC | GCC | GAA | GCC | GAT | 624 |
| Asp | Gly | Gly | Arg | Asp | Leu | Leu | Cys | Ile | Pro | Pro | Gly | Ala | Glu | Ala | Asp | |
| | | | 195 | | | | | 200 | | | | | 205 | | | |
| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | | 210 | | | | | 215 | | | | | 220 | | | | |
| CTG | AAG | GCG | ATG | GGC | GGC | GAT | GCC | TCC | GAT | GCT | GCC | GGC | GGC | GGC | AGC | 720 |
| Leu | Lys | Ala | Met | Gly | Gly | Asp | Ala | Ser | Asp | Ala | Ala | Gly | Gly | Gly | Ser | |
| | 225 | | | | | 230 | | | | | 235 | | | | | |
| AAC | AAC | TGG | GCG | GTC | GCT | CCG | GGC | CGC | ACG | GCG | ACC | GGC | AGG | CCG | ATC | 768 |
| Asn | Asn | Trp | Ala | Val | Ala | Pro | Gly | Arg | Thr | Ala | Thr | Gly | Arg | Pro | Ile | |
| 240 | | | | | 245 | | | | | 250 | | | | | 255 | |
| CTC | GCG | GGC | GAT | CCG | CAT | CGC | GTC | TTC | GAA | ATC | CCT | GGC | TAT | TAT | GCG | 816 |
| Leu | Ala | Gly | Asp | Pro | His | Arg | Val | Phe | Glu | Ile | Pro | Gly | Tyr | Tyr | Ala | |
| | | | | 260 | | | | | 265 | | | | | 270 | | |
| CAG | CAT | CAT | CTG | GCC | TGC | GAC | CGG | TTC | GAC | ATG | ATC | GGC | CTG | ACC | GTG | 864 |
| Gln | His | His | Leu | Ala | Cys | Asp | Arg | Phe | Asp | Met | Ile | Gly | Leu | Thr | Val | |
| | | | 275 | | | | | 280 | | | | | 285 | | | |
| CCG | GGC | GTG | CCG | GGC | TTC | CCG | CAC | TTC | GCG | CAT | AAC | GGC | AAG | GTC | GCC | 912 |
| Pro | Gly | Val | Pro | Gly | Phe | Pro | His | Phe | Ala | His | Asn | Gly | Lys | Val | Ala | |
| | | | | 290 | | | | | 295 | | | | | 300 | | |

| | | | | | | | | | | | | | | | | |
|---|---|---|---|---|---|---|---|---|---|---|---|---|---|---|---|---|
| TAT | TGC | GTC | ACC | CAT | GCC | TTC | ATG | GAC | ATC | CAC | GAT | CTC | TAT | CTC | GAG | 960 |
| Tyr | Cys | Val | Thr | His | Ala | Phe | Met | Asp | Ile | His | Asp | Leu | Tyr | Leu | Glu | |
| | 305 | | | | | 310 | | | | | 315 | | | | | |
| CAG | TTC | GCG | GGG | GAG | GGC | CGC | ACT | GCG | CGG | TTC | GGC | AAC | GAT | TTC | GAG | 1008 |
| Gln | Phe | Ala | Gly | Glu | Gly | Arg | Thr | Ala | Arg | Phe | Gly | Asn | Asp | Phe | Glu | |
| 320 | | | | | 325 | | | | | 330 | | | | | 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | 340 | | | | | 345 | | | | | 350 | | | |
| CGC | GAG | TTC | GAT | ATC | GTC | GAG | ACG | CGC | CAT | GGC | CCG | GTT | ATC | GCG | GGC | 1104 |
| Arg | Glu | Phe | Asp | Ile | Val | Glu | Thr | Arg | His | Gly | Pro | Val | Ile | Ala | Gly | |
| | | | 355 | | | | | 360 | | | | | 365 | | | |
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | | 370 | | | | | 375 | | | | | 380 | | | | |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| | 385 | | | | | 390 | | | | | 395 | | | | | |
| ACC | GTG | GCC | CAG | CTC | TAC | GAC | GCG | ACG | CGC | GGC | TGG | GGC | CTG | ATC | GAC | 1248 |
| Thr | Val | Ala | Gln | Leu | Tyr | Asp | Ala | Thr | Arg | Gly | Trp | Gly | Leu | Ile | Asp | |
| 400 | | | | | 405 | | | | | 410 | | | | | 415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala | Gly | Asp | Val | Ala | Gly | Ser | Ile | Gly | His | Leu | Val | |
| | | | | 420 | | | | | 425 | | | | | 430 | | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val | |
| | | | 435 | | | | | 440 | | | | | 445 | | | |
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | | 450 | | | | | 455 | | | | | 460 | | | | |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala | |
| | 465 | | | | | 470 | | | | | 475 | | | | | |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | | 500 | | | | | 505 | | | | | 510 | | |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr | |
| | | | 515 | | | | | 520 | | | | | 525 | | | |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly | |
| | | 530 | | | | | 535 | | | | | 540 | | | | |
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala | |
| | 545 | | | | | 550 | | | | | 555 | | | | | |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |

| | | | | | | | | | | | | | | | | |
|---|---|---|---|---|---|---|---|---|---|---|---|---|---|---|---|---|
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | 630 | | | | | 635 | | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | 650 | | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | | 690 | | | | | 695 | | | | | 700 | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| | 705 | | | | | 710 | | | | | 715 | | | | | |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | | 725 | | | | 730 | | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | 755 | | | | | 760 | | | | | 765 | | | |
| CAG | GAA | CTC | GTC | CCG | GCC | TGA | | | | | | | | | | 2325 |
| Gln | Glu | Leu | Val | Pro | Ala | * | | | | | | | | | | |
| | | 770 | | | | | | | | | | | | | | |

(2) INFORMATION FOR SEQ ID NO:50:

(i) SEQUENCE CHARACTERISTICS:
        (A) LENGTH: 774 amino acids
        (B) TYPE: amino acid
        (D) TOPOLOGY: linear (ii) MOLECULE TYPE: protein (xi) SEQUENCE DESCRIPTION: SEQ ID NO:50:

| | | | | | | | | | | | | | | |
|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| -1 | 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | | 20 | | | | | 25 | | | | | 30 | |
| Arg | Val | Arg | Arg | Asp | Ala | Trp | Gly | Ile | Pro | His | Ile | Lys | Ala | Ser | Gly |
| | | | 35 | | | | | 40 | | | | | 45 | | |
| Glu | Ala | Asp | Ala | Tyr | Arg | Ala | Leu | Gly | Phe | Val | His | Ser | Gln | Asp | Arg |
| | | 50 | | | | | 55 | | | | | 60 | | | |
| Leu | Phe | Gln | Met | Glu | Leu | Thr | Arg | Arg | Lys | Ala | Leu | Gly | Arg | Ala | Ala |
| 65 | | | | | 70 | | | | | 75 | | | | | |
| Glu | Trp | Leu | Gly | Ala | Glu | Ala | Ala | Glu | Ala | Asp | Ile | Leu | Val | Arg | Arg |
| 80 | | | | | 85 | | | | | 90 | | | | | 95 |
| Leu | Gly | Met | Glu | Lys | Val | Cys | Arg | Arg | Asp | Phe | Glu | Ala | Leu | Gly | Val |
| | | | | 100 | | | | | 105 | | | | | 110 | |
| Glu | Ala | Lys | Asp | Met | Leu | Arg | Ala | Tyr | Val | Ala | Gly | Val | Asn | Ala | Phe |
| | | | 115 | | | | | 120 | | | | | 125 | | |
| Leu | Ala | Ser | Gly | Ala | Pro | Leu | Pro | Val | Glu | Tyr | Gly | Leu | Leu | Gly | Ala |
| | | 130 | | | | | 135 | | | | | 140 | | | |

-continued

| | | | | | | | | | | | | | | |
|---|---|---|---|---|---|---|---|---|---|---|---|---|---|---|
| Glu | Pro | Glu | Pro | Trp | Glu | Pro | Trp | His | Ser | Ile | Ala | Val | Met | Arg | Arg |
| 145 | | | | 150 | | | | | | 155 | | | | | |
| Leu | Gly | Leu | Leu | Leu | Gly | Ser | Val | Trp | Phe | Lys | Leu | Trp | Arg | Ala | Leu |
| 160 | | | | | 165 | | | | 170 | | | | | 175 | |
| Ala | Leu | Pro | Val | Val | Gly | Ala | Ala | Asn | Ala | Leu | Lys | Leu | Arg | Tyr | Asp |
| | | | | 180 | | | | 185 | | | | | 190 | | |
| Asp | Gly | Gly | Arg | Asp | Leu | Leu | Cys | Ile | Pro | Pro | Gly | Ala | Glu | Ala | Asp |
| | | | 195 | | | | | 200 | | | | 205 | | | |
| Arg | Leu | Glu | Ala | Asp | Leu | Ala | Thr | Leu | Arg | Pro | Ala | Val | Asp | Ala | Leu |
| | | 210 | | | | | 215 | | | | | 220 | | | |
| Leu | Lys | Ala | Met | Gly | Gly | Asp | Ala | Ser | Asp | Ala | Ala | Gly | Gly | Gly | Ser |
| | 225 | | | | | 230 | | | | | 235 | | | | |
| Asn | Asn | Trp | Ala | Val | Ala | Pro | Gly | Arg | Thr | Ala | Thr | Gly | Arg | Pro | Ile |
| 240 | | | | | 245 | | | | | 250 | | | | | 255 |
| Leu | Ala | Gly | Asp | Pro | His | Arg | Val | Phe | Glu | Ile | Pro | Gly | Tyr | Tyr | Ala |
| | | | | 260 | | | | | 265 | | | | | 270 | |
| Gln | His | His | Leu | Ala | Cys | Asp | Arg | Phe | Asp | Met | Ile | Gly | Leu | Thr | Val |
| | | | | 275 | | | | | 280 | | | | 285 | | |
| Pro | Gly | Val | Pro | Gly | Phe | Pro | His | Phe | Ala | His | Asn | Gly | Lys | Val | Ala |
| | | | 290 | | | | 295 | | | | | 300 | | | |
| Tyr | Cys | Val | Thr | His | Ala | Phe | Met | Asp | Ile | His | Asp | Leu | Tyr | Leu | Glu |
| | 305 | | | | | 310 | | | | | 315 | | | | |
| Gln | Phe | Ala | Gly | Glu | Gly | Arg | Thr | Ala | Arg | Phe | Gly | Asn | Asp | Phe | Glu |
| 320 | | | | | 325 | | | | | 330 | | | | | 335 |
| Pro | Val | Ala | Trp | Ser | Arg | Asp | Arg | Ile | Ala | Val | Arg | Gly | Gly | Ala | Asp |
| | | | | 340 | | | | | 345 | | | | | 350 | |
| Arg | Glu | Phe | Asp | Ile | Val | Glu | Thr | Arg | His | Gly | Pro | Val | Ile | Ala | Gly |
| | | | 355 | | | | | 360 | | | | | 365 | | |
| Asp | Pro | Arg | Asp | Gly | Ala | Ala | Leu | Thr | Leu | Arg | Ser | Val | Gln | Phe | Ala |
| | | 370 | | | | | 375 | | | | | 380 | | | |
| Glu | Thr | Asp | Leu | Ser | Phe | Asp | Cys | Leu | Thr | Arg | Met | Pro | Gly | Ala | Ser |
| | 385 | | | | | 390 | | | | | 395 | | | | |
| Thr | Val | Ala | Gln | Leu | Tyr | Asp | Ala | Thr | Arg | Gly | Trp | Gly | Leu | Ile | Asp |
| 400 | | | | | 405 | | | | | 410 | | | | | 415 |
| His | Asn | Leu | Val | Ala | Gly | Asp | Val | Ala | Gly | Ser | Ile | Gly | His | Leu | Val |
| | | | | 420 | | | | | 425 | | | | | 430 | |
| Arg | Ala | Arg | Val | Pro | Ser | Arg | Pro | Arg | Glu | Asn | Gly | Trp | Leu | Pro | Val |
| | | | 435 | | | | | 440 | | | | | 445 | | |
| Pro | Gly | Trp | Ser | Gly | Glu | His | Glu | Trp | Arg | Gly | Trp | Ile | Pro | His | Glu |
| | | | 450 | | | | 455 | | | | | 460 | | | |
| Ala | Met | Pro | Arg | Val | Ile | Asp | Pro | Pro | Gly | Gly | Ile | Val | Thr | Ala | |
| | 465 | | | | | 470 | | | | | 475 | | | | |
| Asn | Asn | Arg | Val | Val | Ala | Asp | His | Pro | Asp | Tyr | Leu | Cys | Thr | Asp | |
| 480 | | | | | 485 | | | | 490 | | | | | 495 | |
| Cys | His | Pro | Pro | Tyr | Arg | Ala | Glu | Arg | Ile | Met | Lys | Arg | Leu | Val | Ala |
| | | | | 500 | | | | | 505 | | | | | 510 | |
| Asn | Pro | Ala | Phe | Ala | Val | Asp | Asp | Ala | Ala | Ile | His | Ala | Asp | Thr | |
| | | | 515 | | | | | 520 | | | | | 525 | | |
| Leu | Ser | Pro | His | Val | Gly | Leu | Leu | Arg | Arg | Arg | Leu | Glu | Ala | Leu | Gly |
| | | 530 | | | | | 535 | | | | | 540 | | | |
| Ala | Arg | Asp | Asp | Ser | Ala | Ala | Glu | Gly | Leu | Arg | Gln | Met | Leu | Val | Ala |
| | | 545 | | | | | 550 | | | | | 555 | | | |
| Trp | Asp | Gly | Arg | Met | Asp | Ala | Ala | Ser | Glu | Val | Ala | Ser | Ala | Tyr | Asn |
| 560 | | | | | 565 | | | | | 570 | | | | | 575 |

| | | | | | | | | | | | | | | | |
|---|---|---|---|---|---|---|---|---|---|---|---|---|---|---|---|
|Ala|Phe|Arg|Arg|Ala|Leu|Thr|Arg|Leu|Val|Thr|Asp|Arg|Ser|Gly|Leu|
| | | | |580| | | |585| | | | |590| | |
|Glu|Gln|Ala|Ile|Ser|His|Pro|Phe|Ala|Val|Ala|Pro|Gly|Val|Ser| |
| | | |595| | | |600| | | |605| | | | |
|Pro|Gln|Gly|Gln|Val|Trp|Trp|Ala|Val|Pro|Thr|Leu|Leu|Arg|Asp|Asp|
| | |610| | | |615| | | |620| | | | | |
|Asp|Ala|Gly|Met|Leu|Lys|Gly|Trp|Ser|Trp|Asp|Gln|Ala|Leu|Ser|Glu|
| |625| | | |630| | | |635| | | | | | |
|Ala|Leu|Ser|Val|Ala|Ser|Gln|Asn|Leu|Thr|Gly|Arg|Ser|Trp|Gly|Glu|
|640| | | |645| | | |650| | | |655| | | |
|Glu|His|Arg|Pro|Arg|Phe|Thr|His|Pro|Leu|Ala|Thr|Gln|Phe|Pro|Ala|
| | | |660| | | |665| | | |670| | | | |
|Trp|Ala|Gly|Leu|Leu|Asn|Pro|Ala|Ser|Arg|Pro|Ile|Gly|Gly|Asp|Gly|
| | |675| | | |680| | | |685| | | | | |
|Asp|Thr|Val|Leu|Ala|Asn|Gly|Leu|Val|Pro|Ser|Ala|Gly|Pro|Gln|Ala|
| |690| | | |695| | | |700| | | | | | |
|Thr|Tyr|Gly|Ala|Leu|Ser|Arg|Tyr|Val|Phe|Asp|Val|Gly|Asn|Trp|Asp|
|705| | | |710| | | |715| | | | | | | |
|Asn|Ser|Arg|Trp|Val|Val|Phe|His|Gly|Ala|Ser|Gly|His|Pro|Ala|Ser|
|720| | | |725| | | |730| | | |735| | | |
|Ala|His|Tyr|Ala|Asp|Gln|Asn|Ala|Pro|Trp|Ser|Asp|Cys|Ala|Met|Val|
| | | |740| | | |745| | | |750| | | | |
|Pro|Met|Leu|Tyr|Ser|Trp|Asp|Arg|Ile|Ala|Ala|Glu|Ala|Val|Thr|Ser|
| | |755| | | |760| | | |765| | | | | |
|Gln|Glu|Leu|Val|Pro|Ala| | | | | | | | | | |
| |770| | | | | | | | | | | | | | |

( 2 ) INFORMATION FOR SEQ ID NO:51:

( i ) SEQUENCE CHARACTERISTICS:
        ( A ) LENGTH: 2325 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2325

( i x ) FEATURE:
        ( A ) NAME/KEY: mat_peptide
        ( B ) LOCATION: 4..2322

( x i ) SEQUENCE DESCRIPTION: SEQ ID NO:51:

| | | | | | | | | | | | | | | | | |
|---|---|---|---|---|---|---|---|---|---|---|---|---|---|---|---|---|
|ATG|ACT|ATG|GCA|GCT|AAT|ACG|GAT|CGC|GCG|GTC|TTG|CAG|GCG|GCG|CTG|48|
|Met|Thr|Met|Ala|Ala|Asn|Thr|Asp|Arg|Ala|Val|Leu|Gln|Ala|Ala|Leu| |
|-1|1| | | |5| | | |10| | | | |15| | |
|CCG|CCG|CTT|TCC|GGC|AGC|CTC|CCC|ATT|CCC|GGA|TTG|AGC|GCG|TCG|GTC|96|
|Pro|Pro|Leu|Ser|Gly|Ser|Leu|Pro|Ile|Pro|Gly|Leu|Ser|Ala|Ser|Val| |
| | | | |20| | | |25| | | | |30| | | |
|CGC|GTC|CGG|CGC|GAT|GCC|TGG|GGC|ATC|CCG|CAT|ATC|AAG|GCC|TCG|GGC|144|
|Arg|Val|Arg|Arg|Asp|Ala|Trp|Gly|Ile|Pro|His|Ile|Lys|Ala|Ser|Gly| |
| | | |35| | | |40| | | | |45| | | | |
|GAG|CTC|GAT|GCC|TAT|CGG|GCG|CTG|GGC|TTC|GTC|CAT|TCG|CAG|GAC|CGT|192|
|Glu|Leu|Asp|Ala|Tyr|Arg|Ala|Leu|Gly|Phe|Val|His|Ser|Gln|Asp|Arg| |
| | |50| | | |55| | | | |60| | | | | |
|CTT|TTC|CAG|ATG|GAG|CTG|ACG|CGT|CGC|AAG|GCG|CTG|GGA|CGC|GCG|GCC|240|
|Leu|Phe|Gln|Met|Glu|Leu|Thr|Arg|Arg|Lys|Ala|Leu|Gly|Arg|Ala|Ala| |
| |65| | | |70| | | | |75| | | | | | |

| | | | | | | | | | | | | | | | | |
|---|---|---|---|---|---|---|---|---|---|---|---|---|---|---|---|---|
| GAA | TGG | CTG | GGC | GCC | GAG | GCC | GCC | GAG | GCC | GAT | ATC | CTC | GTG | CGC | CGG | 288 |
| Glu | Trp | Leu | Gly | Ala | Glu | Ala | Ala | Glu | Ala | Asp | Ile | Leu | Val | Arg | Arg | |
| 80 | | | | 85 | | | | | 90 | | | | | | 95 | |
| CTC | GGA | ATG | GAA | AAA | GTC | TGC | CGG | CGC | GAC | TTC | GAG | GCC | TTG | GGC | GTC | 336 |
| Leu | Gly | Met | Glu | Lys | Val | Cys | Arg | Arg | Asp | Phe | Glu | Ala | Leu | Gly | Val | |
| | | | | 100 | | | | | 105 | | | | | 110 | | |
| GAG | GCG | AAG | GAG | ATG | CTG | CGG | GCT | TAT | GTC | GCC | GGC | GTG | AAC | GCA | TTC | 384 |
| Glu | Ala | Lys | Glu | Met | Leu | Arg | Ala | Tyr | Val | Ala | Gly | Val | Asn | Ala | Phe | |
| | | | 115 | | | | | 120 | | | | | 125 | | | |
| CTG | GCT | TCC | GGT | GCT | CCC | CTG | CCT | GTC | GAA | TAC | GGA | TTG | CTC | GGA | GCA | 432 |
| Leu | Ala | Ser | Gly | Ala | Pro | Leu | Pro | Val | Glu | Tyr | Gly | Leu | Leu | Gly | Ala | |
| | | 130 | | | | | 135 | | | | | 140 | | | | |
| GAG | CCG | GAG | CCC | TGG | GAG | CCT | TGG | CAC | AGC | ATC | GCG | GTG | ATG | CGC | CGG | 480 |
| Glu | Pro | Glu | Pro | Trp | Glu | Pro | Trp | His | Ser | Ile | Ala | Val | Met | Arg | Arg | |
| 145 | | | | | 150 | | | | | 155 | | | | | | |
| CTG | GGC | CTG | CTT | ATG | GGT | TCG | GTG | TGG | TTC | AAG | CTC | TGG | CGG | ATG | CTG | 528 |
| Leu | Gly | Leu | Leu | Met | Gly | Ser | Val | Trp | Phe | Lys | Leu | Trp | Arg | Met | Leu | |
| 160 | | | | | 165 | | | | | 170 | | | | | 175 | |
| GCG | CTG | CCG | GTG | GTC | GGA | GCC | GCG | AAT | GCG | CTG | AAG | CTG | CGC | TAT | GAC | 576 |
| Ala | Leu | Pro | Val | Val | Gly | Ala | Ala | Asn | Ala | Leu | Lys | Leu | Arg | Tyr | Asp | |
| | | | | 180 | | | | | 185 | | | | | 190 | | |
| GAT | GGC | GGC | CGG | GAT | TTG | CTC | TGC | ATC | CCG | CCG | GGC | GCC | GAA | GCC | GAT | 624 |
| Asp | Gly | Gly | Arg | Asp | Leu | Leu | Cys | Ile | Pro | Pro | Gly | Ala | Glu | Ala | Asp | |
| | | | 195 | | | | | 200 | | | | | 205 | | | |
| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | | 210 | | | | | 215 | | | | | 220 | | | | |
| CTG | AAG | GCG | ATG | GGC | GGC | GAT | GCC | TCC | GAT | GCT | GCC | GGC | GGC | GGC | AGC | 720 |
| Leu | Lys | Ala | Met | Gly | Gly | Asp | Ala | Ser | Asp | Ala | Ala | Gly | Gly | Gly | Ser | |
| | 225 | | | | | 230 | | | | | 235 | | | | | |
| AAC | AAC | TGG | GCG | GTC | GCT | CCG | GGC | CGC | ACG | GCG | ACC | GGC | AGG | CCG | ATC | 768 |
| Asn | Asn | Trp | Ala | Val | Ala | Pro | Gly | Arg | Thr | Ala | Thr | Gly | Arg | Pro | Ile | |
| 240 | | | | | 245 | | | | | 250 | | | | | 255 | |
| CTC | GCG | GGC | GAT | CCG | CAT | CGC | GTC | TTC | GAA | ATC | CCG | GGC | ATG | TAT | GCG | 816 |
| Leu | Ala | Gly | Asp | Pro | His | Arg | Val | Phe | Glu | Ile | Pro | Gly | Met | Tyr | Ala | |
| | | | | 260 | | | | | 265 | | | | | 270 | | |
| CAG | CAT | CAT | CTG | GCC | TGC | GAC | CGG | TTC | GAC | ATG | ATC | GGC | CTG | ACC | GTG | 864 |
| Gln | His | His | Leu | Ala | Cys | Asp | Arg | Phe | Asp | Met | Ile | Gly | Leu | Thr | Val | |
| | | | 275 | | | | | 280 | | | | | 285 | | | |
| CCG | GGC | GTG | CCG | GGC | TTC | CCG | CAC | TTC | GCG | CAT | AAC | GGC | AAG | GTC | GCC | 912 |
| Pro | Gly | Val | Pro | Gly | Phe | Pro | His | Phe | Ala | His | Asn | Gly | Lys | Val | Ala | |
| | | 290 | | | | | 295 | | | | | 300 | | | | |
| TAT | TGC | GTC | ACC | CAT | GCC | TTC | ATG | GAC | ATC | CAC | GAT | CTC | TAT | CTC | GAG | 960 |
| Tyr | Cys | Val | Thr | His | Ala | Phe | Met | Asp | Ile | His | Asp | Leu | Tyr | Leu | Glu | |
| | 305 | | | | | 310 | | | | | 315 | | | | | |
| CAG | TTC | GCG | GGG | GAG | GGC | CGC | ACT | GCG | CGG | TTC | GGC | AAC | GAT | TTC | GAG | 1008 |
| Gln | Phe | Ala | Gly | Glu | Gly | Arg | Thr | Ala | Arg | Phe | Gly | Asn | Asp | Phe | Glu | |
| 320 | | | | | 325 | | | | | 330 | | | | | 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | | 340 | | | | | 345 | | | | | 350 | | |
| CGC | GAG | TTC | GAT | ATC | GTC | GAG | ACG | CGC | CAT | GGC | CCG | GTT | ATC | GCG | GGC | 1104 |
| Arg | Glu | Phe | Asp | Ile | Val | Glu | Thr | Arg | His | Gly | Pro | Val | Ile | Ala | Gly | |
| | | | 355 | | | | | 360 | | | | | 365 | | | |
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | | 370 | | | | | 375 | | | | | 380 | | | | |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| | 385 | | | | | 390 | | | | | 395 | | | | | |

| | | | | | | | | | | | | | | | | |
|---|---|---|---|---|---|---|---|---|---|---|---|---|---|---|---|---|
| ACC | GTG | GCC | CAG | CTC | TAC | GAC | GCG | ACG | CGC | GGC | TGG | GGC | CTG | ATC | GAC | 1248 |
| Thr | Val | Ala | Gln | Leu | Tyr | Asp | Ala | Thr | Arg | Gly | Trp | Gly | Leu | Ile | Asp | |
| 400 | | | | | 405 | | | | 410 | | | | | | 415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala | Gly | Asp | Val | Ala | Gly | Ser | Ile | Gly | His | Leu | Val | |
| | | | | 420 | | | | | 425 | | | | | 430 | | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val | |
| | | | 435 | | | | | 440 | | | | | 445 | | | |
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | | 450 | | | | | 455 | | | | | 460 | | | | |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala | |
| | 465 | | | | | 470 | | | | | 475 | | | | | |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | | 500 | | | | | 505 | | | | | 510 | | |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr | |
| | | | 515 | | | | | 520 | | | | | 525 | | | |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly | |
| | | 530 | | | | | 535 | | | | | 540 | | | | |
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala | |
| | 545 | | | | | 550 | | | | | 555 | | | | | |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | | 630 | | | | | 635 | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | 690 | | | | | 695 | | | | | 700 | | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| 705 | | | | | 710 | | | | | 715 | | | | | | |

| | | | | | | | | | | | | | | | | |
|---|---|---|---|---|---|---|---|---|---|---|---|---|---|---|---|---|
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | 725 | | | | | 730 | | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | 755 | | | | 760 | | | | | | 765 | | | |
| CAG | GAA | CTC | GTC | CCG | GCC | TGA | | | | | | | | | | 2325 |
| Gln | Glu | Leu | Val | Pro | Ala | * | | | | | | | | | | |
| | | 770 | | | | | | | | | | | | | | |

( 2 ) INFORMATION FOR SEQ ID NO:52:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:52:

| | | | | | | | | | | | | | | |
|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| -1 | 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | | 20 | | | | | 25 | | | | | 30 | |
| Arg | Val | Arg | Arg | Asp | Ala | Trp | Gly | Ile | Pro | His | Ile | Lys | Ala | Ser | Gly |
| | | | 35 | | | | | 40 | | | | | 45 | | |
| Glu | Leu | Asp | Ala | Tyr | Arg | Ala | Leu | Gly | Phe | Val | His | Ser | Gln | Asp | Arg |
| | | | 50 | | | | | 55 | | | | | 60 | | |
| Leu | Phe | Gln | Met | Glu | Leu | Thr | Arg | Arg | Lys | Ala | Leu | Gly | Arg | Ala | Ala |
| | 65 | | | | | 70 | | | | | 75 | | | | |
| Glu | Trp | Leu | Gly | Ala | Glu | Ala | Ala | Glu | Ala | Asp | Ile | Leu | Val | Arg | Arg |
| 80 | | | | | 85 | | | | | 90 | | | | | 95 |
| Leu | Gly | Met | Glu | Lys | Val | Cys | Arg | Arg | Asp | Phe | Glu | Ala | Leu | Gly | Val |
| | | | | 100 | | | | | 105 | | | | | 110 | |
| Glu | Ala | Lys | Glu | Met | Leu | Arg | Ala | Tyr | Val | Ala | Gly | Val | Asn | Ala | Phe |
| | | | 115 | | | | | 120 | | | | | 125 | | |
| Leu | Ala | Ser | Gly | Ala | Pro | Leu | Pro | Val | Glu | Tyr | Gly | Leu | Leu | Gly | Ala |
| | | | 130 | | | | | 135 | | | | | 140 | | |
| Glu | Pro | Glu | Pro | Trp | Glu | Pro | Trp | His | Ser | Ile | Ala | Val | Met | Arg | Arg |
| | 145 | | | | | 150 | | | | | 155 | | | | |
| Leu | Gly | Leu | Leu | Met | Gly | Ser | Val | Trp | Phe | Lys | Leu | Trp | Arg | Met | Leu |
| 160 | | | | | 165 | | | | | 170 | | | | | 175 |
| Ala | Leu | Pro | Val | Val | Gly | Ala | Ala | Asn | Ala | Leu | Lys | Leu | Arg | Tyr | Asp |
| | | | | 180 | | | | | 185 | | | | | 190 | |
| Asp | Gly | Gly | Arg | Asp | Leu | Leu | Cys | Ile | Pro | Pro | Gly | Ala | Glu | Ala | Asp |
| | | | 195 | | | | | 200 | | | | | 205 | | |
| Arg | Leu | Glu | Ala | Asp | Leu | Ala | Thr | Leu | Arg | Pro | Ala | Val | Asp | Ala | Leu |
| | | | 210 | | | | | 215 | | | | | 220 | | |
| Leu | Lys | Ala | Met | Gly | Gly | Asp | Ala | Ser | Asp | Ala | Ala | Gly | Gly | Gly | Ser |
| | 225 | | | | | 230 | | | | | 235 | | | | |
| Asn | Asn | Trp | Ala | Val | Ala | Pro | Gly | Arg | Thr | Ala | Thr | Gly | Arg | Pro | Ile |
| 240 | | | | | 245 | | | | | 250 | | | | | 255 |
| Leu | Ala | Gly | Asp | Pro | His | Arg | Val | Phe | Glu | Ile | Pro | Gly | Met | Tyr | Ala |
| | | | | 260 | | | | | 265 | | | | | 270 | |

-continued

| | | | | | | | | | | | | | | |
|---|---|---|---|---|---|---|---|---|---|---|---|---|---|---|
|Gln|His|His|Leu|Ala|Cys|Asp|Arg|Phe|Asp|Met|Ile|Gly|Leu|Thr|Val|
| | |275| | | | |280| | | |285| | | |
|Pro|Gly|Val|Pro|Gly|Phe|Pro|His|Phe|Ala|His|Asn|Gly|Lys|Val|Ala|
| | |290| | | |295| | | |300| | | | |
|Tyr|Cys|Val|Thr|His|Ala|Phe|Met|Asp|Ile|His|Asp|Leu|Tyr|Leu|Glu|
| |305| | | | |310| | | |315| | | | |
|Gln|Phe|Ala|Gly|Glu|Gly|Arg|Thr|Ala|Arg|Phe|Gly|Asn|Asp|Phe|Glu|
|320| | | |325| | | |330| | | | | |335|
|Pro|Val|Ala|Trp|Ser|Arg|Asp|Arg|Ile|Ala|Val|Arg|Gly|Gly|Ala|Asp|
| | | |340| | | |345| | | | | |350| |
|Arg|Glu|Phe|Asp|Ile|Val|Glu|Thr|Arg|His|Gly|Pro|Val|Ile|Ala|Gly|
| | | |355| | | |360| | | | |365| | |
|Asp|Pro|Arg|Asp|Gly|Ala|Ala|Leu|Thr|Leu|Arg|Ser|Val|Gln|Phe|Ala|
| | |370| | | |375| | | | |380| | | |
|Glu|Thr|Asp|Leu|Ser|Phe|Asp|Cys|Leu|Thr|Arg|Met|Pro|Gly|Ala|Ser|
| |385| | | | |390| | | |395| | | | |
|Thr|Val|Ala|Gln|Leu|Tyr|Asp|Ala|Thr|Arg|Gly|Trp|Gly|Leu|Ile|Asp|
|400| | | |405| | | |410| | | | | |415|
|His|Asn|Leu|Val|Ala|Gly|Asp|Val|Ala|Gly|Ser|Ile|Gly|His|Leu|Val|
| | | |420| | | |425| | | | |430| | |
|Arg|Ala|Arg|Val|Pro|Ser|Arg|Pro|Arg|Glu|Asn|Gly|Trp|Leu|Pro|Val|
| | |435| | | |440| | | | |445| | | |
|Pro|Gly|Trp|Ser|Gly|Glu|His|Glu|Trp|Arg|Gly|Trp|Ile|Pro|His|Glu|
| | |450| | | |455| | | |460| | | | |
|Ala|Met|Pro|Arg|Val|Ile|Asp|Pro|Pro|Gly|Gly|Ile|Ile|Val|Thr|Ala|
| |465| | | |470| | | | |475| | | | |
|Asn|Asn|Arg|Val|Val|Ala|Asp|Asp|His|Pro|Asp|Tyr|Leu|Cys|Thr|Asp|
|480| | | |485| | | |490| | | | | |495|
|Cys|His|Pro|Pro|Tyr|Arg|Ala|Glu|Arg|Ile|Met|Lys|Arg|Leu|Val|Ala|
| | | |500| | | |505| | | | |510| | |
|Asn|Pro|Ala|Phe|Ala|Val|Asp|Asp|Ala|Ala|Ile|His|Ala|Asp|Thr|
| | | |515| | | |520| | | |525| | | |
|Leu|Ser|Pro|His|Val|Gly|Leu|Leu|Arg|Arg|Arg|Leu|Glu|Ala|Leu|Gly|
| | |530| | | |535| | | | |540| | | |
|Ala|Arg|Asp|Asp|Ser|Ala|Ala|Glu|Gly|Leu|Arg|Gln|Met|Leu|Val|Ala|
| |545| | | |550| | | | |555| | | | |
|Trp|Asp|Gly|Arg|Met|Asp|Ala|Ala|Ser|Glu|Val|Ala|Ser|Ala|Tyr|Asn|
|560| | | |565| | | |570| | | | | |575|
|Ala|Phe|Arg|Arg|Ala|Leu|Thr|Arg|Leu|Val|Thr|Asp|Arg|Ser|Gly|Leu|
| | | |580| | | |585| | | |590| | | |
|Glu|Gln|Ala|Ile|Ser|His|Pro|Phe|Ala|Ala|Val|Ala|Pro|Gly|Val|Ser|
| | |595| | | |600| | | |605| | | | |
|Pro|Gln|Gly|Gln|Val|Trp|Trp|Ala|Val|Pro|Thr|Leu|Leu|Arg|Asp|Asp|
| | |610| | | |615| | | |620| | | | |
|Asp|Ala|Gly|Met|Leu|Lys|Gly|Trp|Ser|Trp|Asp|Gln|Ala|Leu|Ser|Glu|
| |625| | | |630| | | |635| | | | | |
|Ala|Leu|Ser|Val|Ala|Ser|Gln|Asn|Leu|Thr|Gly|Arg|Ser|Trp|Gly|Glu|
|640| | | |645| | | |650| | | | | |655|
|Glu|His|Arg|Pro|Arg|Phe|Thr|His|Pro|Leu|Ala|Thr|Gln|Phe|Pro|Ala|
| | | |660| | | |665| | | |670| | | |
|Trp|Ala|Gly|Leu|Leu|Asn|Pro|Ala|Ser|Arg|Pro|Ile|Gly|Gly|Asp|Gly|
| | |675| | | |680| | | |685| | | | |
|Asp|Thr|Val|Leu|Ala|Asn|Gly|Leu|Val|Pro|Ser|Ala|Gly|Pro|Gln|Ala|
| |690| | | |695| | | |700| | | | | |

| Thr | Tyr | Gly | Ala | Leu | Ser | Arg | Tyr | Val | Phe | Asp | Val | Gly | Asn | Trp | Asp |
|---|---|---|---|---|---|---|---|---|---|---|---|---|---|---|---|
| | | 705 | | | | 710 | | | | | 715 | | | | |

| Asn | Ser | Arg | Trp | Val | Val | Phe | His | Gly | Ala | Ser | Gly | His | Pro | Ala | Ser |
|---|---|---|---|---|---|---|---|---|---|---|---|---|---|---|---|
| 720 | | | | | 725 | | | | | 730 | | | | | 735 |

| Ala | His | Tyr | Ala | Asp | Gln | Asn | Ala | Pro | Trp | Ser | Asp | Cys | Ala | Met | Val |
|---|---|---|---|---|---|---|---|---|---|---|---|---|---|---|---|
| | | | | 740 | | | | | 745 | | | | | 750 | |

| Pro | Met | Leu | Tyr | Ser | Trp | Asp | Arg | Ile | Ala | Ala | Glu | Ala | Val | Thr | Ser |
|---|---|---|---|---|---|---|---|---|---|---|---|---|---|---|---|
| | | | 755 | | | | | 760 | | | | | 765 | | |

| Gln | Glu | Leu | Val | Pro | Ala |
|---|---|---|---|---|---|
| | | | 770 | | |

( 2 ) INFORMATION FOR SEQ ID NO:53:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:53:

```
CCGGGTGTGT ACACCAAGGT TACCAACTAC CTAGACTGGA TTCGTGACAA CATGCGACCG      60
TGA                                                                    63
```

( 2 ) INFORMATION FOR SEQ ID NO:54:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:54:

```
AGCTTCACGG TCGCATGTTG TCACGAATCC AGTCTAGGTA GTTGGTAACC TTGGTGTACA      60
CAC                                                                    63
```

( 2 ) INFORMATION FOR SEQ ID NO:55:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:55:

```
AGCTTGTCCT CGAGATCAAA TAAAGGCTCC TTTTGGAGCC TTTTTTTTTT G               51
```

( 2 ) INFORMATION FOR SEQ ID NO:56:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:56:

```
TCGACAAAAA AAAAAGGCTC CAAAAGGAGC CTTTAATTGA TCTCGAGGAC A               51
```

( 2 ) INFORMATION FOR SEQ ID NO:57:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:57:

AATTCGGATC CAAGCTTA                                            18

( 2 ) INFORMATION FOR SEQ ID NO:58:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:58:

CGCGTAAGCT TGGATCCG                                            18

( 2 ) INFORMATION FOR SEQ ID NO:59:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

Xaa Thr Met Ala Ala Asn Thr
1                   5

( 2 ) INFORMATION FOR SEQ ID NO:60:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:60:

CGATAAAATG ACTATGGCGG CCAACACC                              28

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:61:

GATCGGTGTT GGCCGCCATA GTCATTTTAT                            30

( 2 ) INFORMATION FOR SEQ ID NO:62:

( i ) SEQUENCE CHARACTERISTICS:

(A) LENGTH: 28 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:62:

CGATAAAATG ACTATGGCAG CTAATACG 28

(2) INFORMATION FOR SEQ ID NO:63:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:63:

GATCCGTATT AGCTGCCATA GTCATTTTAT 30

(2) INFORMATION FOR SEQ ID NO:64:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:64:

GACCGGCAGC GCTAGCGCCC GCCAGAGCTT GA 32

CEPHALOSPORIN C ACYLASE

The present application is a national stage application based on PCT/JP94/01799, filed Oct. 26, 1994.

The invention relates to a new cephalosporin C acylase (hereinafter referred to as "CC acylase"). More particularly, it relates to a new mutant CC acylase produced by protein engineering, a DNA coding therefor, an expression vector containing the said DNA, a microorganism transformed with the said expression vector, and the production of the CC acylase by culturing the said transformant.

The cephalosporin C acylase is a general term for an enzyme, which is, in common, capable of hydrolyzing cephalosporin C to 7-aminocephalosporanic acid (7-ACA).

Hitherto, there have been found three enzymes which should be classified as CC acylase, namely Cephalosporin C acylases SE83, N176 and V22, amino acid sequences of which are disclosed in Journal of Fermentation and Bioengineering Vol. 72, 232–243 (1991). In this literature, numbering of the amino acid sequence of CC acylase is begun at the methionine group of the N-terminal portion thereof. However, numbering of the amino acid sequence of CC acylase is begun at the threonine group adjacent to the methionine group of the N-terminal portion thereof in this Specification, because the N-terminal methionine of α-subunit of mature CC acylase obtained by expressing CC acylase gene in prokaryote is removed by an enzyme (e.g. aminopeptidase) to give a mature CC acylase having the threonine group as the N-terminal amino acid thereof. Production of native type CC acylase by recombinant DNA technology is also disclosed in the said literature and it has been found that the expressed CC acylase is intracellularly processed to give an active form composed of α-subunit and β-subunit. However, efficiency of the processing is generally low in E. coli. From the results of extensive studies, the inventors of this invention have succeeded in producing mutant CC acylases which have more desirable properties which are characterized by higher enzymatic potency, alteration of pH profile, higher efficiency of processing and the like.

The new mutant CC acylase of this invention can be characterized by the following.

A mutant CC acylase wherein at least one amino acid at the $Ala^{49}$, $Met^{164}$, $Ser^{166}$, $Met^{174}$, $Glu^{358}$, $Met^{465}$, $Met^{508}$ or $Met^{750}$ position of the amino acid sequence of the native CC acylase is replaced by a different amino acid.

Preferred examples of the different amino acid to replace $Met^{164}$ may include neutral amino acids such as glycine, alanine, leucine and the like.

Preferred examples of the different amino acid to replace $Ser^{166}$, $Met^{174}$, $Met^{465}$, $Met^{506}$ and/or $Met^{750}$ may include neutral amino acids such as alanine and the like.

Preferred examples of the different amino acid to replace $Glu^{358}$ may include neutral-amino acids (e.g. isoleucine, etc.), basic amino acids (e.g. lysine, etc.) and the like.

Most preferable example of the different amino acid to replace $Ala^{49}$ is leucine.

The mutant CC acylase of this invention may also be a mutant CC acylase prepared by replacing at least one amino acid at another position of the amino acid sequence of native CC acylase with a different amino acid, for example, by replacing $Met^{269}$ and/or $Cys^{305}$ of the mutant CC acylase with (a) different amino acid(s).

A preferred example of the mutant CC acylase can be represented by the following formula in its precursor form before processing into α-subunit and β-subunit thereof:
A1-48-X1-A50-163-X2-Gly-X3-A167-173-X4-A175-357-X5-A359-464-X6-A466-505-X7-A507-749-X8-A751-773 wherein A1-48 is the same amino acid sequence as that from $Thr^1$ to $Glu^{48}$ of native CC acylase, A50-163 is the same amino acid sequence as that from $Asp^{50}$ to $Leu^{163}$ of native CC acylase, A167-173 is the same amino acid sequence as that from $Val^{167}$ to $Arg^{173}$ of native CC acylase, A175-357 is the same amino acid sequence as that from $Leu^{175}$ to $Val^{357}$ of native CC acylase, A359-464 is the same amino acid sequence as that from $Thr^{359}$ to $Ala^{464}$ of native CC acylase, A466-505 is the same amino acid sequence as that from $Pro^{466}$ to $Ile^{505}$ of native CC acylase, A507-749 is the same amino acid sequence as that from $Lys^{507}$ to $Ala^{749}$ of native CC acylase, A751-773 is the same amino acid sequence as that from $Val^{751}$ to $Ala^{773}$ of native CC acylase, X1 is Ala or a different amino acid, X2, X4, X6, X7 and X8 are each Met or a different amino acid, X3 is Ser or a different amino acid and X5 is Glu or a different amino acid, providing that $Met^{269}$ and/or $Cys^{305}$ may be replaced by (a) different amino acid(s), and when X1 is Ala, X2, X4, X6, X7 and X8 are each Met, X3 is Ser and X5 is an amino acid other than Glu.

In this specification, a nomenclature for naming a specific mutant CC acylase is conveniently employed. According to this nomenclature, for example, a mutant CC acylase which is prepared by replacing the methionine residue at position 164 of the amino acid sequence of native CC acylase with leucine should be designated as a mutant CC acylase M164L, in which M is a one-letter abbreviation of the methionine (an amino acid) residue to be replaced, 164 is a position number of the amino acid sequence of native CC acylase and L is a one-letter abbreviation of leucine (the different amino acid) used for replacing the methionine (the former amino acid) residue. On the other hand, for example, mutant CC acylases. M164L and M164A are prepared by replacing the methionine residue at position 164 of the amino acid sequence of native CC acylase with leucine and alanine, respectively. A mutant CC acylase M164L/M174A/M269Y is prepared by replacing the methionine residue at position 164 of the amino acid sequence of native CC acylase with leucine, the methionine residue at position 174 of the amino acid sequence of native CC acylase with alanine and the methionine residue at position 269 of the amino acid sequence of native CC acylase with tyrosine.

The mutant CC acylase of this invention can be prepared by recombinant DNA technology, polypeptide synthesis and the like.

Namely, the new CC acylase can be prepared by culturing a host cell transformed with an expression vector comprising DNA encoding amino acid sequence of the new CC acylase in a nutrient medium and recovering the new CC acylase from the cultured broth.

Particulars of this process are explained in more detail as follows.

The host cell may include microorganisms [bacteria (e.g. *Escherichia coli, Bacillus subtilis,* etc.), yeast (e.g. *Saccharomyces cerevisiae,* etc.), animal cell lines and cultured plant cells]. Preferred examples of the microorganism may include bacteria, especially a strain belonging to the genus Escherichia (e.g. *E. coli* JM109 ATCC 53323, *E. coli* HB101 ATCC 33694, *E. coli* HB101-16 FERM BP-1872, *E. coli* 294 ATCC 31446, etc.), yeast, especially a strain belonging to the genus Saccharomyces [e.g. *Saccharomyces cerevisiae* AH22], animal cell lines [e.g. mouse L929-cell, Chinese hamster ovary (CHO) cell, etc.] and the like.

When a becterium, especially *E. coli* is used as a host cell, the expression vector is usually composed of at least promoter-operator region, initiation codon, DNA encoding amino acid sequence of the new CC acylase, termination codon, terminator region and replicatable unit. When yeasts or animal cells are used as host cells, the expression vector is preferably composed of at least promoter, initiation codon, DNA encoding amino acid sequences of the signal peptide and the new CC acylase, and termination codon. It is possible that enhancer sequence, 5'- and 3'-noncoding region of the new CC acylase, splicing junctions, polyadenylation site and replicatable unit are also inserted into the expression vector.

The promoter-operator region comprises promoter, operator and Shine-Dalgarno (SD) sequence (e.g. AAGG, etc.). Preferable promoter-operator region may include conventionally employed promoter-operator region (e.g. PL-promoter and trp-promoter for *E. coli*) and promoter of the CC acylase N-176 chromosomal gene. The promoter for expression of the new CC acylase in yeast may include the promoter of the TRP1 gene, the ADHI or ADHII gene and acid phosphatase (pH05) gene for *S. cerevisiae* and the promoter for the expression of the new CC acylase in mammalian cells may include SV40 early or late-promoter, HTLV-LTR-promoter, mouse metallothionein I(MMT)-promoter, vaccinia-promoter and the like.

Preferable initiation codon may include methionine codon (ATG).

The signal peptide may include a signal peptide of conventionally employed other enzymes (signal peptide of the native t-PA, signal peptide of the native plasminogen) and the like.

The DNA encoding amino acid sequence of the new CC acylase can be prepared in a conventional manner such as a partial or whole DNA synthesis using DNA synthesizer and/or treatment of the complete DNA sequence coding for the native CC acylase inserted in a suitable vector (e.g. pCCN 176-2) obtainable from a transformant [e.g. *E. coli* JM109 (pCCN 176-2) FERM BP-3047] in a suitable manner such as a conventional mutation method [e.g. cassette mutation method (cf. Tokunaga, T. et al., Eur. J. Biochem. 153, 445–449 (1985)), PCR mutation method (cf. Higuchi, R. et al., Nucleic Acids Res. 16, 7351–7367 (1988)), Kunkel's method (cf. Kunkel, T. A. et al., Methods Enzymol. 154, 367 (1987)) and the like] in addition to treatment with a suitable enzyme (e.g. restriction enzyme, alkaline phosphatase, polynucleotide kinase, DNA ligase, DNA polymerase, etc.).

The termination codon(s) may include a conventionally employed termination codon (e.g. TAG, TGA, etc.).

The terminator region may include natural or synthetic terminator (e.g. synthetic fd phage terminator, etc.).

The replicatable unit is a DNA compound capable of replicating the whole DNA sequence belonging thereto in a host cell, and may include natural plasmid, artificially modified plasmid (e.g. DNA fragment prepared from natural plasmid) and synthetic plasmid. Preferable examples of the plasmid may include plasmid pBR322 and the artificially modified thereof (DNA fragment obtained from a suitable restriction enzyme treatment of pBR322) for *E. coli*, yeast 2μ plasmid and yeast chromosomal DNA for yeast, plasmid pRSVneo ATCC 37198, plasmid pSV2dhfr ATCC 37145, plasmid pdBPV-MMTneo ATCC 37224, and plasmid pSV2neo ATCC 37149 for mammalian cells.

The enhancer sequence may include the enhancer sequence (72 b.p.) of SV40.

The polyadenylation site may include the polyadenylation site of SV40.

The splicing junction may include the splicing junction of SV40.

The promoter, initiation codon, DNA encoding amino acid sequence of the new CC acylase, termination codon(s) and terminator region can consecutively and circularly be linked together with an adequate replicatable unit (plasmid), if desired, using (an) adequate DNA fragment(s) (e.g. linker, other restriction site, etc.) in a conventional manner (e.g. digestion with restriction enzyme, ligation using T4 DNA ligase) to give an expression vector.

A host cell can be transformed (transfected) with the expression vector. Transformation (transfection) can be carried out in a conventional manner [e.g. Kushner method for *E. coli*, calcium phosphate method for mammalian cells, microinjection, etc.] to give a transformant (transfectant).

For the production of the new CC acylase by the process of this invention, the thus obtained transformant comprising the expression vector is cultured in an aqueous nutrient medium.

The nutrient medium may contain carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extract, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin B1), antibiotics (e.g. ampicillin, kanamycin), etc.] may be added to the medium. For the culture of mammalian cells, Dulbecco's Modified Eagle's Minimum Essential Medium (DMEM) supplemented with fetal calf serum and an antibiotic is often used.

The culture of the transformant (including transfectant) is usually carried out at pH 5.5–8.5 (preferably pH 7–7.5) and 18°–40° C. (preferably 20°–30° C.) for 5–50 hours.

When the thus produced new CC acylase exists in the culture solution, culture filtrate (supernatant) is obtained by filtration or centrifugation of the cultured broth. From the culture filtrate, the new CC acylase can be purified in a conventional manner generally employed for the purification and isolation of natural or synthetic proteins (e.g. dialysis, gel filtration, affinity column chromatography using anti-CC acylase monoclonal antibody, column chromatography on a suitable adsorbent, high performance liquid chromatography, etc.). When the produced new CC acylase exists in periplasm and cytoplasm of the cultured transformant, the cells are collected by filtration and centrifugation, and the cell wall and/or cell membrane thereof are(is) destroyed by, for example, treatment with super sonic waves and/or lysozyme to give debris and/or lysate. The debris and/or lysate can be dissolved in a suitable aqueous solution (e.g. 8M aqueous urea, 6M aqueous quanidium salts). From the solution, the new CC acylase can be purified in a conventional manner as exemplified above.

This invention further provides a process for the preparation of a compound of the formula:

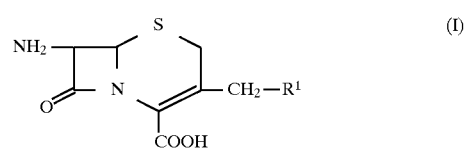

wherein $R^1$ is acetoxy its salt, or hydrogen, or its salt, which comprises contacting a compound of the formula:

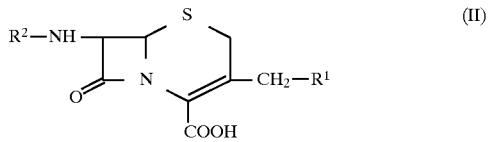

wherein $R^1$ is as defined above and
$R^2$ is carboxylic acyl, or its salt,
with the cultured broth of a microorganism transformed with an expression vector comprising DNA encoding the new CC acylase of this invention or its processed material.

The carboxylic acyl for $R^2$ may include aliphatic, aromatic or heterocyclic carboxylic acyl and suitable example thereof may be $C_1$–$C_6$ alkanoyl which may have one or two suitable substituent(s) selected from the group of amino, hydroxy, carboxy, $C_1$–$C_6$ alkanoylamino, benzamido, thienyl, and the like.

Suitable salt of the compounds (I) and (II) may be alkali metal salt (e.g. sodium salt, potassium salt, lithium salt).

If the CC acylase activity usually exists in transformed cells, the following preparations can be exemplified as a processed material of the cultured broth.
(1) Raw cells: separated from the cultured broth in a conventional manner such as filtration and centrifugation;
(2) dried cells: obtained by drying said raw cells in a conventional manner such as lyophilization and vacuum drying;
(3) cell-free extract: obtained by destroying said raw or dried cells in a conventional manner (e.g. autolysis of the cells using an organic solvent, grinding the cells with alumina, sea sand, etc. or treating the cells with super sonic waves);
(4) enzyme solution: obtained by purification or partial purification of said cell-free extracts in a conventional manner (e.g. column chromatography); and
(5) immobilized cells or enzyme: prepared by immobilizing said cells or enzyme in a conventional manner (e.g. a method using acrylamide, glass bead, ion exchange resin, etc.).

The reaction comprising a contact of the compound (II) with the enzyme can be conducted in an aqueous medium such as water or a buffer solution, that is, it can be usually conducted by dissolving or suspending the cultured broth or its processed material in an aqueous medium such as water or a buffer solution containing the compound (II).

Preferable pH of the reaction mixture, concentration of the compound (II), reaction time and reaction temperature may vary with properties of the cultured broth or its processed material to be used. Generally, the reaction is carried out at pH 6 to 10, preferably pH 7 to 9, at 5° to 40° C., preferably 5° to 37° C. for 0.5 to 50 hours.

The concentration of the compound (II) as a substrate in the reaction mixture may be preferably selected from the range of from 1 to 100 mg/ml.

The thus produced compound (I) can be purified and isolated from the reaction mixture in a conventional manner.

Specific activities of mutant acylases were determined according to the procedure mentioned below.
i) GL-7ACA acylase activity
To 500 μl of GL-7ACA solution [10 mg/ml in 0.15M Tris.HCl (pH 7.5)] that was pre-incubated at 37° C. for 10 min, 20 μl of sample acylase was added and the mixture was incubated at 37° C. for 5 min. The reaction was stopped by the addition of 550 μl of 5% acetic acid. After centrifugation (10,000 rpm for 5 min at ambient temperature) of the resulting mixture, the supernatant was used for the assay of 7ACA formation.

HPLC conditions: column: TSKgel ODS-80 TMCTR 4.4 mm×100 mm (TOSOH); eluate: 100 mM citric acid, 5.0 mM sodium n-hexane-1-sulfonate in 14.3% (V/V) acetonitrile; flow rate: 1.0 ml/min; injection volume: 10 μl; detector: 254 nm.

One unit was defined as the activity capable of synthesizing 1.0 μmole of 7ACA from GL-7ACA per minute at 37° C.
ii) CC acylase activity
To 500 μl of CC solution [10 mg/ml sodium salt of cephalosporin C in 0.15M Tris.HCl (pH 8.7), pH was readjusted with 1N NaOH to pH 8.7] that was pre-incubated at 37° C. for 10 min, 20 μl of a sample acylase was added and the mixture was incubated at 37° C. for 10 min. The reaction was stopped by the addition of 550 μl of 5% acetic acid. After centrifugation (10,000 rpm for 5 min at ambient temperature) of the resulting mixture, the supernatant was used for the assay of 7ACA formation.

HPLC conditions: column: TSKgel ODS-80 TMCTR 4.4 mm×100 mm (TOSOH), eluate: 100 mM citric acid, 5.0 mM sodium n-hexane-1-sulfonate in 14.3% (V/V) acetonitrile; flow rate: 1.0 ml/min;
injection volume: 20 μl; detector: 254 nm.

One unit was defined as the activity capable of synthesizing 1.0 μmole of 7ACA from sodium salt of Cephalosporin C per minute at 37° C.

Brief explanation of the accompanying drawings is as follows.

FIG. 1 shows DNA oligomers used in the working Examples of this Specification (SEQ ID NO:1–42).

FIG. 22 shows the nucleotide and amino acid sequences of mutant CC acylase M164A (SEQ ID NO:43,44).

FIG. 23 shows the nucleotide and amino acid sequences of mutant CC acylase S166A (SEQ ID NO:45,46).

FIG. 24 shows the nucleotide and amino acid sequences of mutant CC acylase M269I/E358K (SEQ ID NO:47,48).

FIG. 25 shows the nucleotide and amino acid sequences of mutant CC acylase M164L/M174A/M269Y (SEQ ID NO:49,50).

FIG. 26 shows the nucleotide and amino acid sequences of mutant CC acylase A49L (SEQ ID NO:51,52).

Figure 2A:
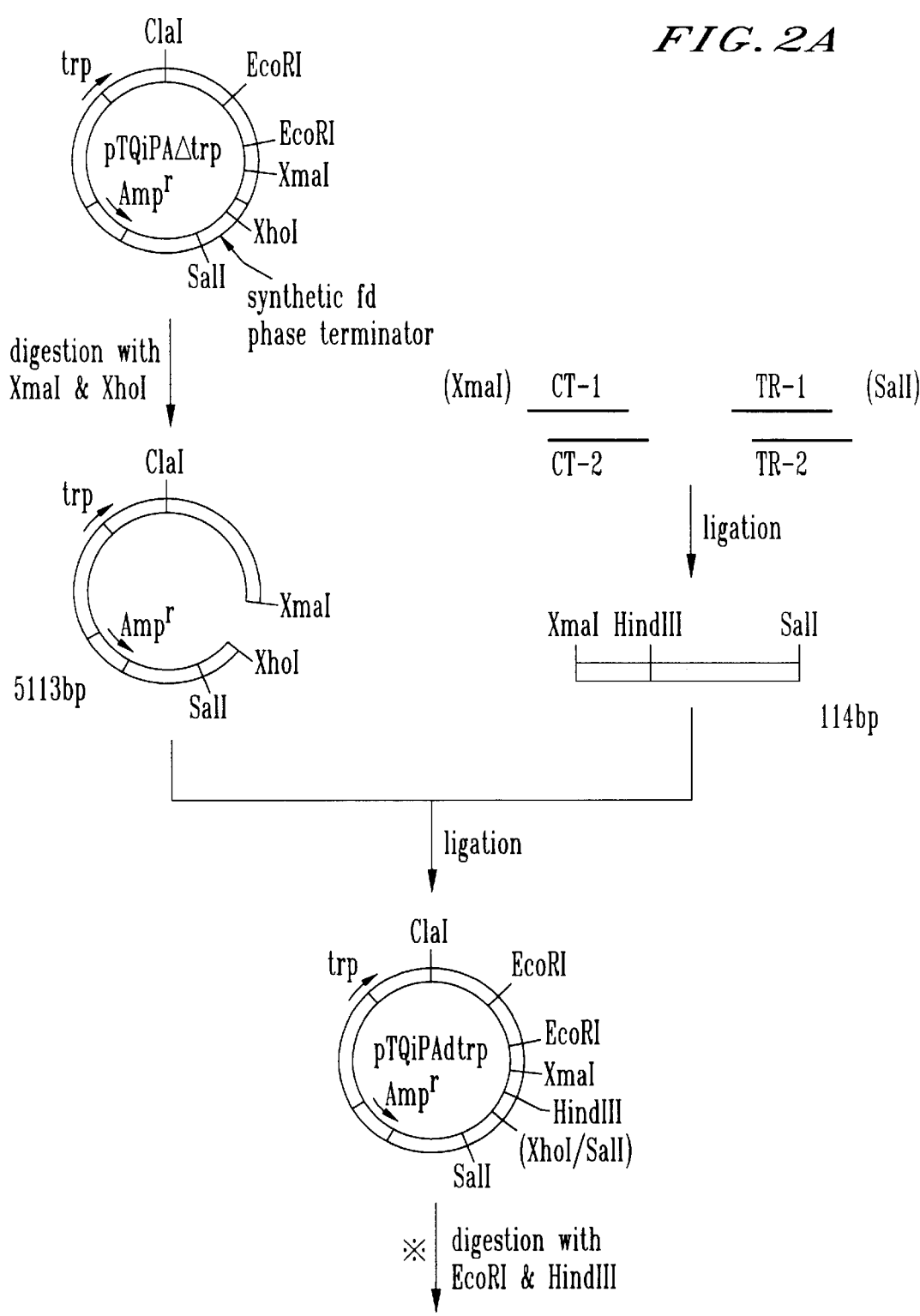
FIG. 2 is a schematic presentation of the construction of pCC001A.
Figure 2B:
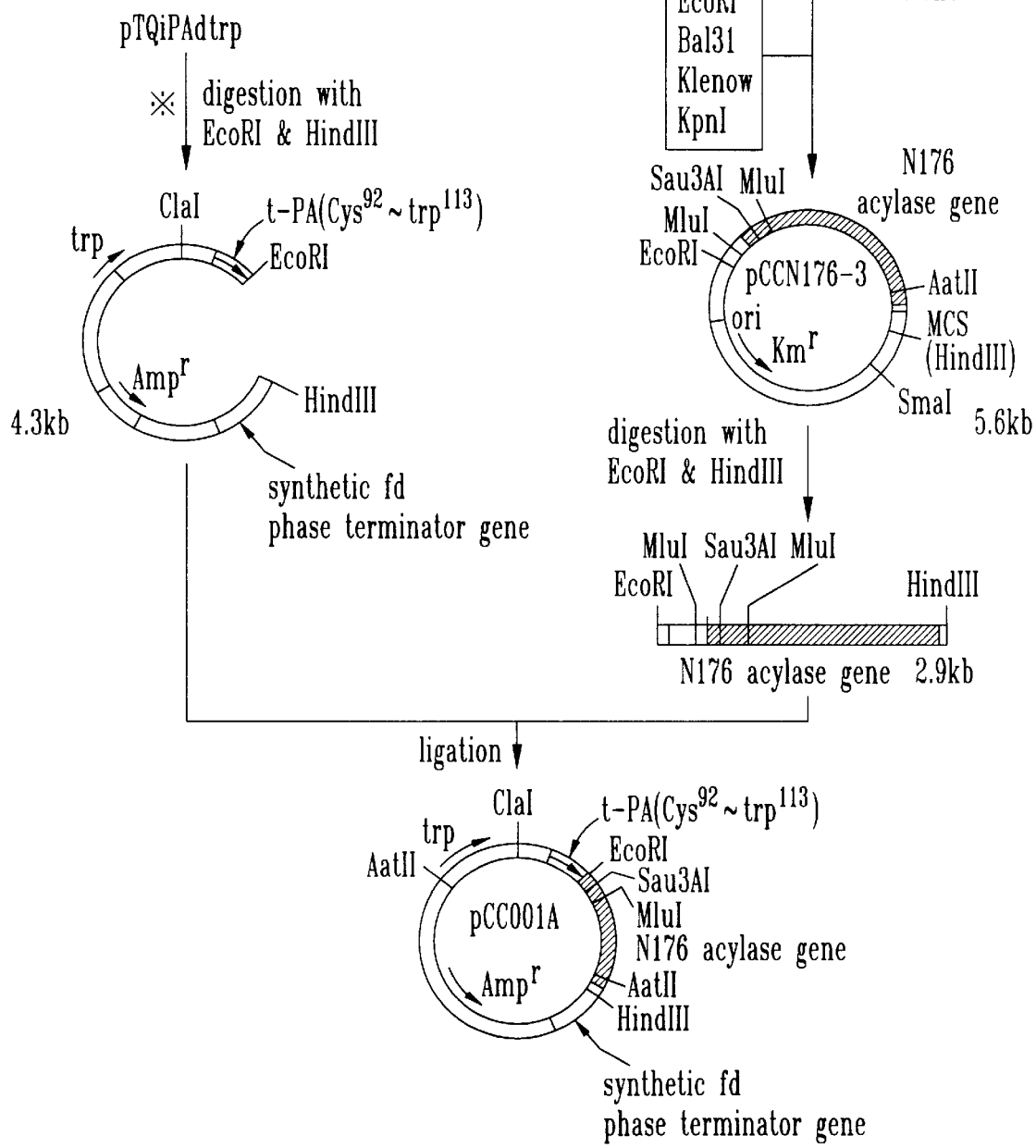
Figure 3:
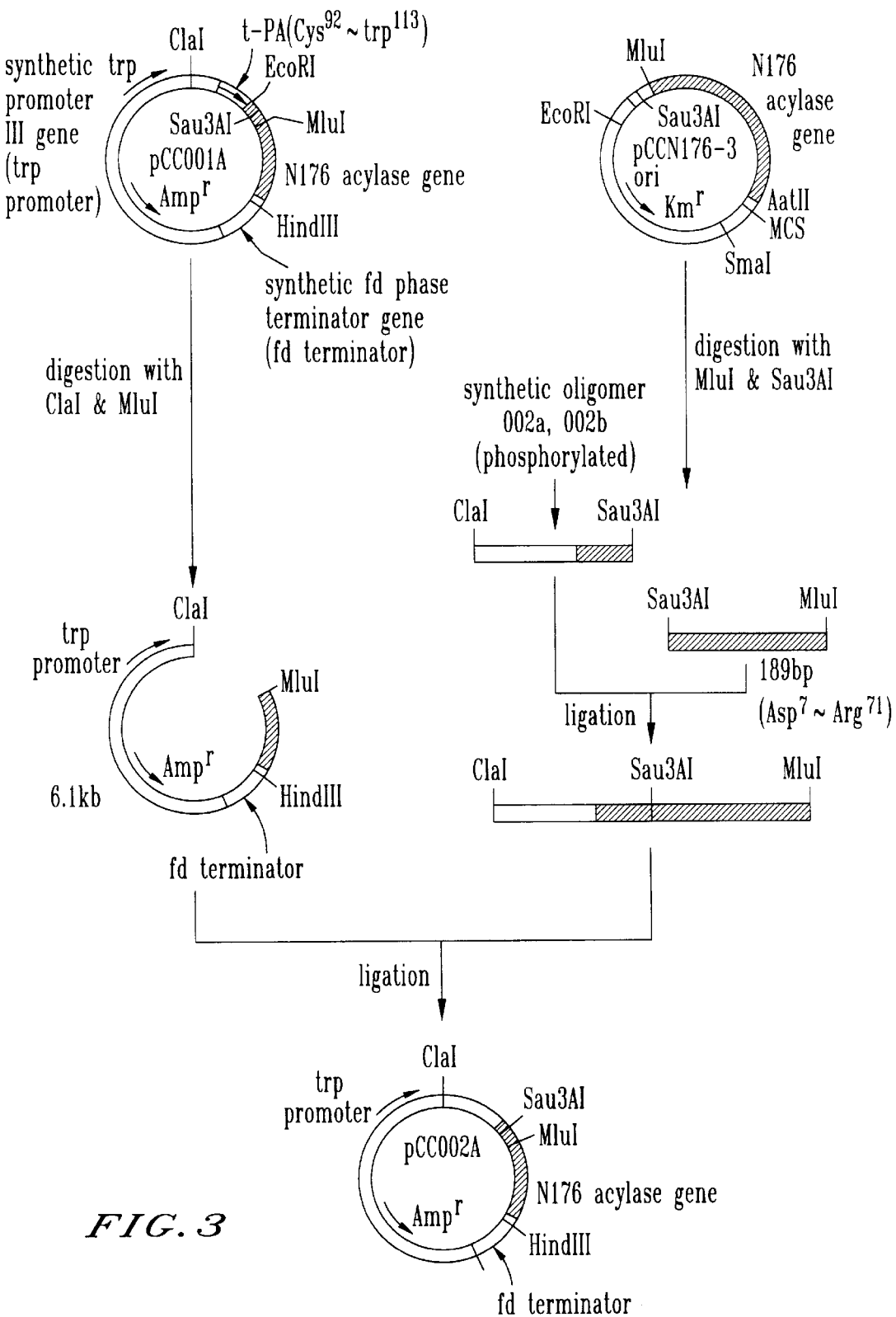
FIG. 3 is a schematic presentation of the construction of pCC002A.
Figure 4:
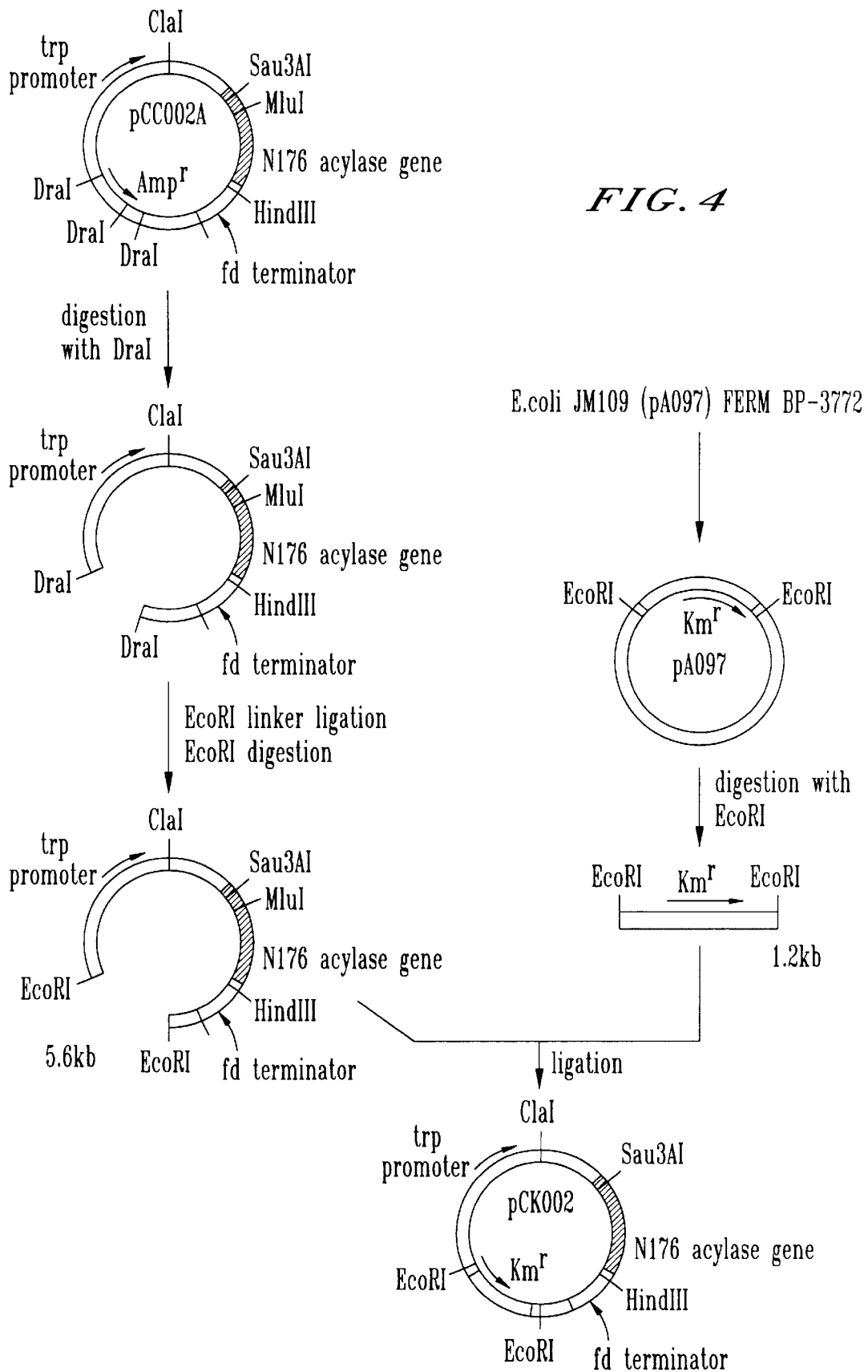
FIG. 4 is a schematic presentation of the construction of pCK002.
Figure 5:
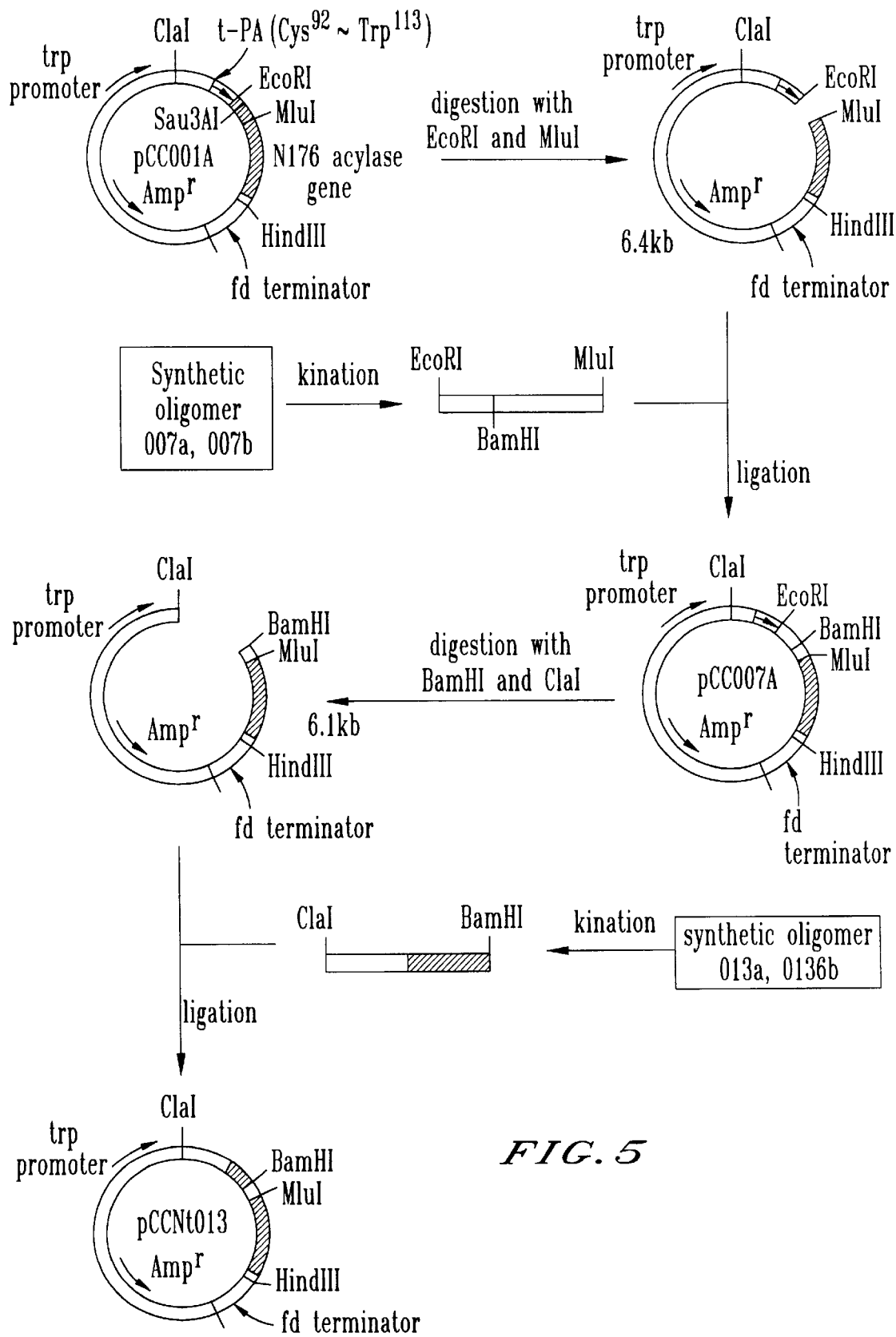
FIG. 5 is a schematic presentation of the construction of pCC007A and pCCNt013.
Figure 6:
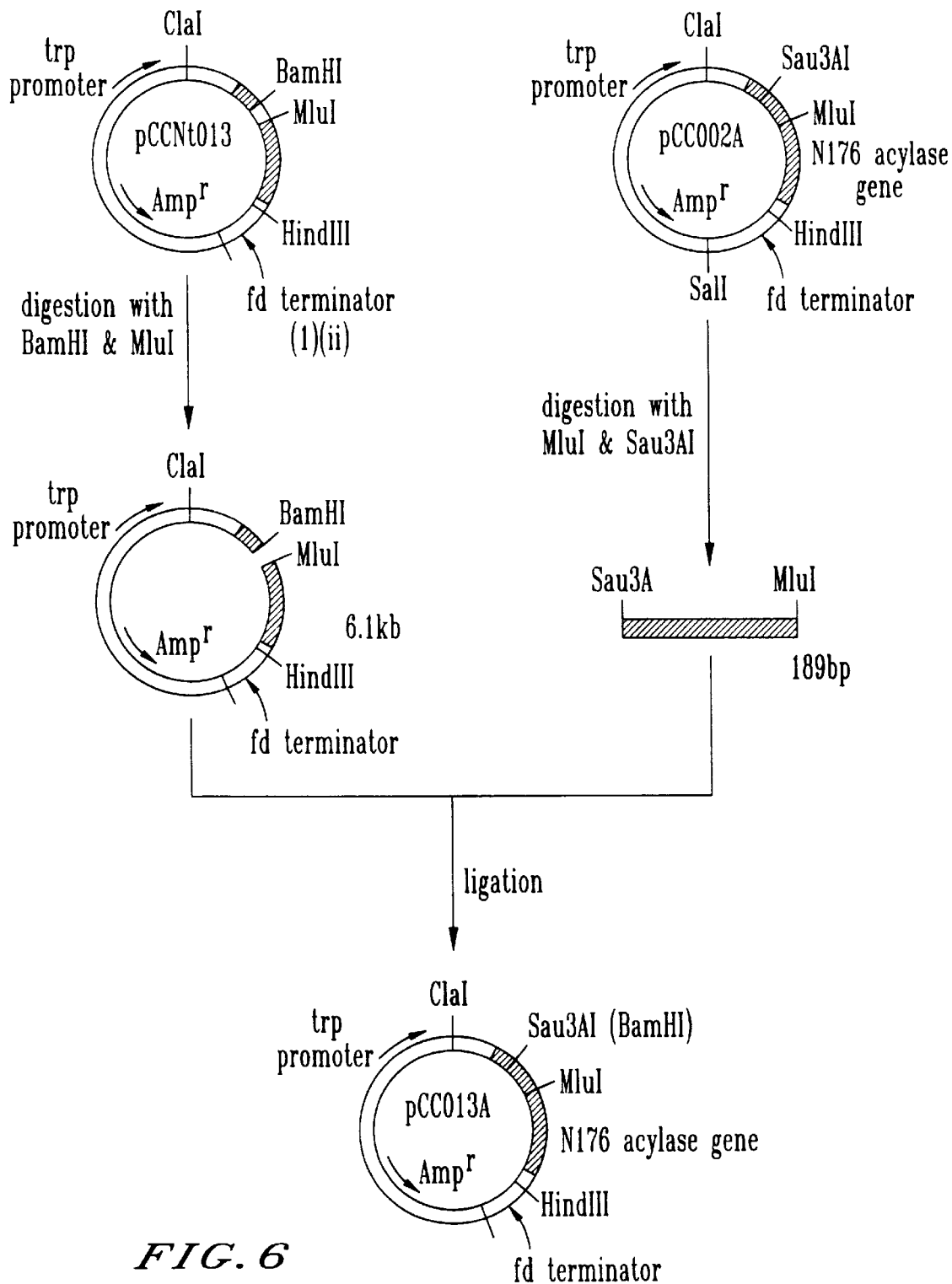
FIG. 6 is a schematic presentation of the construction of pCC013A.
Figure 7:
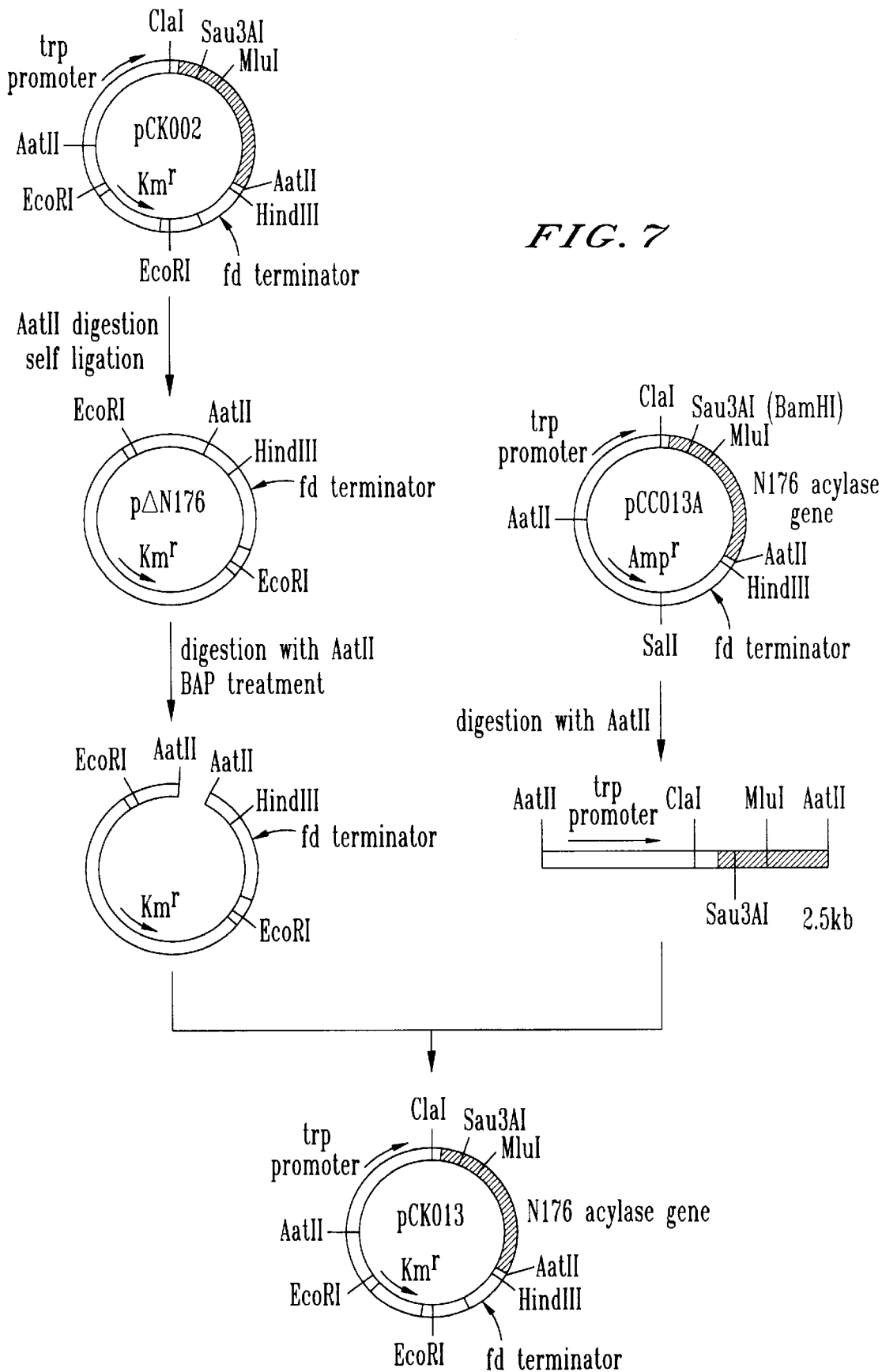
FIG. 7 is a schematic presentation of the construction of pΔN176 and pCK013.
Figure 8:
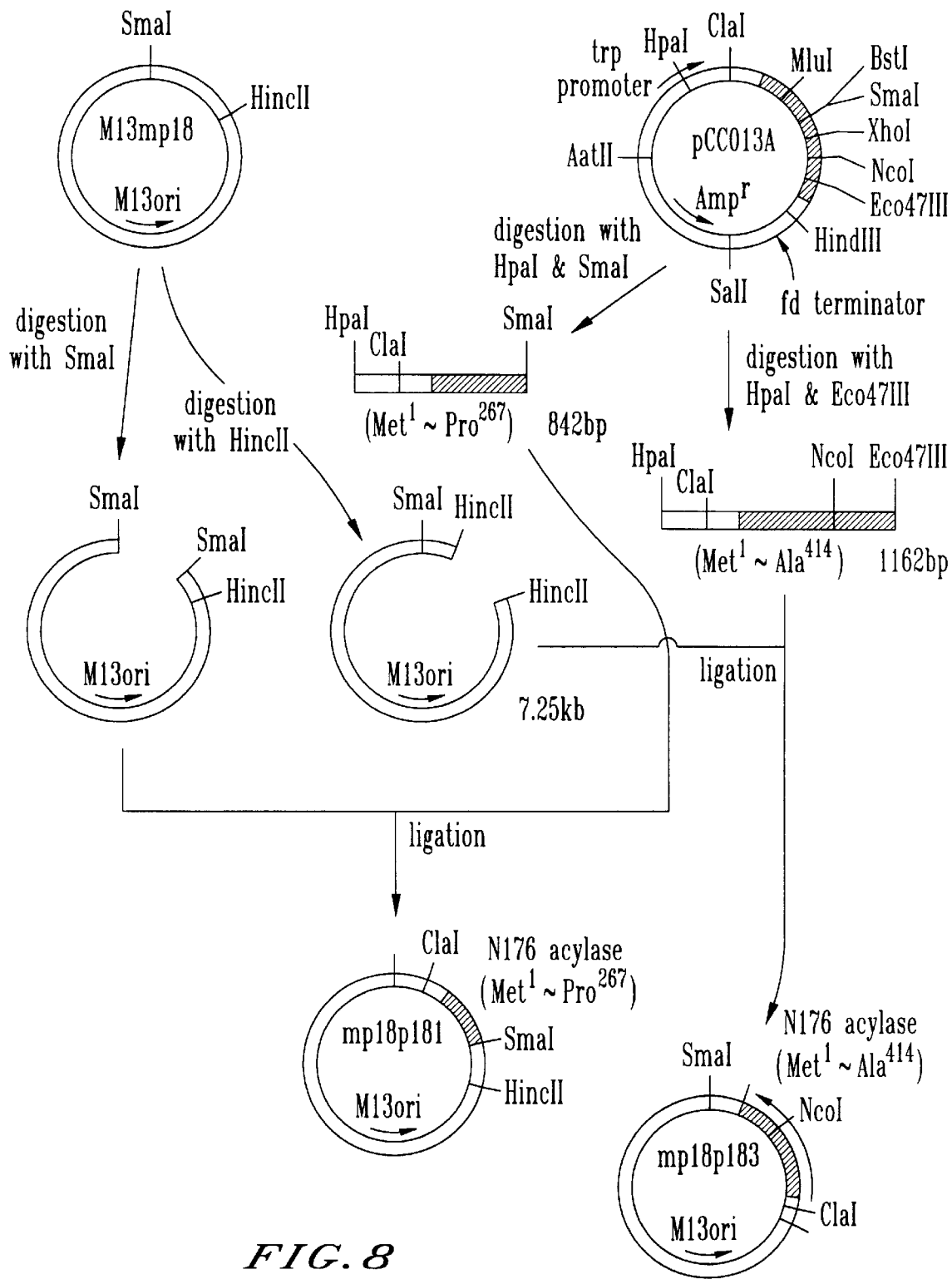
FIG. 8 is a schematic presentation of the preparation of mp18p181 and mp18p183.
Figure 9:
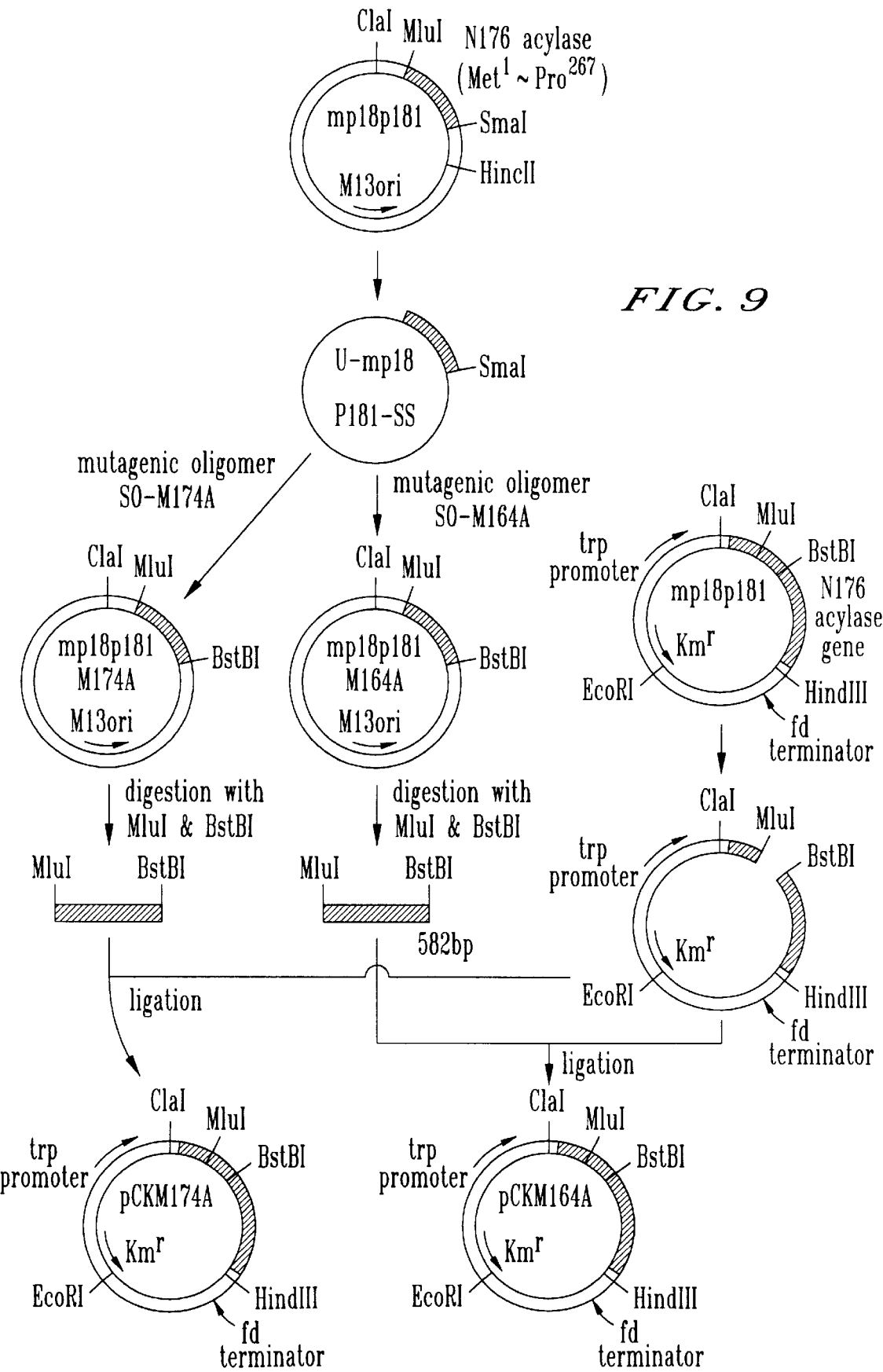
FIG. 9 is a schematic presentation of the preparation of mp18p181M164A, mp18p181M174A, pCKM174A and pCKM164A.
Figure 10:
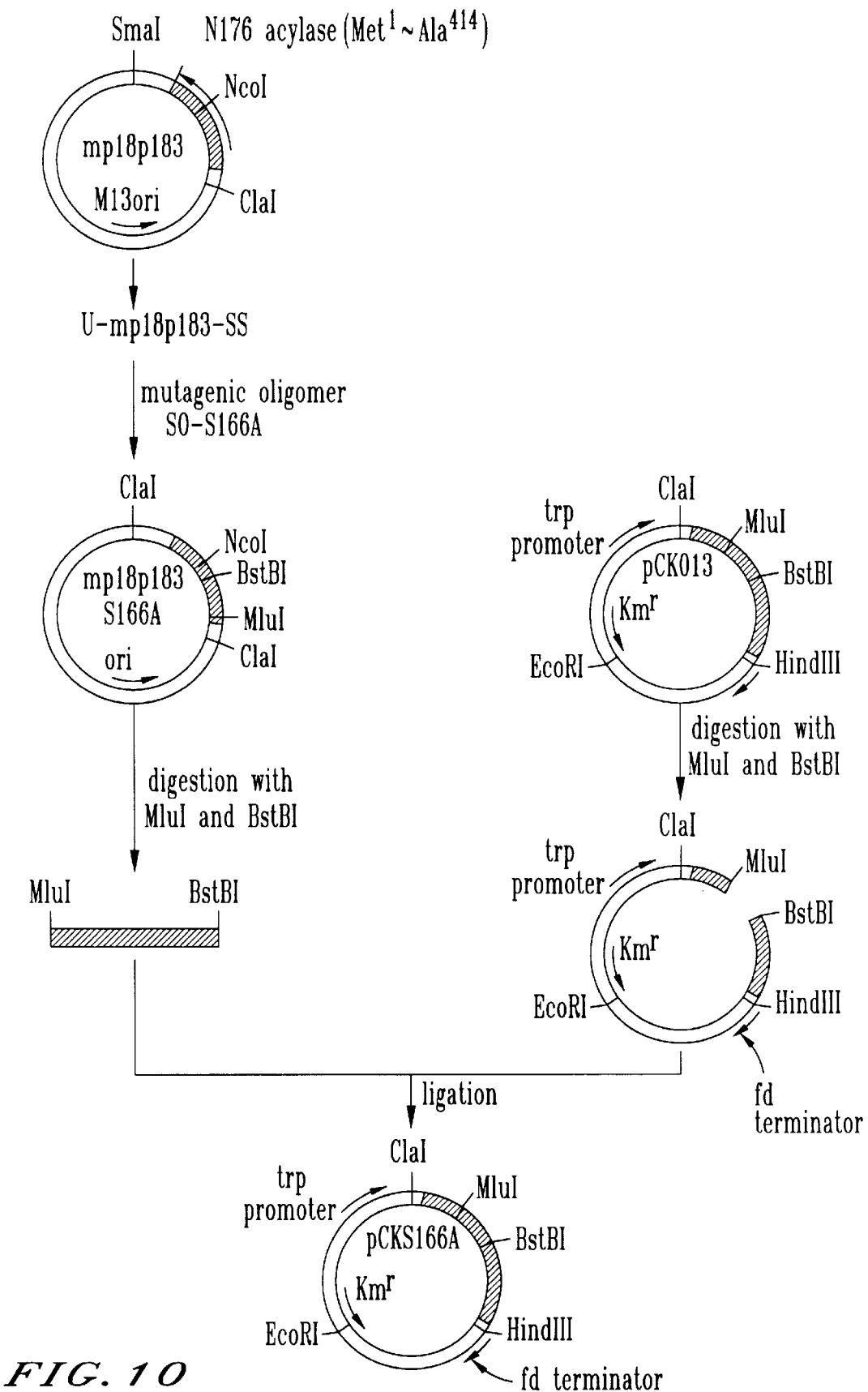
FIG. 10 is a schematic presentation of the preparation of pCKS166A.
Figure 11:
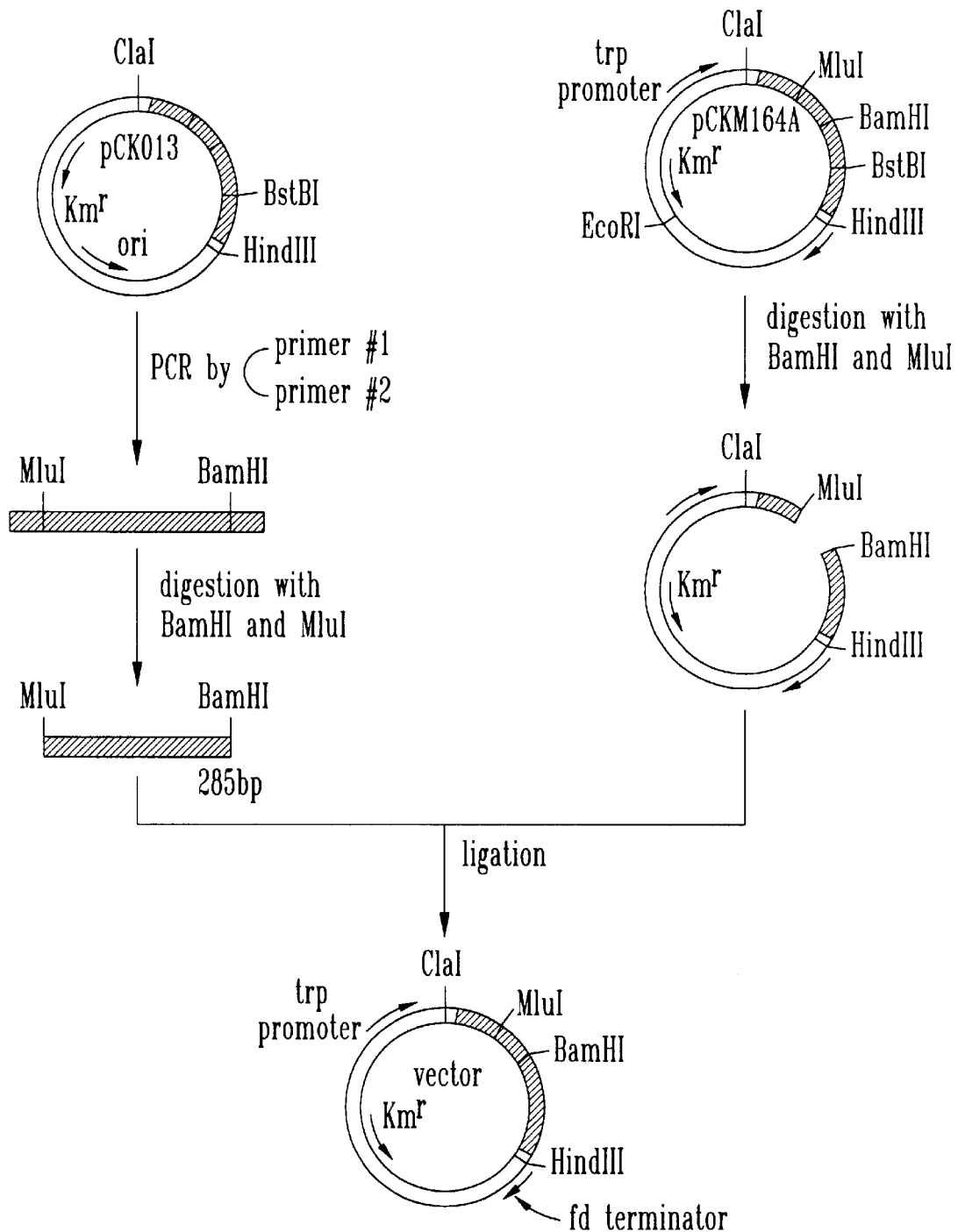
FIG. 11 is a schematic presentation of the preparation of pCKM164L and pCKM164G.
Figure 12:
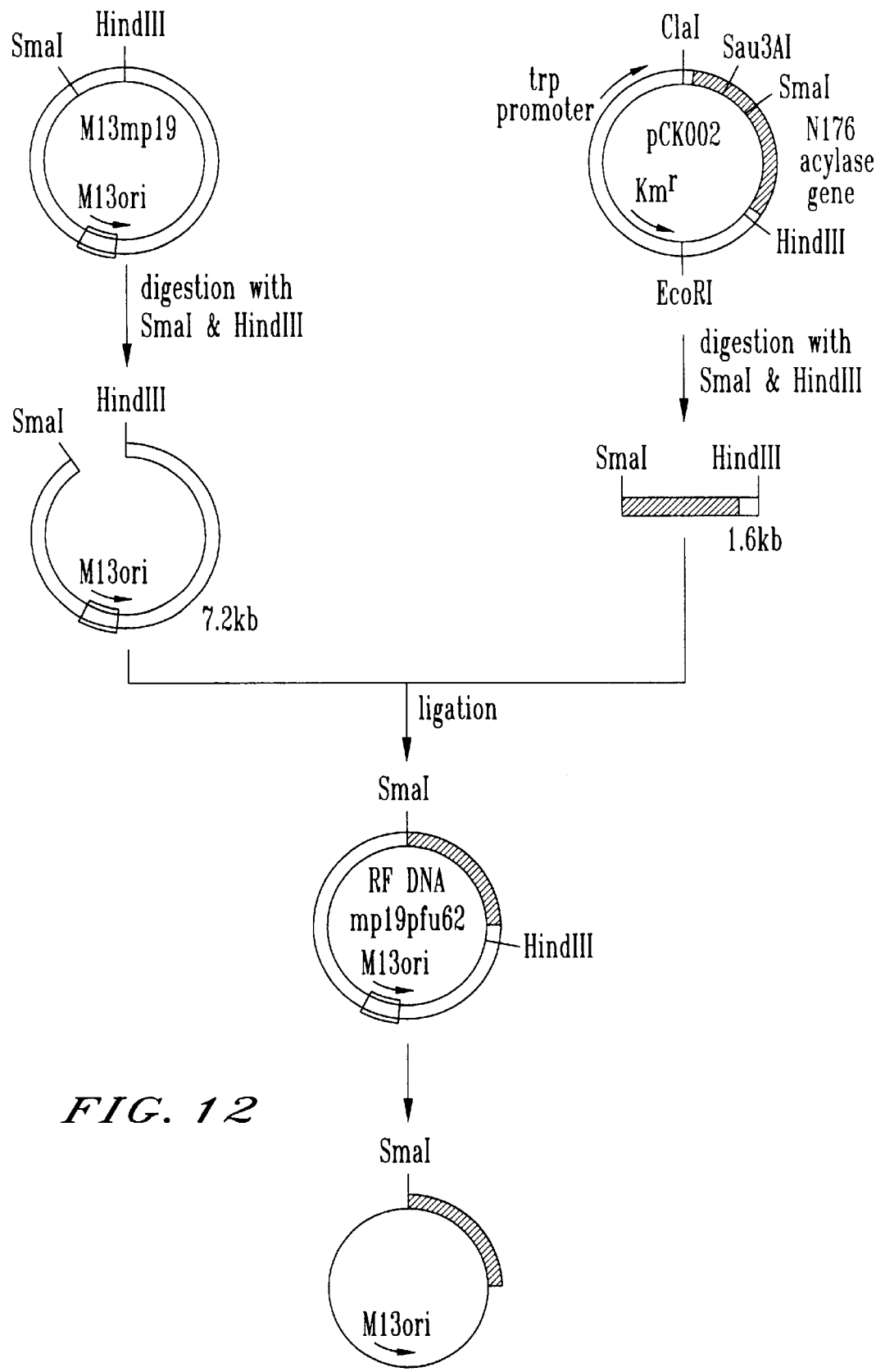
FIG. 12 is a schematic presentation of the construction of mp19pfu62.
Figure 13:
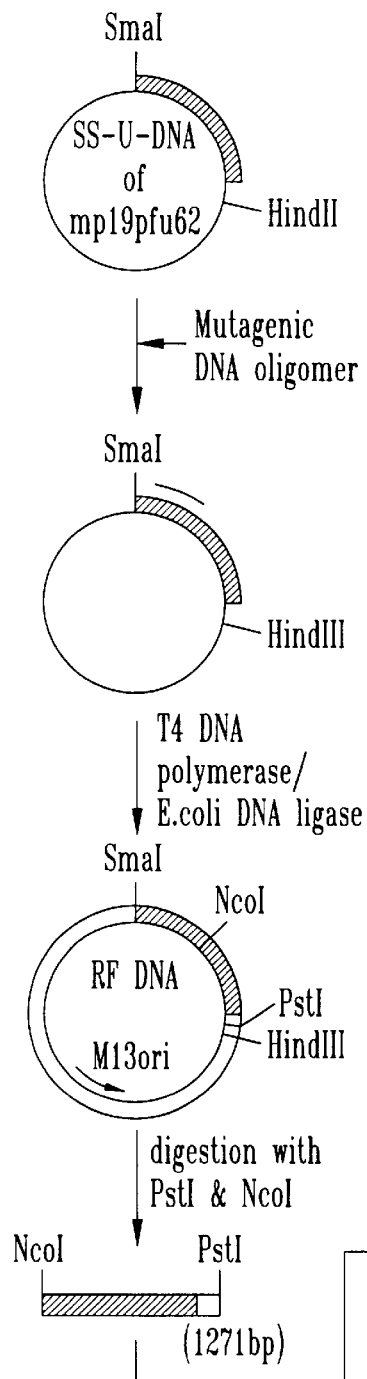
FIG. 13 is a schematic presentation of the preparation of RF DNAs (mp19pfu62M465A, mp19pfu62M506A and mp19pfu62M750A) and expression vectors (pCKM465A, pCKM506A and pCKM750A).
Figure 13:
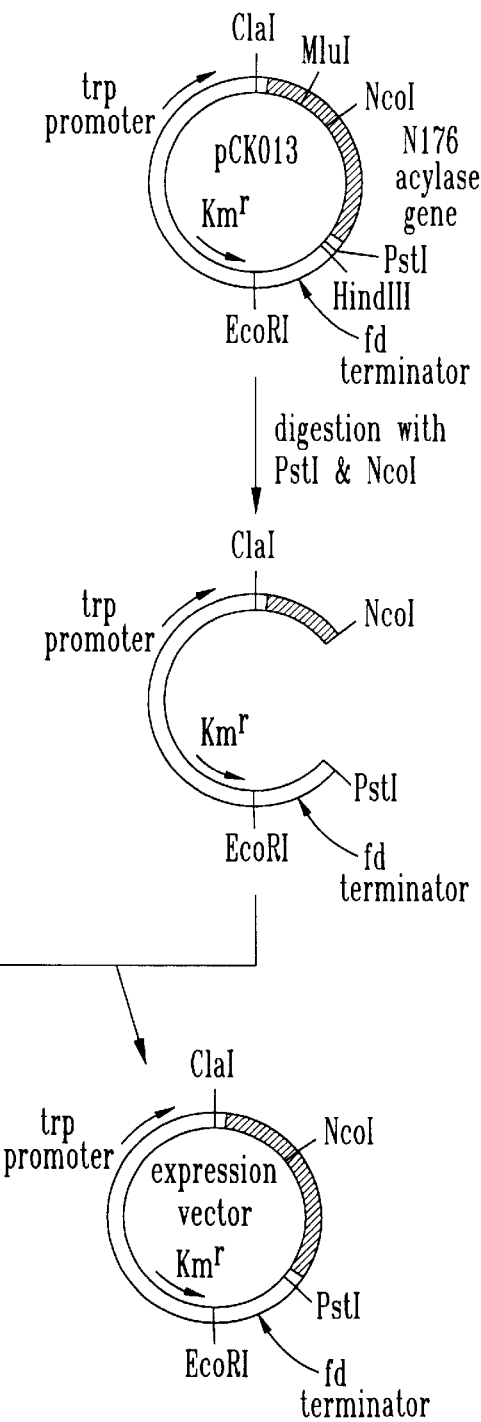
Figure 14:
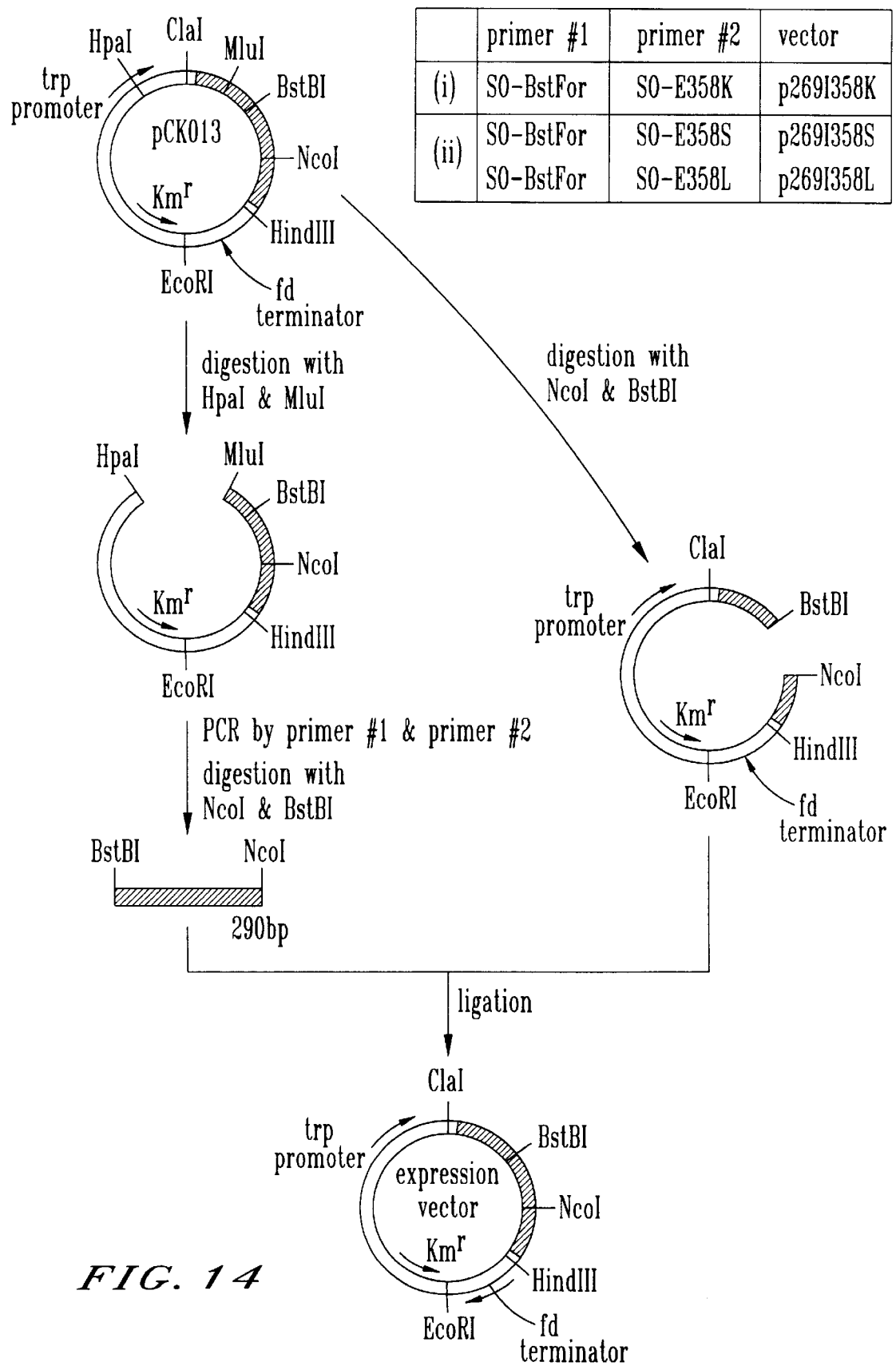
FIG. 14 is a schematic presentation of the preparation of p269I358K, p269I358S and p269I358L.
Figure 15:
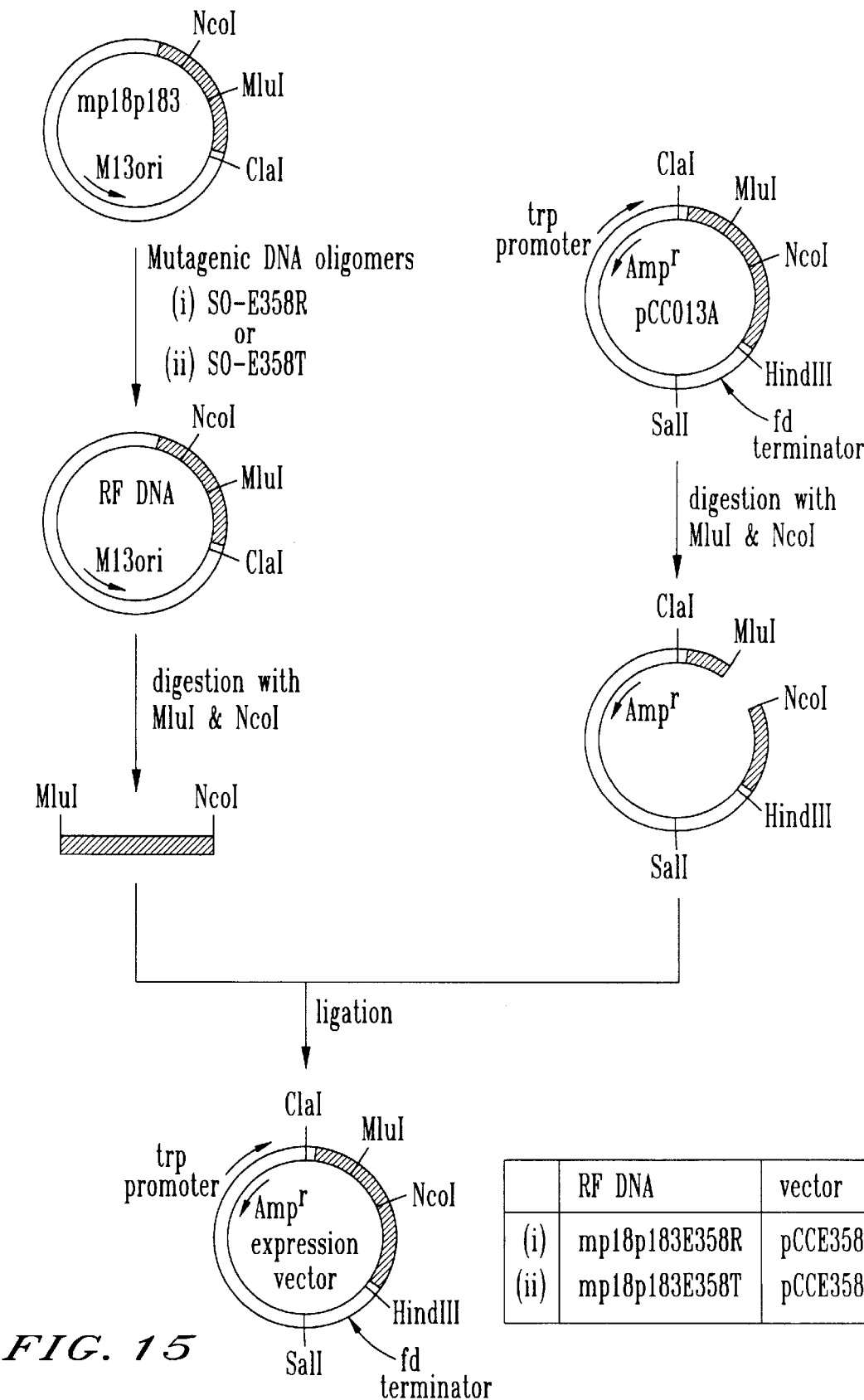
FIG. 15 is a schematic presentation of the preparation of pCCE358R and pGCE358T.
Figure 16:
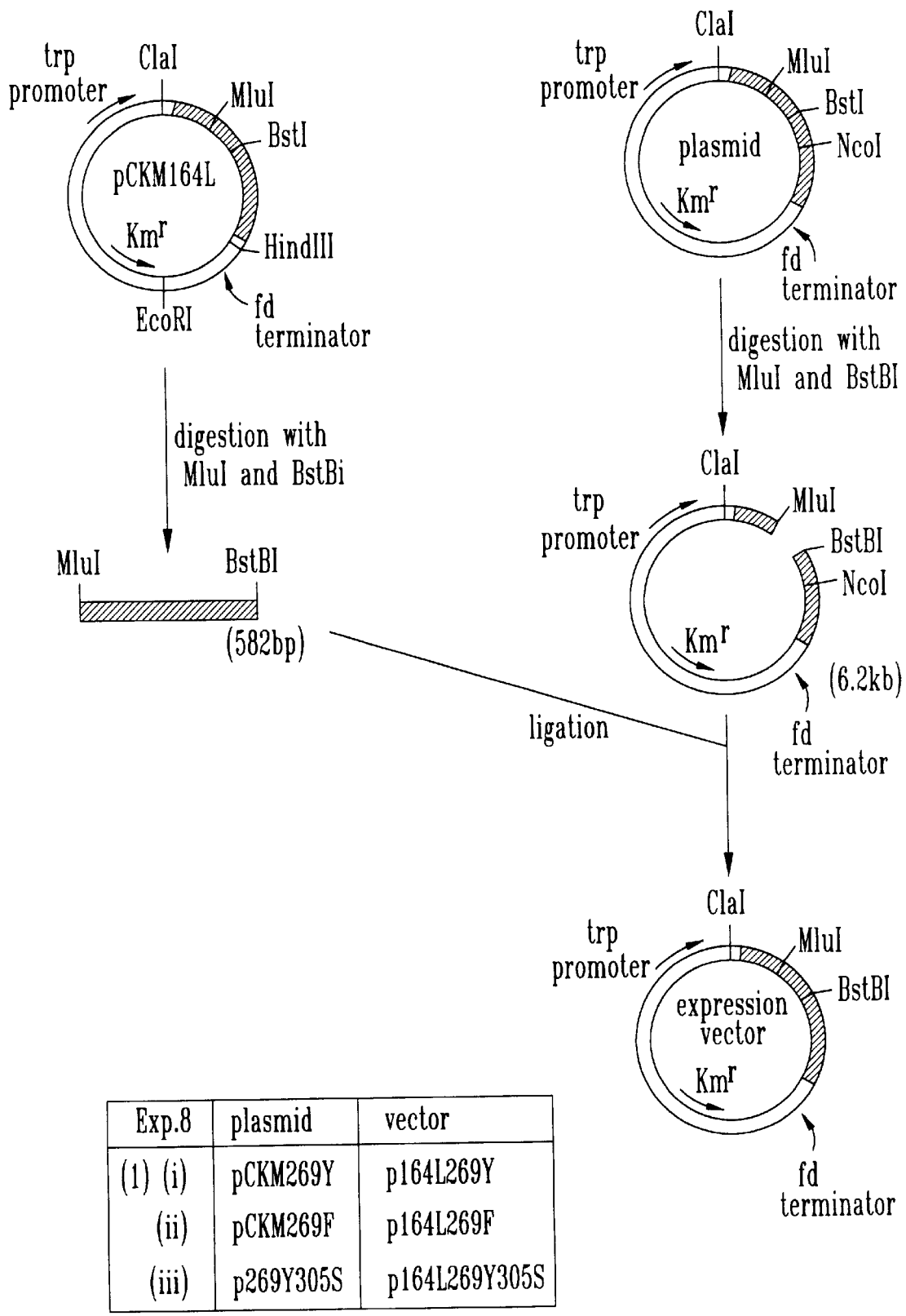
FIG. 16 is a schematic presentation of the preparation of p164L269Y, p164L269F and p164L269Y305S.
Figure 17:
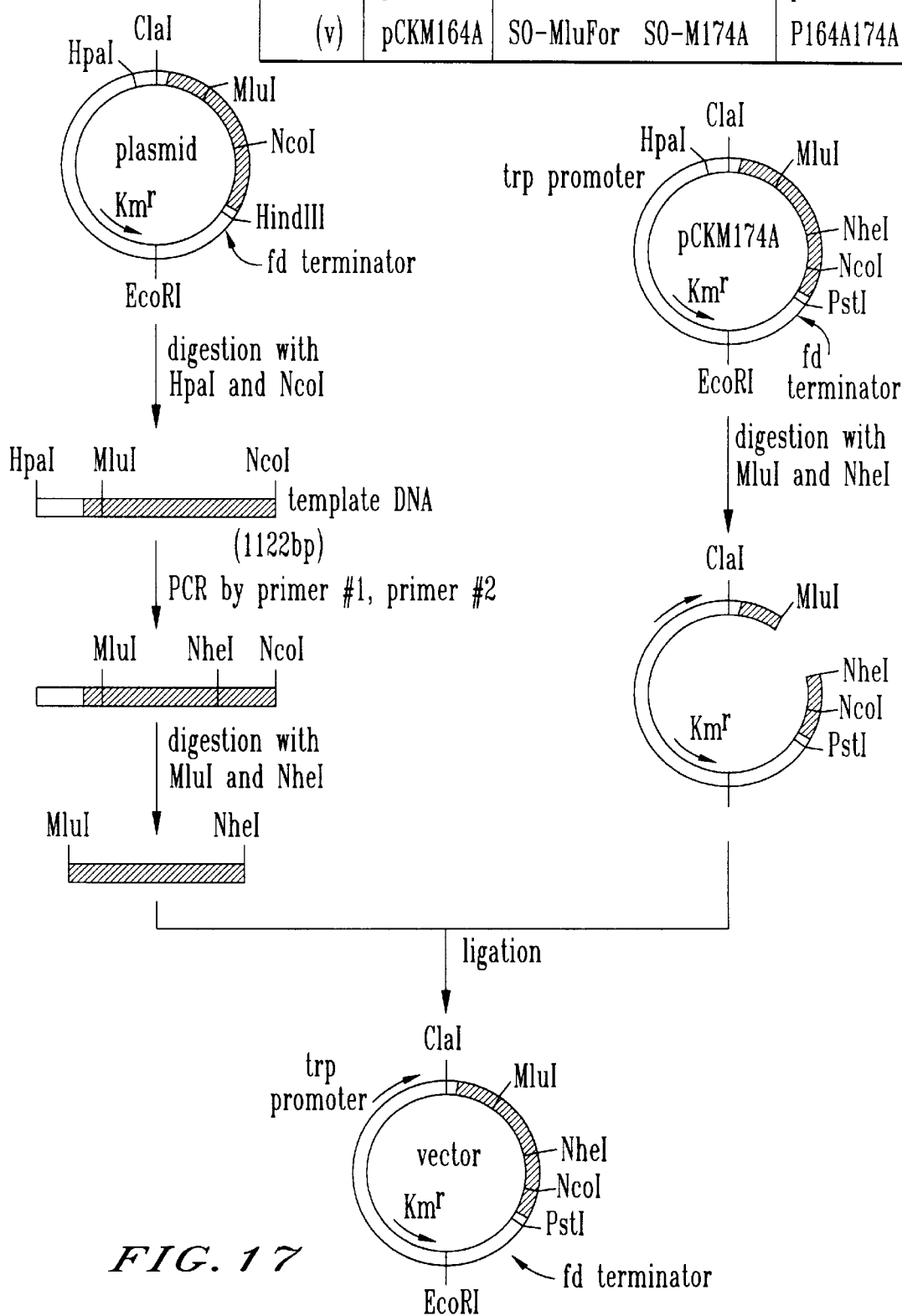
FIG. 17 is a schematic presentation of the preparation of p164L174A and p164A174A.
Figure 18:
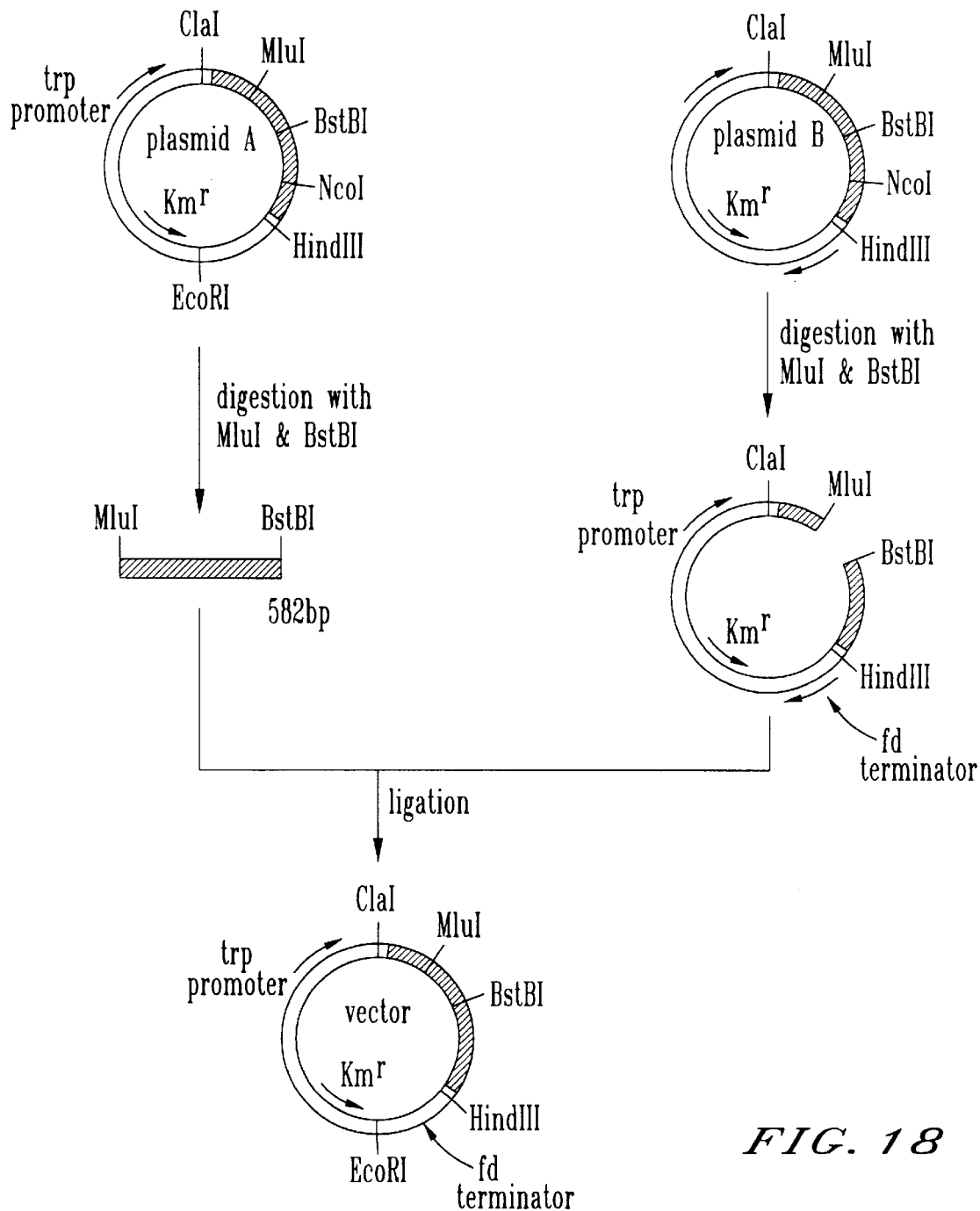
FIG. 18 is a schematic presentation of the preparation of p164A269Y, p164L174A269Y, p164L174A269F, p164A174A269Y305S.
Figure 19:
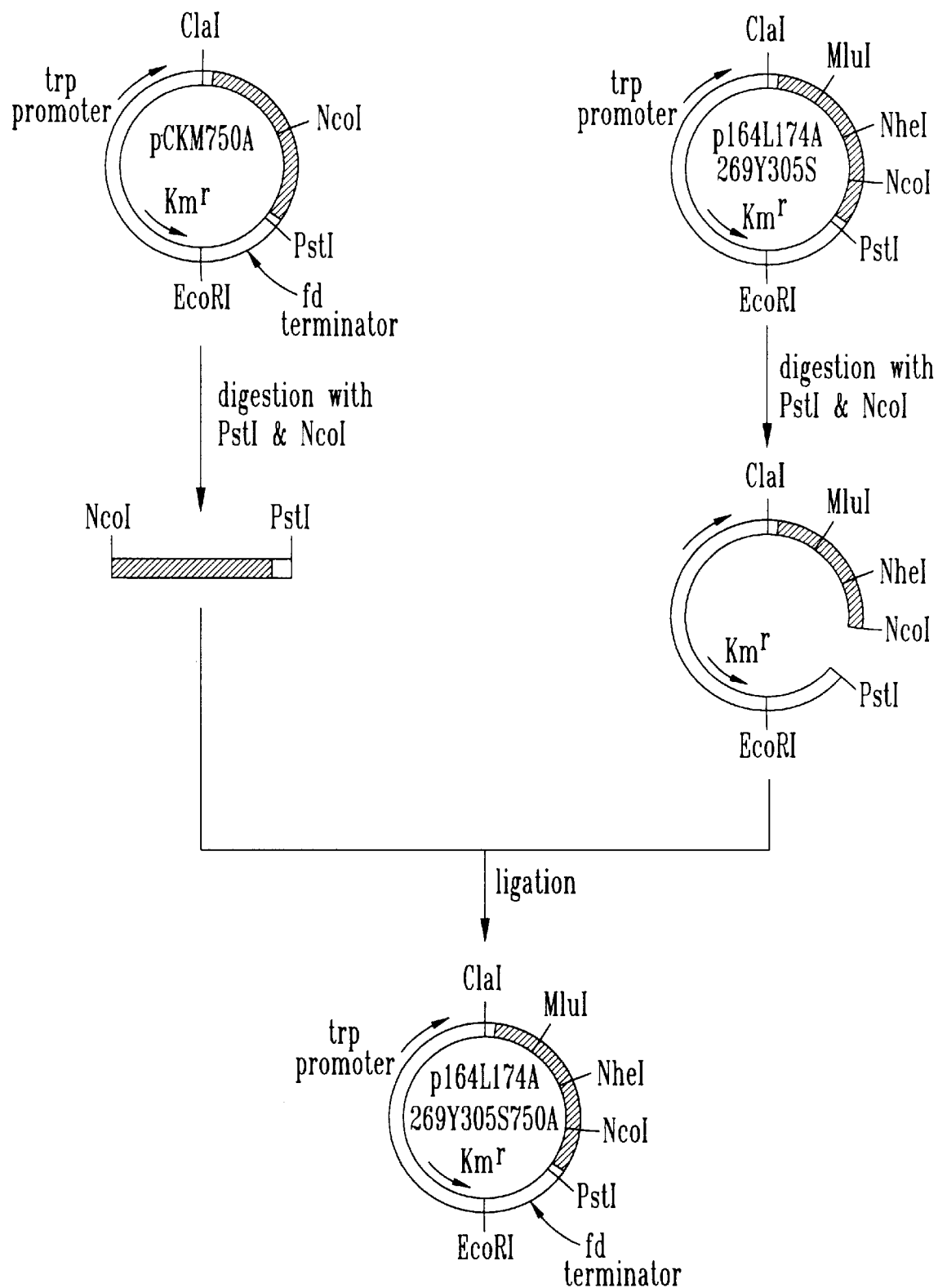
FIG. 19 is a schematic presentation of the preparation of p164L174A269Y305S750A.
Figure 20:
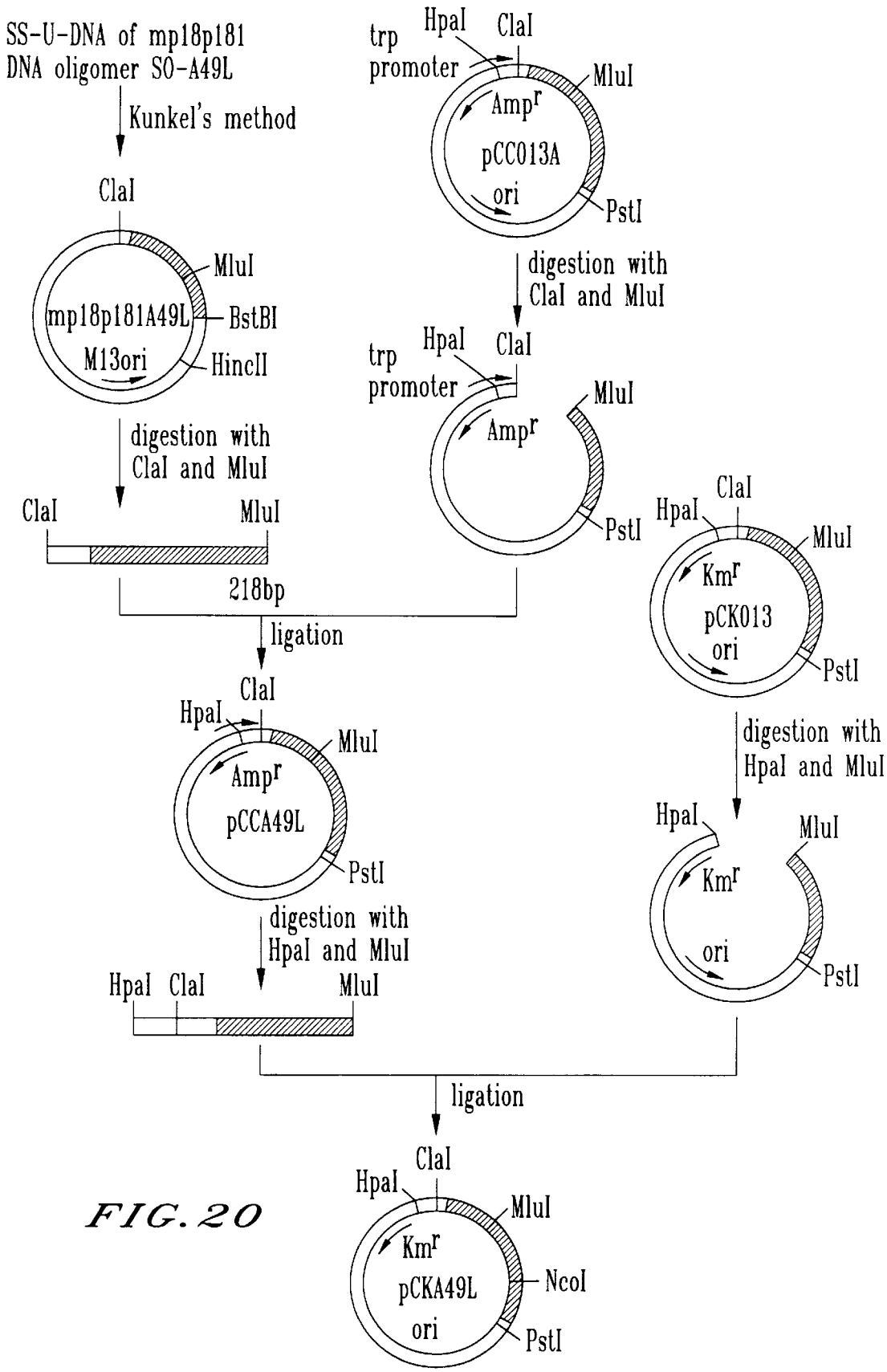
FIG. 20 is a schematic presentation of the preparation of pCKA49L.
Figure 21:
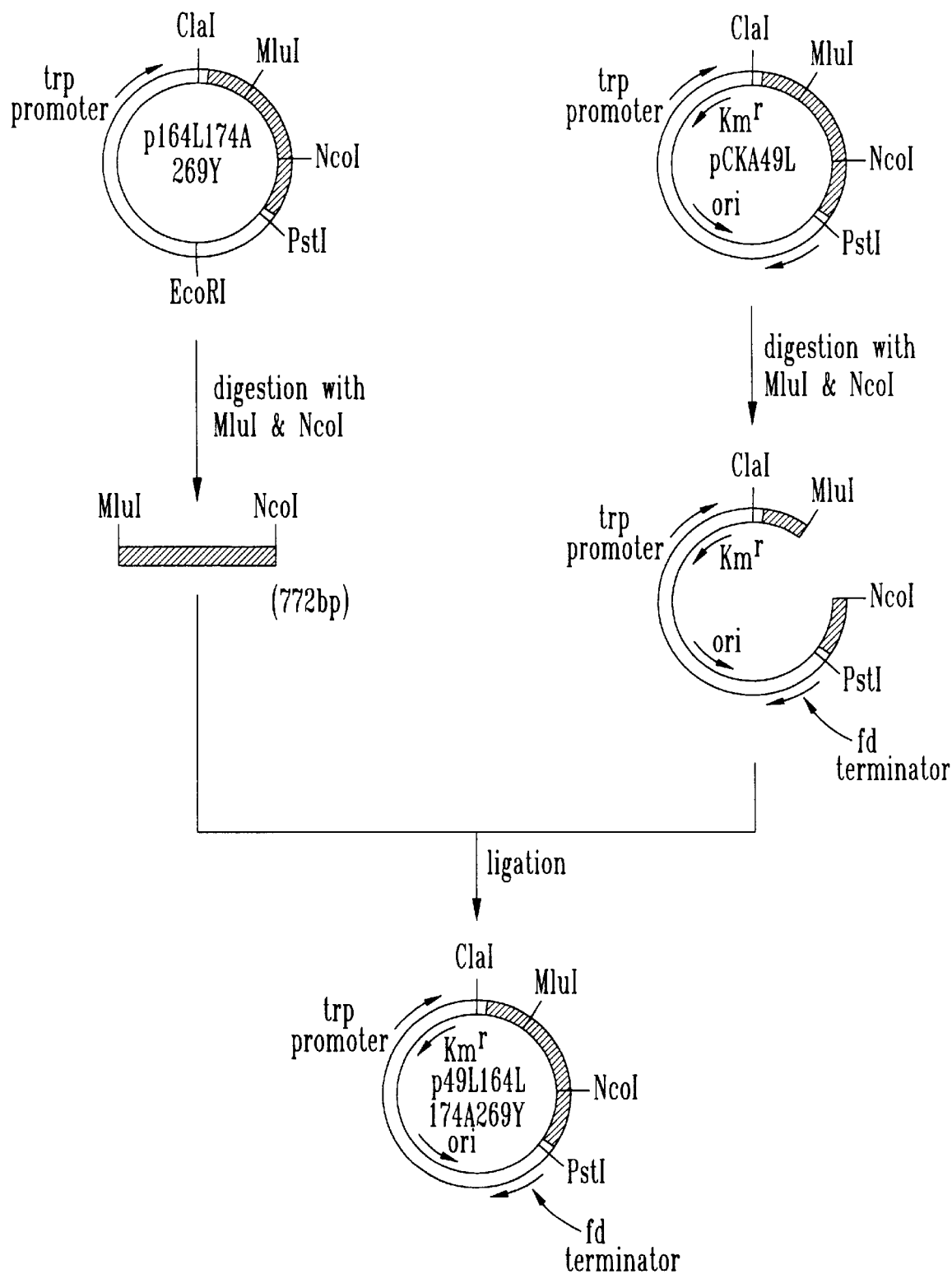
FIG. 21 is a schematic presentation of the preparation of p49L164L174A269Y.

In the following Examples, some plasmids, enzymes, such as restriction enzymes, T4 DNA ligases, and other materials were obtained from commercial sources and used according to the indication by suppliers. In particular, plasmid pCCN176-2 and plasmid pTQiPAΔtrp used as starting materials in Examples have been deposited at an international depository, National Institute of Bioscience and Human-Technology, Agency of Industrial Science and Technology in Japan, as transformant *E. coli* JM109 (pCCN176-2) FERM BP-3047 and transformant *E. coli* HB101-16 (pTQiPAΔtrp) FERM BP-1870, respectively, and can be easily obtained based on U.S. Pat. No. 5,192,678 and European Patent Application Publication No. 302456. Other plasmid etc. can be easily prepared according to the description in the specification, from said pCCN176-2, pTQiPAΔtrp and those commercially available. Operations employed for the cloning of DNA, transformation of host cells, cultivation of transformants, recovery of the new CC acylase from the cultured broth, and the like are well known in the art or can be adapted from literatures.

The following examples are given for the purpose of illustrating this invention, and the invention is not limited thereto.

EXAMPLE 1

(Synthesis of Oligodeoxyribonucleotide)

A DNA oligomer SO-M164A [as listed in FIG. 1(a)] was synthesized with 381A DNA synthesizer (Applied Biosystems Inc.). The DNA was liberated from CPG polymer support (CPG: controlled pore glass) with 28% aqueous ammonia followed by heating at 60° C. for 9 hours to remove all protection groups (SEQ ID NO:2). The reaction mixture was evaporated in vacuo, and the residue was dissolved in 200 μl of TE buffer [10 mM Tris.HCl (pH 7.4)-1 mM EDTA]. The resulting crude DNA solution was applied to reverse phase HPLC [column; COSMOSIL C18 4.6 mm×150 mm (Nacalai Tesque), eluate; A: 0.1M Triethylammonium acetate buffer (pH 7.2–7.4), B: acetonitrile, gradient; initial A(100%), final A(60%)+B(40%), linear gradient during 25 min, flow rate; 1.2 ml/min]. The eluate containing the objective DNA oligomer was collected and evaporated in vacuo. The purified DNA was dissolved in 200 μl of TE buffer and stored at −20° C. before use.

All other DNA oligomers listed in FIG. 1 were synthesized and purified in a manner similar to that described above.

EXAMPLE 2

(Preparation of Expression Vector for Native CC Acylase N176 Under the Control of trp Promoter)

(1) Construction of pCC002A, an ampicillin resistant expression vector for native CC acylase N176

(i) Construction of pCC001A

Plasmid pCCN176-3 [preparation method of this plasmid from plasmid pCCN176-2 (which is obtainable from a transformant *Escherichia coli* JM109 (pCCN176-2) FERM BP-3047 in a conventional manner) is disclosed in page 235 of JOURNAL OF FERMENTATION AND BIOENGINEERING Vol. 72, 1991] (1.0 μg) was digested with EcoRI and HindIII, and the 2.9 kb fragment carrying the entire coding region of CC acylase N176 was isolated by agarose gel electrophoresis. On the other hand, PTQiPAΔtrp (1.0 μg), an expression vector for a mutant t-PA [which is obtainable from a transformant, *Escherichia coli* HB101-16 (pTQiPAΔtrp) FERM BP-1870 in a conventional manner and a preparation method of which is disclosed in European Patent Application Publication No. 3024561] was digested with XmaI and XhoI, and a larger DNA (5113 bp) was isolated. Synthetic DNA oligomers CT-1 (5'-CCGGGTGTGTACACCAAGGTTACCAACTACCTAGA CTGGATTCGTGACAACATGCGACCGTGA), CT-2 (5'-AGCTTCACGGTCGCATGTTGTCACGAATCCAGTCTA GGTAGTTGGTAACCTTGGTGTACACAC), TR-1 (5'-AGCTTGTCCTCGAGATCAATTAAAGGCTCCTTTTGG AGCCTTTTTTTTTG) and TR-2 (5'-TCGACAAAAAAAAAAGGCTCCAAAAGGAGCCTTT AATTGATCTCGAGGACA) were phosphorylated with T4 polynucleotide kinase and ligated with T4 DNA ligase to give XmaI/SalI DNA fragment (114 bp) (SEQ ID NO:53–56). The resultant DNA fragment was ligated to the XmaI/XhoI DNA to give pTQiPAdtrp. The pTQiPAdtrp (1.0 μg) was digested with EcoRI and HindIII. The resulting 4.3 kb DNA carrying trp promoter, a part of t-PA coding region (Cys92 to Trp113) and the duplicated sequence of fd phage central terminator were isolated. The 2.9 kb and 4.3 kb DNA fragments were mixed to ligate in the presence of T4 DNA ligase (300 units, Takara Shuzo) at 16° C. for 5 hours. in 40 μl of a ligation buffer consisting of 50 mM Tris.HCl 10 mM MgCl₂, 10 mM dithiothreitol and 1 mM ATP. The ligation mixture was used to transform *E. coli* JM109. The desired plasmid, designated as pCC001A, was obtained from one of the transformants resistant to ampicillin and characterized by restriction mapping.

(ii) Construction of pCC002A

Plasmid pCC001A contains a portion of t-PA (Cys92 to Trp113) gene between trp promoter and the acylase gene. In order to remove this region, pCC001A (1.0 μg) was digested with ClaI and MluI and the resulting 6.1 kb DNA fragment was isolated. On the other hand, pCCN176-3 (1 μg) was digested with MluI and Sau3AI to isolate 189 bp DNA coding for Asp7 to Arg71 of the acylase. Synthetic DNA oligomers 002a and 002b (0.5 nmole, respectively, Table 1 below) were phosphorylated with T4 polynucleotide kinase (1.5 units, Takara Shuzo) in 10 μl of a buffer (kination buffer; 50 mM Tris.HCl, 10 mM MgCl₂, 10 mM DTT, 1.0 mM ATP) at 37° C. for 1 hour and the reaction mixture was heated at 55° C. for 20 min to inactivate the enzyme (SEQ ID NO:60,61). The resulting mixture was combined to ligate with the 189 bp Sau3AI/MluI DNA in the presence of T4 ligase at 15° C. for 3 hours in 20 μl of a ligation buffer. To the resultant ligation mixture, the 6.1 kb ClaI/MluI DNA fragment was added and the mixture was incubated at 4° C. for 16 hours in the presence of additional T4 DNA ligase (300 units). The resultant ligation mixture was used to transform *E. coli* JM109. From one of the transformants, the desired plasmid pCC002A that is an expression vector for CC acylase N176 was isolated and characterized by restriction mapping.

TABLE 1

Synthetic DNA oligomers for casette mutation of
N-terminal of CC acylase N176(SEQ ID NO 57–63)

| restriction sites of each end | sequence of synthetic DNA oligomers upper strand: 5' → 3' lower strand: 3' → 5' | name/ length |
|---|---|---|
| EcoRI/ MluI | AATTCGGATCCAAGCTTA GCCTAGGTTCGAATGCGC fMetThrMetAlaAlaAsnThr | 007a/18 007b/18 |
| ClaI/ Sau3AI | CGATAAAATGACTATGGCGGCCAACACC TATTTTACTGATACCGCCGGTTGTGGCTAG | 002a/28 002b/30 |
| ClaI/ BamHI | CGATAAAATGACTATGGCAGCTAATACG TATTTTACTGATACCGTCGATTATGCCTAG fMetThrMetAlaAlaAsnThr | 013a/28 013b/30 |

(2) Construction of pCK002, a kanamycin resistant expression vector for CC acylase N176

Plasmid pCC002A was digested with DraI (TOYOBO). The resultant mixture was treated with phenol to remove the enzyme and precipitated by EtOH. The recovered DNA was suspended in 20 μl of a ligation buffer and mixed with phosphorylated EcoRI linker (2 μg, Pharmacia), followed by incubation with T4 DNA ligase (300 units) at 4° C. for 16 hours. The reaction mixture was extracted with phenol and precipitated by EtOH. The recovered DNA was digested with EcoRI and the resultant 5.6 kb DNA lacking ampicillin resistant gene was isolated by agarose gel electrophoresis. On the other hand, plasmid pA097 [which is obtainable from a transformant *Escherichia coli* JM109 (pA097) FERM BP-37721 (1 μg) was digested with EcoRI, and the resulting 1.2 kb DNA of kanamycin resistance gene was isolated. The 1.2 kb EcoRI DNA was ligated to the 5.6 kb EcoRI DNA with T4 DNA ligase (300 units) in 50 μl of a ligation buffer at 16° C. for 2 hours. The ligation mixture was used to transform *E. coli* JM109 to obtain the desired plasmid pCK002 carrying kanamycin resistant gene for antibiotic marker.

EXAMPLE 3

(Construction of pCK013, a High Expression Vector for CC Acylase N176)

(1) Construction of pCC013A
(i) Construction of pCC007A

Plasmid pCC001A was digested with EcoRI and MluI and the resulting 6.4 kb DNA fragment was isolated by agarose gel electrophoresis. The recovered DNA was ligated to synthetic DNA oligomers 007a and 007b (0.5 μg, respectively, Table 1), each of which were phosphorylated prior to the ligation reaction, with T4 DNA ligase (300 units) at 16° C. for 5 hours (SEQ ID NO:57,58). The resultant mixture was used to transform *E. coli* JM109 to obtain the desired plasmid pCC007A.

(ii) Construction of pCCNt013

Plasmid pCC007A (1.0 μg) was digested with ClaI and BamHI and the resultant 6.1 kb DNA was isolated by 5% polyacrylamide gel electrophoresis. The DNA was ligated to synthetic oligomers 013a and 013b (0.5 μg, respectively, each of which were phosphorylated, Table 1) with T4 DNA ligase (300 units) (SEQ ID NO:62,63). The ligation mixture was used to transform *E. coli* JM109 and the desired plasmid pCCNt013 was isolated from ampicillin resistant transformants.

(iii) Construction of pCC013A

Plasmid pCCNt013 was digested with BamHI and MluI and the resultant 6.1 kb DNA was isolated. On the other hand, pCC002A (1.0 μg) was digested with MluI and Sau3AI to obtain 189 bp DNA fragment. The resultant DNA was ligated to the 6.1 kb BamHI/MluI DNA fragment with T4 DNA ligase (300 units) and the ligation mixture was used to transform *E. coli* JM109. From one of the transformants resistant to ampicillin, the desired plasmid pCC013A that has AT-rich NH$_2$ terminal DNA sequence (coding for the same amino acid sequence as that of native CC acylase N176) was isolated.

(2) Construction of pCK013, a kanamycin resistant expression vector for native CC acylase N176
(i) Construction of pΔN176

Plasmid pCK002 (1.0 μg) was digested with AatII (TOYOBO) and the resultant DNA was treated with T4 DNA ligase (150 units) for self-ligation. The ligation mixture was used to transform *E. coli* JM109 to obtain the desired plasmid pΔN176 carrying a unique AtaII restriction endonuclease site.

(ii) Construction of pCK013

Plasmid pΔN176 (1.0 μg) was digested with AatII and the linearized DNA was treated with bacterial alkaline phosphatase (1 unit, Takara shuzo) in 100 mM Tris.HCl (pH 8.0) buffer 42° C. for 1 hour. The dephosphorylated DNA was isolated and ligated to the 2.5 kb AatII DNA from pCC013A with T4 DNA ligase. The ligation mixture was used to transform *E. coli* JM109 to obtain the desired plasmid pCK013 carrying kanamaycin resistant gene for marker.

EXAMPLE 4

(Point Mutation of DNA Coding for CC Acylase N176 by Kunkel's Method)

(1) Subcloning of DNA coding for CC acylase N176 to M13 phage
(i) Preparation of mp18p181

Plasmid pCC013A (An expression vector for native CC acylase N176 carrying ampicillin-resistant marker and construction of this plasmid is disclosed in European Patent Application Publication No. 558,241, p.8) was digested with HpaI and SmaI. The 842 bp DNA coding for Met$^1$ to Pro$^{267}$ of CC acylase N176 was isolated. The DNA was ligated to 7250 bp M13mp18 digested with SmaI in the presence of T4 DNA ligase and the ligation mixture was used to transform *E. coli* JM109. From one of the plaques, the desired RF DNA mp18p181 in which the part of the acylase DNA had been inserted in the reverse direction with plus ori of M13, was isolated and characterized by restriction mapping. The phage solution from which RF DNA mp18p181 was prepared was stored at 4° C. before use.

RF DNA mp18p183 was prepared from 1162 bp HpaI/ Eco47III DNA coding for Met$^1$ to Ala$^{414}$ of CC acylase N176 from pCC013A and 7250 bp M13mp18 digested with HincII in a manner similar to that described above.

(ii) Preparation of single-stranded U-mp18p181-SS(cf. Kunkel, T. A. et al. Methods Enzyml. 154, 367)

A single colony of *E. coli* CJ236 (dut-, ung-, F')(Bio-Rad Lab.) was cultured in 2 ml of 2XTY broth containing chloramphenicol (30 μg/ml) at 37° C. for 16 hours. The cells (0.1 ml) were transferred to a fresh 2XTY broth (50 ml) containing 30 μg/ml chloramphenicol and the cultivation was continued at 37° C. When the absorbance at 600 nm reached 0.3, the phage solution (MOI<0.2) of mp18p181 was added to the culture. The cultivation was continued for additional 5 hours. After centrifugation at 17,000×g at 4° C. for 15 min, the supernatant was centrifuged again. The resultant supernatant (30 ml) was treated with RNase (150 μg/ml, Sigma) at ambient temperature for 30 min, followed by addition of 7.5 ml of PEG solution (3.5M NH₄OAc in 20% polyethyleneglycol 8,000). After centrifugation (17, 000×g, 15 min, 4° C.), the residue was suspended in 200 μl of a buffer consisting of 300 mM NaCl, 100 mM Tris.HCl (pH 8.0) and 0.1 mM EDTA. The resultant solution was extracted with 200 μl of phenol and 200 μl of phenol/CHCl₃ (1:1), successively, and washed twice with CHCl₃ (200 μl). To the solution, 7.5M NH₄OAc (100 μl ) and ethanol (600 μl) were added to precipitate phage DNA. The DNA was collected by centrifugation, washed with 700 μl of ice-cooled 90% ethanol, and dried in vacuo. The purified single-stranded U-DNA (U-mp18p181-SS) was suspended in 20 μl of TE buffer and stored at 4° C. before use.

Other single-stranded U-DNAs for Kunkel's mutation method were prepared in a manner similar to that described above.

(2) Preparation of mp18p181M164A for mutant CC acylase M164A

An oligodeoxyribonucleotide SO-M164A (0.2 nmol) was incubated with T4 DNA kinase (10 units) in 15 μl of buffer consisting of 1.3 mM ATP, 10 mM dithiothreitol (DTT), 50 mM Tris.HCl, 6.6 mM in 5% polyethyleneglycol (PEG) 6,000 at 37° C. for 60 min (SEQ ID NO:2). The phosphorylated primer (1.5 μl, 20 pmol) was mixed with SS-U-DNA of mp18p181 (1 μl, 0.1 pmol) in 20 μl of a buffer consisting of 10 mM Tris.HCl (pH 8.0), 6 mM and 40 mM NaCl. The mixture was heated at 75° C. for 5 min, followed by cooling to room temperature over 40 min, and then the mixture was placed at 0° C. To the mixture, T4 DNA polymerase (15 units), T4 DNA ligase (600 units), 100 mM dithiothreitol (DTT, 6 μl), 10 mM ATP (2 μl) and 5 mM dNTP (dATP, dCTP, dGTP and dTTP, 2 μl ) were added. The resulting mixture was incubated at room temperature for 5 min and at 37° C. for 1.5 h, successively. A portion of the reaction mixture (1.0 μl ) was added to competent cells (100 μl) of *E. coli* JM109 prepared according to Sigesada's method [Sigesada, K. (1983) SAIBO-KOUGAKU (Japanese) 2, 616–626], and the cells were incubated on wet ice for 30 min. To the transformed cells, *E. coli* JM109 cultivated in L broth (A600=0.8, 200 μl) was added, and the mixture of the cells was added to 3 ml of H Top agar (1% Bactotrypton, 0.8% NaCl, 0.8% agar) preheated at 55° C. The mixture was spread over an H plate (1% Bactotryptone, 0.8% NaCl, 1.5% agar) and the plate was incubated at 37° C. for 16 h. From plaques on the plate, the desired RF DNA (mp18p181M164A) was isolated and characterized by digestion with BamHI.

(3) Preparation of pCKM164A for mutant CC acylase M164A mp18p181M164A was digested with MluI and BstBI, and the 582 bp DNA fragment was isolated by agarose gel electrophoresis. Also, pCK013 (an expression vector for native CC acylase N176 carrying kanamycin-resistant marker and construction of this plasmid is disclosed in European Patent Application Publication No. 558,241, p. 8) was digested with MluI and BstBI and a larger DNA fragment was isolated. The resultant DNA (0.03 pmol) was ligated to the 582 bp MluI/BstBI DNA (0.15 pmol) with T4 DNA ligase (300 units) in 10 μl of a ligation buffer (66 mM Tris.HCl (pH 7.6), 6.6 mM, 10 mM β-mercaptoethanol, 0.5 mM ATP) at ambient temperature for 5 hours. The ligation mixture was used to transform *E. coli* JM109. From one of the transformants resistant to kanamycin, the desired plasmid pCKM164A was isolated and characterized by restriction mapping. The transformant was named as *E. coli* JM109/pCKM164A, a glycerol stock of which was prepared in a conventional manner.

(4) Preparation of mp18p181M174A for mutant CC acylase M174A mp18p181M174A was prepared from SS-U-DNA of mp18p181 and DNA oligomer SO-M174A in a manner similar to that described above.

(5) Preparation of expression vector, pCKM174A for mutant CC acylase M174A

An expression vector for mutant CC acylase M174A and a transformant thereof were prepared in a manner similar to that described above and designated as pCKM174A and *E. coli* JM109/pCKM174A, respectively. A glycerol stock of the transformant was prepared in a conventional manner.

(6) Preparation of expression vector, pCKS166A for mutant CC acylase S166A mp18p183S166A for mutant CC acylase S166A was prepared from mp18p183 and DNA oligomer SO-S166A (5'-CATCCGCCAAAGCTTGAACCACACC GCACCCATAAG) in a manner similar to that described above. mp18p183S166A was digested with MluI and BstBI (SEQ ID NO:13). A smaller DNA fragment was isolated and ligated with a larger DNA fragment of pCK013 digested with MluI and BstBI to give pCKS166A. *E. coli* JM109 was transformed with pCKS166A to give a transformant *E. coli* JM109/pCKS166A, a glycerol stock of which was prepared in a conventional manner.

EXAMPLE 5

(Point Mutation of DNA Coding for CC Acylase N176 by PCR Method)

(1) Preparation of expression vector, pCKM164L for mutant CC acylase M164L pCK013 (template DNA, 0.5 fmol), DNA oligomer SO-MluFor [primer #1, 125 pmol, FIG. 1(*b*)] and SO-M164L [primer #2, 125 pmol, FIG. 1(*b*)] were mixed with Taq DNA polymerase (Kurabo, 1 unit) in 100 μl of a buffer consisting of 10 mM Tris.HCl (pH 9.0), 50 mM KCl, 0.1% Triton X-100, 2.5 mM and 0.2 mM dNTP (SEQ ID NO:15,25). The mixture was covered with mineral oil and PCR (Polymerase chain reaction) was carried out as follows. After an initial denaturation (96° C. for 0.5 min), the reaction was performed for 30 cycles of amplification (97° C. for 1.5 min, 50° C. for 2.5 min and 72° C. for 2.5 min), followed by final extension (72° C. for 7 min). The resultant mixture was extracted with phenol, precipitated with ethanol and digested with BamHI and MluI. The 285 bp BamHI/ MluI DNA was ligated to a larger DNA fragment of pCKM164A digested with BamHI and MluI. The ligation mixture was used to transform *E. coli* JM109. From one of the transformants resistant to kanamycin, the desired plasmid pCKM164L was isolated and characterized by restriction mapping. *E. coli* JM109 was transformed with pCKM164L to give a transformant *E. coli* JM109/ pCKM164L, a glycerol stock of which was prepared in a conventional manner.

(2) Preparation of expression vector, pCKM164G for mutant CC acylase M164G

Mutation and amplification of the DNA fragment for mutant CC acylase M164G was performed using pCK013 (template DNA) and DNA oligomers SO-MluFor [primer #1, FIG. 1(*b*)] and SO-M164G [FIG. 1(*b*)] in a manner similar to that described above. The resultant 285 bp BamHI/MluI DNA was ligated to a larger DNA fragment of pCKM164A digested with MluI and BamHI to give pCKM164G (SEQ ID NO:15,21). *E. coli* JM109 was transformed with pCKM164G (SEQ ID NO:15,21) to give a transformant *E. coli* JM109/pCKM164G, a glycerol stock of which was prepared in a conventional manner.

(3) Expression vectors for other M164 mutant CC acylase

Expression vectors for M164X mutant acylases (X=C, D, E, F, H, I, K, N, P, Q, R, S, T, V, W or Y) and transformants thereof were prepared in a manner similar to that described above.

EXAMPLE 6

(Preparation of Expression Vectors for Other Mutant CC Acylases)

(1) Construction of mp19pfu62

M13mp19 (1.0 μg) was digested with SmaI (5 units) and HindIII (5 units) and the resulting 7.2 kb DNA was isolated by agarose gel electrophoresis. On the other hand, pCK002 (construction of this plasmid is disclosed in European Patent Application Publication No. 558,241, p. 7) was digested with SmaI and HindIII and a 1.6 kb DNA was isolated. The resulting DNA was ligated to the 7.2 kb SmaI/HindIII DNA with T4 DNA ligase (300 units) in 20 μl of a ligation buffer at 15° C. for 2 h. The ligation mixture was used to transform *E. coli* JM109 to obtain the desired RF DNA mp19pfu62. The single-stranded U-DNA (SS-U-DNA) of mp19pfu62 was prepared in a manner similar to that described in Example 2 (1)(ii).

(2) Preparation of mp19pfu62M465A for mutant CC acylase M465A mp19pfu62M465A was prepared from SS-U-DNA of mp19pfu62 and DNA oligomer SO-M465A [FIG. 1(*a*)] in a manner similar to that described above (SEQ ID NO:6).

(3) Preparation of mp19pfu62M506A for mutant CC acylase M506A mp19pfu62M506A was prepared from SS-U-DNA of mp19pfu62 and DNA oligomer SO-M506A [FIG. 1(*a*)] in a manner similar to that described above (SEQ ID NO:8).

(4) Preparation of mp19pfu62M750A for mutant CC acylase M750A mp19pfu62M750A was prepared from SS-U-DNA of mp19pfu62 and DNA oligomer SO-M750A [FIG. 1(*a*)] in a manner similar to that described above (SEQ ID NO:10).

(5) Preparation of expression vector, pCKM465A for mutant CC acylase M465A mp19pfu62M465A was digested with PstI and NcoI, and a smaller DNA fragment (1271 bp) was isolated by agarose gel electrophoresis. Also, pCK013 was digested with PstI and NcoI. A larger DNA was isolated and ligated to the 1271 bp PstI/NcoI DNA with T4 DNA ligase in a buffer consisting of 50 mM Tris.HCl, 10 mM, 1.0 mM DTT and 5% PEG 6,000. The ligation mixture was used to transform *E. coli* DH10B. From one of the transformants resistant to kanamycin, the desired plasmid pCKM465A was isolated and characterized by restriction mapping. *E. coli* JM109 was transformed with pCKM465A to give a transformant *E. coli* JM109/pCKM465A, a glycerol stock of which was prepared in a conventional manner.

(6) Preparation of expression vector, pCKM506A for mutant CC acylase M506A

The pCKM506A was constructed from pCK013 and mp19pfu62M506A in a manner similar to that described above. *E. coli* JM109 was transformed with pCKM506A to give a transformant *E. coli* JM109/pCKM506A, a glycerol stock of which was prepared in a conventional manner.

(7) Preparation of expression vector, pCKM750A for mutant CC acylase M750A

The pCKM750A was constructed from pCK013 and mp19pfu62M750A in a manner similar to that described above. *E. coli* JM109 was transformed with pCKM750A to give a transformant *E. coli* JM109/pCKM750A, a glycerol stock of which was prepared in a conventional manner.

EXAMPLE 7

(Preparation of Expression Vectors for E358 Mutant CC Acylases)

(1) Preparation of expression vectors for M269I/E358 mutant CC acylases (i) Preparation of expression vector, p269I358K for mutant CC acylase M269I/E358K A larger DNA fragment of pCK013 digested with HpaI and MluI (0.5 fmol), DNA oligomer SO-E358K [5'-TAACCGGGCCATGGCGCGTCTTGACTATAT CGAACT, 125 pmol, listed in FIG. 1(*b*)(ii)] and SO-BstFor [5'-ATCGCGTCTTCGAAATACCGGGCATC, 125 pmol, listed in FIG. 1(*b*)(ii)] were mixed with Taq DNA polymerase (TaKaRa, 1 unit) in 100 μl of a buffer consisting of 10 mM Tris.HCl (pH 8.3), 50 mM KCl, 0.1% gelatin, 1.5 mM and 0.2 mM dNTP (SEQ ID NO:38,36). The mixture was covered with mineral oil and subjected to initial denaturation (96° C. for 0.5 min), 25 cycles of amplification (97° C. for 1.5 min, 50° C. for 2.5 min and 72° C. for 2.5 min.) and final extension (72° C. for 7 min). The reaction mixture was extracted with phenol, precipitated with ethanol, and digested with NcoI and BstBI. The resultant DNA (290 bp) was ligated to a larger DNA fragment of pCK013 digested with NcoI and BstBI. The ligation mixture was used to transform *E. coli* DH10B (purchased from Gibco-BRL). From one of the transformants resistant to kanamycin, the desired plasmid p269I358K was isolated and characterized by restriction mapping. *E. coli* JM109 was transformed with p269I358K to give a transformant *E. coli* JM109/p269I358K, a glycerol stock of which was prepared in a conventional manner.

(ii) Preparation of expression vectors, p269I358S and p269I358L for mutant CC-acylases M269I/E358S and M269I/E358L, respectively Expression vector for M269I/E358S (or M269I/E358L) was prepared from pCK013 and DNA oligomers SO-BstFor and SO-E358S [or SO-E358L, listed in FIG. 1(*b*)(ii)] in a manner similar to that described above (SEQ ID NO:41,37). *E. coli* JM109 was transformed with p269I358S (or p269I358L) to give a transformant *E. coli* JM109/p269I358S (or *E. coli* JM109/p269I358L), a glycerol stock of which was prepared in a conventional manner.

(2) Preparation of expression vectors for other E358 mutant CC acylases (i) Preparation of expression vector, pCCE358R for mutant CC acylase E358R mp18p183E358R for mutant CC acylase E358R was prepared from mp18p183 and DNA oligomers SO-E358R [FIG. 1(*b*)(ii)] in a manner similar to that described in Example 2 (SEQ ID NO:40). A smaller DNA of mp18p183E358R digested with MluI and NcoI was ligated to a larger DNA of pCC013A digested with MluI and NcoI to give pCCE358R. *E. coli* JM109 was transformed with pCCE358R to give a transformant *E. coli* JM109/pCCE358R, a glycerol stock of which was prepared in a conventional manner.

(ii) Preparation of expression vector, mutant CC acylase pCCE358T for E358T mp18p183E358T for mutant CC acylase E358T was prepared from mp18p183 and DNA oligomer SO-E358T [FIG. 1(*b*)(ii)] in a manner similar to that described in Example 2 (SEQ ID NO:42). A smaller DNA of mp18p183E358T digested with MluI and-NcoI was ligated to a larger DNA of pCC013A digested with MluI and NcoI to give pCCE358T. *E. coli* JM109 was transformed with pCCE358T to give a transformant *E. coli* JM109/pCCE358T, a glycerol stock of which was prepared in a conventional manner.

EXAMPLE 8

(Preparation of Multiple Mutant CC Acylases)
(1) Combination of M164L or M164A with another mutant CC acylase
(i) Preparation of expression vector, p164L269Y for mutant CC acylase M164L/M269Y pCKM164L was digested with MluI and BstBI and a smaller DNA (582 bp) was isolated. On the other hand, pCKM269Y (construction method of this plasmid is disclosed in European Patent Application Publication No. 558, 241, p. 10) was digested with MluI and BstBI. The resultant DNA (ca 6.2 kb) was isolated and ligated to 582 bp MluI/BstBI DNA. The ligation mixture was used to transform *E. coli* DH10B. From one of the transformants resistant to kanamycin, the desired p164L269Y was isolated and characterized by restriction mapping. *E. coli* JM109 was transformed with p164L269Y to give a transformant *E. coli* JM109/p164L269Y, a glycerol stock of which was prepared in a conventional manner.

(ii) Preparation of expression vector, p164L269F for mutant CC acylase M164L/M269F pCKM164L was digested with MluI and BstBI and a smaller DNA (582 bp) was isolated. On the other hand, pCKM269F (construction method of this plasmid is disclosed in European Patent Application Publication No. 558, 241, p. 15–16) was digested with MluI and BstBI. A larger DNA fragment (ca 6.2 kb) was isolated and ligated to 582 bp MluI/BstBI DNA. The ligation mixture was used to transform *E. coli* DH10B. From one of the transformants resistant to kanamycin, the desired p164L269F was isolated and characterized by restriction mapping. *E. coli* JM109 was transformed with p164L269F to give a transformant *E. coli* JM109/p164L269F, a glycerol stock of which was prepared in a conventional manner.

(iii) Preparation of expression vector, p164L269Y305S for mutant CC acylase M164L/M269Y/C305S p164L269Y305S was prepared from pCKM164L and p269Y305S (construction method of this plasmid is disclosed in European Patent Application Publication No. 558, 241, p. 10) in a manner similar to that described above. *E. coli* JM109 was transformed with p164L269Y305S to give a transformant *E. coli* JM109/p164L269Y305S, a glycerol stock of which was prepared in a conventional manner.

(iv) Preparation of expression vector, p164L174A for mutant CC acylase M164L/M174A HpaI/NcoI DNA (1122 bp) from pCKM164L (template DNA, 0.5 fmol), DNA oligomers SO-MluFor [primer #1, 125 pmol, FIG. 1(b)(i)] and SO-M174A2 (5'-GACCGGCAGCGCTAGCGCCCGCCAGAGCTTGA, primer #2, 125 pmol) were mixed with Taq DNA polymerase (TaKaRa, 1 unit) in 100 µl of a buffer consisting of 10 mM Tris.HCl (pH 8.3), 50 mM KCl, 0.1% gelatin, 1.5 mM and 0.2 mM dNTP (SEQ ID NO:64). The mixture was covered with mineral oil and subjected to initial denaturation (96° C. for 0.5 min), 25 cycles of amplification (97° C. for 1.5 min, 50° C. for 2.5 min and 72° C. for 2.5 min) and final extension (72° C. for 7 min). The resultant mixture was extracted with phenol, precipitated with ethanol, and digested with MluI and NheI. The resultant DNA was ligated to a larger DNA fragment of pCKM174A digested with MluI and NheI to give the desired plasmid p164L174A. *E. coli* JM109 was transformed with the p164L174A to give a transformant *E. coli* JM109/p164L174A, a glycerol stock of which was prepared in a conventional manner.

(v) Preparation of expression vector, p164A174A for mutant CC acylase M164A/M174A p164A174A was prepared from pCKM164A (template DNA), SO-MluFor [primer #1, FIG. 1(b)(i)], SO-M174A [primer #2, FIG. 1(a)] and pCKM174A (vector DNA) in a manner similar to that described above (SEQ ID NO:15,14). *E. coli* JM109 was transformed with p164A174A to give a transformant *E. coli* JM109/p164A174A, a glycerol stock of which was prepared in a conventional manner.

(vi) Preparation of expression vector, p164A269Y for mutant CC acylase M164A/M269Y M164A was digested with MluI and BstBI and a small DNA (582 bp) was isolated. On the other hand, pCKM269Y was digested with MluI and BstBI. The resultant larger DNA fragment was ligated to the 582 bp MluI/BstBI DNA and the ligation mixture was used to transform *E. coli* DH10B. From one of the transformants resistant to kanamycin, the desired plasmid p164A269Y was isolated and characterized by restriction mapping. *E. coli* JM109 was transformed with p164A269Y to give a transformant *E. coli* JM109/p164A269Y, a glycerol stock of which was prepared in a conventional manner.

(vii) Preparation of expression vectors for mutant CC acylases, M164L/M174A/M269Y, M164L/M174A/M269F and M164A/M174A/M269Y/C305S A smaller DNA of p164L174A digested with MluI and BstBI was ligated to a larger DNA fragment of pCKM269Y (or pCKM269F or p269Y305S) digested with MluI and BstBI to give the desired vector, p164L174A269Y (or p164L174A269F or p164A174A269Y305S). *E. coli* JM109 was transformed with the p164L174A269Y (or p164L174A269F or p164A174A269Y305S) to give a transformant *E. coli* JM109/p164L174A269Y (or *E. coli* JM109/p164L174A269F or *E. coli* JM109/p164A174A269Y305S), a glycerol stock of which was prepared in a conventional manner.

(viii) Preparation of expression vector, p164L174A269Y305S750A for mutant CC acylase, M164L/M174A/M269Y/C305S/M750A pCKM750A was digested with PstI and NcoI. A smaller DNA was isolated and ligated to the larger DNA of p164L174A269Y305S digested with PstI and NcoI to give the desired plasmid. *E. coli* JM109 was transformed with p164L174A269Y305S750A to give a transformant *E. coli* JM109/p164L174A269Y305S750A, a glycerol stock of which was prepared in a conventional manner.

(2) Combination of A49L with other mutant acylases
(i) Preparation of mp18p181A49L for mutant CC acylase A49L mp18p181A49L was prepared from SS-U-DNA of mp18p181 and DNA oligomer SO-A49L in a manner similar to that described in Example 2 (SEQ ID NO:12).

(ii) Preparation of expression vector, pCKA49L for mutant CC acylase A49L mp18p181A49L was digested with ClaI and MluI and a 218 bp DNA was isolated. On the other hand, pCC013A was digested with ClaI and MluI. The resultant larger DNA was isolated and ligated to the 218 bp ClaI/MluI DNA. The ligation mixture was used to transform *E. coli* JM109. From one of the transformants resistant to ampicillin, an expression vector for mutant CC acylase A49L, designated as pCCA49L, was isolated and characterized by restriction mapping. A 250 bp HpaI/MluI DNA fragment from pCCA49L was ligated to a larger DNA fragment of pCK013 digested with HpaI and MluI to give pCKA49L.

(iii) Comparison of expression of native CC acylase and mutant CC acylase A49L

Glycerol stock solution (1 ml) of *E. coli* JM109/pCKA49L (or JM109/pCK013) which had been prepared by transforming *E. coli* JM109 with the plasmid pCKA49L (or pCK013) in a conventional manner was transferred to 100 ml of L broth containing 50 μg/ml kanamycin, and the mixture was cultured at 30° C. for 8 hours. The cultured broth (3.75 ml) was added to 25 ml of N-3 broth (ingredients: 5% soybean sauce, 1% glycerol, 1.25% $K_2HPO_4$, 0.38% $KH_2PO_4$, 50 μg/ml thiamine.HCl, 2 mM $MgSO_4.7H_2O_4$ 0.2 mM $CaCl_2.2H_2O$, 0.05 mM $FeSo_4.7H_2O$) containing 25 μg/ml kanamycin, and the mixture was cultured at 22.5° C. for 16 hours. At 16 h, 3-indoleacrylic acid (IAA) was added to the cultured broth to a final concentration of 20 μg/ml and the cultivation was continued for additional 56 hours. Cells were harvested by centrifugation at 14,000 rpm for 15 min at 4° C., suspended in 40 ml of TE buffer (pH 8.0) and lysed by sonication. The lysate was centrifuged at 14,000 rpm for 20 min at 4° C. to obtain the supernatant (designated as "soup" fraction). The residues were resuspended in 40 ml of a buffer containing 100 mM Tris.HCl (pH 8.0), 1 mM EDTA and 8M urea and lysed by sonication. After centrifugation to remove insoluble materials, the supernatant was collected (designated as "ppt" fraction). The "soup" and "ppt" fractions of mutant CC acylase A49L and native CC acylase N176 were analyzed by 15% SDS-PAGE. The cellular insoluble precursor protein was greatly decreased by mutation from a native CC acylase to a mutant CC acylase A49L. The results corresponded to the amounts of mature acylases (native CC acylase or mutant CC acylase A49L) in "soup" assayed by reversed phase HPLC (in the following Table).

| A49L (units/ml broth) | native (units/ml broth) |
|---|---|
| 72.6 | 35.6 |

(iv) Preparation of expression vector, p49L164L174A269Y for mutant CC acylase, A49L/M164L/M174A/M269Y The 772 bp MluI/NcoI DNA from p164L174A269Y was ligated to a larger DNA of pCKA49L digested with MluI and NcoI to give the desired plasmid p49L164L174A269Y. *E. coli* JM109 was transformed with p49L164L174A269Y to give a transformant *E. coli* JM109/p49L164L174A269Y, a glycerol stock of which was prepared in a conventional manner.

EXAMPLE 9

(Expression and Purification of Mutant CC Acylases)

(1) Expression of mutant CC acylase M164A

A glycerol stock of *E. coli* JM109/pCKM164A (0.5 ml) was added to 50 ml of L broth containing 50 μg/ml kanamycin and the mixture was cultivated at 30° C. for 8 h. The cultivated broth (3.75 ml) was transferred to 25 ml of N-3 broth (5.0% soybean source (Osaka Shokuhinn Kagaku), 0.608% $Na_2HPO_4$, 0.7% $KH_2PO_4$, 0.7% $K_2HPO_4$, 0.12% $(NH_4)_2SO_4$, 0.02% $NH_4Cl$, 0.0011% $FeSO_4.7H_2O$, 0.0011% $CaCl_2.2H_2O$, 0.000276% $MnSO_4.nH_2O$, 0.000276% $AlCl_3.6\ H_2O$, 0.00011% $CoCl_2.6H_2O$, 0.0000552% $ZnSO_4.7H_2O$, 0.0000552% $NaMoO_4.2H_2O$, 0.0000276% $CuSO_4.7H_2O$, 0.0000138% $H_3BO_4$, 50 μg/ml vitamin B1, 0.048% $MgSO_4$) containing 1.0% glycerol and 12.5 μg/ml kanamycin. The mixture was incubated at 20°–22° C. for 88 h with addition of β-indoleacrylic acid (final concentration 20 μg/ml) at 16 h and glycerol (final concentration 1.0%) at 16 and 24 h after the start of cultivation. Cells were harvested by centrifugation (8,000 rpm at 4° C. for 10 min), suspended in 10 ml of TE buffer (10 mM Tris.HCl (pH 8.0), 1.0 mM EDTA) and lysed by sonication. After centrifugation (15,000 rpm at 4° C. for 20 min), the supernatant (crude lysate) was stored at 4° C. until use.

(2) Purification of M164A

The crude lysate (1.0 ml) was filtrated using a 0.45 μm column guard (Millipore) and applied to a TSK-gelTM DEAE-5PW (TOSOH, 4.6×50 mm) high performance liquid chromatography column. Elution was performed with a concave gradient from 80% of A buffer [25 mM Tris.HCl (pH 8.0)]+20% of B buffer [0.5M NaCl-25 mM Tris.HCl (pH 8.0)] to 50% of A buffer+50% of B buffer over 30 min at a flow rate of 1.0 ml/min. Absorbance at 230 nm was used to monitor the eluate. The last main peak eluted with approximately 0.16M NaCl was collected to obtain a pure preparation of mutant CC acylase M164A.

(3) Expression of other mutant CC acylases

Cultivation of *E. coli* JM109 carrying another expression vector (such as pCKM164L, pCKM164G, pCKM174A, pCKM465A, pCKM506A, pCKM750A, p164L/269Y, p164L/269Y/305S, p164L/174A/269Y/305S, p269I/358K, p269I/358S, p164L/269F, p164L/174A/269F, pCKS166A, p164L/174A/269Y/305S/750A, p164A/269Y, pCK49L and p49L/164L/174A) and preparation of the crude lysate was performed in a manner similar to that described above.

(4) Purification of other mutant CC acylases

Other mutant CC acylases (such as M164L, M164G, M174A, M465A, M506A, M750A, M164L/M269Y, M164L/M269Y/C305S, M164L/M174A/M269Y/S305S, M269I/E358K, M269I/E358S, M164L/M269F, M164L/M174A/M269F, S166A, M164L/M174A/M269Y/C305S/M750A, M164A/269Y, and A49L/M164L/M174A) were purified from each of crude lysates in a manner similar to that described above.

(5) Identification of mutant CC acylases

Purified mutant CC acylases such as M164A, M164L, M164G, M174A, M465A, M506A, M750A, M164L/M269Y, M164L/M269Y/C305S, M164L/M174A/M269Y/S305S, M269I/E358K, M269I/E358S, M164L/M269F, M164L/M174A/M269F, S166A, M164L/M174A/M269Y/C305S/M750A, M164A/269Y, and A49L/M164L/M174A were characterized by 12.5% SDS-PAGE analysis and reversed phase HPLC. From the SDS-PAGE analysis in the presence of β-mercaptoethanol, each purified acylase was confirmed to consist of two independent subunits, 25.4 kDa and 58.4 kDa peptides corresponding to α and β subunits, respectively, whose molecular weights were calculated from their mobility on gel electrophoresis. In HPLC analysis, each purified acylase was dissociated to 2 independent peptides, α and β subunits, which were eluted at approximately 8.7 and 5.8 min, respectively [HPLC conditions, column: 5C4-AR-300, 4.6×50 mm; eluate: linear gradient from 35% to 70% aqueous acetonitrile containing 0.05% trifluoroacetic acid over 10 min; detection: 214 nm]. The both subunits of each mutant acylase were isolated by the reversed phase HPLC system and determined to be identical to the sequence of native acylase by amino terminal sequence analysis with 473A protein sequencer (Applied Biosystems).

EXAMPLE 10

(DNA Sequence Analysis)

DNA sequence of vectors for mutant acylases such as M164A, M164L, M164G, M174A, M465A, M506A, M750A, M164L/M269Y, M164L/M269Y/C305S, M164L/M174A/M269Y/S305S, M269/E358K, M269I/E358S, M164L/M269F, M164L/M174A/M269F, S166A, M164L/M174A/M269Y/C305S/M750A, M164A/269Y, and A49L/M164L/M174A was determined by 373A DNA sequencer (Applied Biosystems) and confirmed to be identical to that as expected.

EXAMPLE 11

(CC Acylase Activity)

The CC acylase activity at pH 8.7 of each of the mutant acylases as listed in Table 2 was determined in the same manner as described above. The results are shown in Table 2.

TABLE 2

Relative activity of CC acylase:

| mutant acylase | CC acylase activity |
| --- | --- |
| native (N176) | 100* |
| M164L | 122 |
| M174A | 123 |
| M465A | 136 |
| M506A | 140 |
| M750A | 142 |
| M164L/M269Y | 161 |
| M164L/M269Y/C305S | 141 |
| M164L/M174A/M269Y/C305S | 155 |
| M269I/E358K | 153 |
| M269I/E358S | 184 |
| M164L/M269F | 193 |

TABLE 2-continued

Relative activity of CC acylase:

| mutant acylase | CC acylase activity |
| --- | --- |
| M164L/M174A/M269F | 184 |
| S166A | 186 |
| M164L/M174A/M269Y | 245 |
| M164L/M174A/M269Y/C305S/M750A | 192 |
| M164A/M269Y | 172 |
| A49L/M164L/M174A/M269Y | 226 |

(*: calculated as native = 100%)

EXAMPLE 12

(GL-7ACA Acylase Activity)

The GL-7ACA acylase activity at pH 7.5 of each of the mutant acylases as listed in Table 3 was determined in the same manner as described above. The results are shown in Table 3.

TABLE 3

Relative activity of GL-7ACA acylase:

| mutant acylase | GL-7ACA acylase activity |
| --- | --- |
| native (N176) | 100* |
| M164A | 167 |
| M164G | 162 |

(*: calculated as native = 100%)

---

We claim:

1. A mutant CC acylase wherein at least one amino acid at the $Ala^{49}$, $Met^{164}$, $Ser^{166}$, $Met^{174}$, $Glu^{358}$, $Met^{465}$, $Met^{506}$, or $Met^{750}$ position of the amino acid sequence of the native CC acylase is replaced by a different amino acid.

2. A mutant Cephalosporin C acylase of claim 1, which is represented by the following formula in its precursor form before processing into α-subunit and β-subunit thereof:
A1-48-X1-A50-163-X2-Gly-X3-A167-173-X4-A175-357-X5-A359-464-X6-A466-505-X7-A507-749-X8-A751-773
wherein A1-48 is the same amino acid sequence as that from $Thr^1$ to $Glu^{48}$ of native CC acylase,
A50-163 is the same amino acid sequence as that from $Asp^{50}$ to $Leu^{163}$ of native CC acylase,
A167-173 is the same amino acid sequence as that from $Val^{167}$ to $Arg^{173}$ of native CC acylase,
A175-357 is the same amino acid sequence as that from $Leu^{175}$ to $Val^{357}$ of native CC acylase,
A359-464 is the same amino acid sequence as that from $Thr^{359}$ to $Ala^{464}$ of native CC acylase,
A466-505 is the same amino acid sequence as that from $Pro^{466}$ to $Ile^{505}$ of native CC acylase,
A507-749 is the same amino acid sequence as that from $Lys^{507}$ to $Ala^{749}$ of native CC acylase,
A751-773 is the same amino acid sequence as that from $Val^{751}$ to $Ala^{773}$ of native CC acylase,
X1 is Ala or a different amino acid,
X2, X4, X6, X7 and X8 are each Met or a different amino acid,
X3 is Ser or a different amino acid and
X5 is Glu or a different amino acid,
providing that $Met^{269}$ and/or $Cys^{305}$ may be replaced by (a) different amino acid(s) in the above formula, and when X1 is Ala, X2, X4, X6, X7 and X8 are each Met, X3 is Ser and X5 is an amino acid other than Glu.

3. A mutant Cephalosporin C acylase of claim 2, in which X1 is leucine, X3 is alanine, and $Met^{269}$ is replaced by tyrosine.

4. An isolated DNA which encodes the Cephalosporin C acylase of claim 1.

5. An expression vector which comprises the DNA of claim 4.

6. A host cell transformed by the expression vector of claim 5.

7. A process for producing a mutant Cephalosporin C acylase, which comprises culturing a host cell transformed by an expression vector which comprises DNA which encodes the Cephalosporin C acylase of claim 1 in an aqueous nutrient medium and recovering the mutant Cephalosporin C acylase from the cultured broth.

8. A process for preparing a compound of the formula (I):

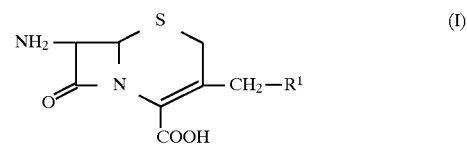

wherein
$R^1$ is acetoxy, hydroxy, or hydrogen, or its salt, which comprises contacting a compound of the formula (II):
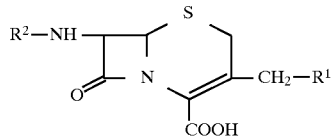
(II)
wherein
$R^1$ is the same as defined above and
$R^2$ is carboxylic acyl, or its salt
with the cultured broth of the transformant of claim 6 or its processed material.
* * * * *